US007649011B2

(12) United States Patent
Melikian et al.

(10) Patent No.: US 7,649,011 B2
(45) Date of Patent: Jan. 19, 2010

(54) INHIBITORS OF HUMAN TUMOR-EXPRESSED CCXCKR2

(75) Inventors: Anita Melikian, San Francisco, CA (US); Jennifer Burns, San Mateo, CA (US); Brian E. McMaster, Mountain View, CA (US); Thomas Schall, Palo Alto, CA (US); J. J. Wright, Redwood City, CA (US)

(73) Assignee: Chemocentryx, Inc., Mountain View, CA (US)

( * ) Notice: Subject to any disclaimer, the term of this patent is extended or adjusted under 35 U.S.C. 154(b) by 647 days.

(21) Appl. No.: 10/743,281

(22) Filed: Dec. 22, 2003

(65) Prior Publication Data

US 2004/0171655 A1 Sep. 2, 2004

Related U.S. Application Data

(60) Provisional application No. 60/434,912, filed on Dec. 20, 2002, provisional application No. 60/516,151, filed on Oct. 30, 2003.

(51) Int. Cl.
*A61K 31/541* (2006.01)
*A61K 31/496* (2006.01)
*C07D 417/02* (2006.01)

(52) U.S. Cl. .................. 514/414; 514/418; 514/422; 514/428; 548/455; 548/517; 548/518; 548/525; 548/527; 548/567

(58) Field of Classification Search ................ 548/574, 548/491, 561, 455, 517, 518, 525, 527, 567; 514/414, 418, 422, 428

See application file for complete search history.

(56) References Cited

U.S. PATENT DOCUMENTS

| 3,135,608 | A | 6/1964 | Dickard |
| 4,166,452 | A | 9/1979 | Generales, Jr. |
| 4,256,108 | A | 3/1981 | Theeuwes |
| 4,265,874 | A | 5/1981 | Bonsen et al. |
| 4,927,838 | A | 5/1990 | Guthrie et al. |
| 5,994,519 | A | 11/1999 | Osbourn et al. |
| 6,084,075 | A | 7/2000 | Lind et al. |
| 6,140,064 | A | 10/2000 | Loetscher et al. |
| 6,156,520 | A | 12/2000 | Inglese et al. |
| 6,180,336 | B1 | 1/2001 | Osbourn et al. |
| 6,184,358 | B1 | 2/2001 | Loetscher et al. |
| 6,215,658 | B1 | 4/2001 | Bodini |
| 6,329,159 | B1 | 12/2001 | Andrew et al. |
| 6,365,356 | B1 | 4/2002 | Gershengorn |
| 6,448,054 | B1 | 9/2002 | Poznansky et al. |
| 2002/0004215 | A1 | 1/2002 | Osbourn et al. |
| 2002/0025536 | A1 | 2/2002 | Gyuris et al. |
| 2002/0034757 | A1 | 3/2002 | Cubicciotti |
| 2002/0037539 | A1 | 3/2002 | Qin et al. |
| 2002/0048786 | A1 | 4/2002 | Rosen et al. |
| 2002/0061599 | A1 | 5/2002 | Elling et al. |
| 2002/0061834 | A1 | 5/2002 | Rosen et al. |
| 2002/0064770 | A1 | 5/2002 | Nestor, Jr. et al. |
| 2002/0076710 | A1 | 6/2002 | Papsidero et al. |
| 2004/0171655 | A1* | 9/2004 | Melikian et al. ............ 514/357 |

FOREIGN PATENT DOCUMENTS

| EP | 0 897 980 A2 | 2/1999 |
| WO | WO 98/11218 | 3/1998 |
| WO | WO 98/14480 | 4/1998 |
| WO | WO 99/50461 | 10/1999 |
| WO | WO 01/55107 A2 | 1/2001 |
| WO | WO 01/98272 A1 | 6/2001 |
| WO | WO 02/24649 A1 | 9/2001 |
| WO | WO 03/007888 A2 | 7/2002 |

OTHER PUBLICATIONS

Theodora VoskogLou-Nomokos et al. (Clinical Research, vol. 9, pp. 4227-4239, Sep. 15, 2003.*
Abdel-Magid et al., "Reductive Amination of Aldehydes and Ketones by Using Sodium Triacetoxyborohydride[1]," *Tetrahedron Lett.*, 31:5595-5598 (1990).
Babcock et al., "Ligand Binding Characteristics of CXCR4 Incorporated into Paramagnetic Proteoliposomes," *J. Biol. Chem.*, 276(42):38433-38440 (2001).
Baribaud et al., "Antigenically Distinct Conformations of CXCR4," *J. Virol.*, 75(19):8957-8967 (2001).
Barney et al., "A Convenient Synthesis of Hindered Amines and α-Trifluoromethylamines from Keytones," *Tetrahedron Lett.*, 31:5547 (1990).
Bertolini et al., "Endostatin, an antiangiogenic drug, induces tumor stabilization after chemotherapy or anti-CD20 therapy in a NOD/SCID mouse model of human high-grade non-Hodgkin lymphoma," *Blood*, 1(96):282-287 (2000).
Bertolini et al., "CXCR4 Neutralization, a Novel Therapeutic Approach for Non-Hodgkin's Lymphoma[1]," *Cancer Research*, 62:3106-3112 (2002).
Dairaghi et al., "HHV8-encoded vMIP-I Selectively Engages Chemokine Receptor CCR8," *J. Biol. Chem.*, 274(31):21569-21574 (1999).
Tatjana Dragic, "An overview of the determinants of CCR5 and CXCR4 co-receptor function," *J. Gen. Virol.*, 82:1807-1814 (2001).
Förster et al., "Intracellular and Surface Expression of the HIV-1 Coreceptor CXCR4/Fusin on Various Leukocyte Subsets: Rapid Internalization and Recycling Upon Activation," *J. Immunol.*, 160:1522-1531 (1998).

(Continued)

*Primary Examiner*—Sabiha Qazi
(74) *Attorney, Agent, or Firm*—Brinks Hofer Gilson & Lione

(57) ABSTRACT

Pharmaceutical compositions containing organic compounds or salts thereof that serve as modulators for the SDF-1 or I-TAC chemokines are disclosed. The compounds and compositions are useful in the treatment of cancer, especially in the inhibition of cancer proliferation, growth, and metastasis. Methods of interfering with SDF-1 and/or I-TAC binding to the CCXCKR2 receptor and treating cancer using the compounds and pharmaceutical compositions of the present invention are also disclosed.

23 Claims, No Drawings

OTHER PUBLICATIONS

Gerlach et al., "Molecular Interactions of Cyclam and Bicyclam Non-peptide Antagonists with the CXCR4 Chemokine Receptor," *J. Biol. Chem.*, 276(17):14153-14160 (2001).

Gosling et al., "Cutting Edge: Identification of a Novel Chemokine Receptor That Binds Dendritic Cell- and T Cell-Active Chemokines Including ELC, SLC, and TECK," *J. Immunol.*, 164(6):2851-2856 (2000).

Gribble GW and Nutaitis CF, "Reactions of Sodium Borohydride in Acidic Media; XVI. N-Methylation of Amines with Paraformaldehyde/Trifluoroacetic Acid," *Synthesis*, 709 (1987).

Kevill DN and Rissmann TJ, "Correlation of the Rates of Solvolysis of Allyl and Benzyl Arenesulphonates," *J. Chem. Soc. Perkin Trans.* 2:717-720 (1984).

Kledal et al., "A Broad-Spectrum Chemokine Antagonist Encoded by Kaposi's Sarcoma-Associated Herpesvirus," *Science*, 277:1656-1659 (1997).

Lee et al., "Epitope Mapping of CCR5 Reveals Multiple Conformational States and Distinct but Overlapping Structures Involved in Chemokine and Coreceptor Function," *J. Biol. Chem.*, 274(14):9617-9626 (1999).

Lin et al., "Antiangiogenic gene therapy targeting the endothelium-specific receptor tyrosine kinase Tie2," *Proc. Natl. Acad. Sci. USA*, 95:8829-8834 (1998).

Lance A. Liotta, "An attractive force in metastasis," *Nature*, 410:24-25 (2001).

Mattson et al., "An Improved Method for Reductive Alkylation of Amines Using Titanium (IV) Isopropoxide and Sodium Cyanoborohydride[1]," *J. Org. Chem.*, 55:2552-2554 (1990).

Moepps et al., "Two murine homologues of the human chemokine receptor CXCR4 mediating stromal cell-derived factor 1α activation of $G_{12}$ are differently expressed in vivo," *Eur. J. Immunol.*, 27:2102-2112 (1997).

Muller et al., "Involvement of chemokine receptors in breast cancer metastasis," *Nature*, 410:50-56 (2001).

Bernhard Neises & Wolfgang Steglich, "Simple Method for the Esterification of Carboxylic Acids[1]," *Angew. Chem. Int. Ed. Engl.*, 17(7):522-524 (1978).

Neote et al., "Molecular Cloning, Functional Expression, and Signaling Characteristics of a C-C Chemokine Receptor," *Cell*, 72:415-425 (1993).

Oppenheim et al., "Properties of the Novel Proinflammatory Supergene "Intercrine" Cytokine Family[1]," *Annu. Rev. Immunol.*, 9:617-648 (1991).

Parolin et al., "Use of Murine CXCR-4 as a Second Receptor by Some T-Cell-Tropic Human Immunodeficiency Viruses," *J. Virol.*, 72(2):1652-1656 (1998).

Ponath et al., "Molecular Cloning and Characterization of a Human Eotaxin Receptor Expressed Selectively on Eosinophils," *J. Exp. Med.*, 183:2437-2448 (1996).

Power et al., "Molecular Cloning and Functional Expression of a Novel CC Chemokine Receptor cDNA from a Human Basophilic Cell Line," *J. Biol. Chem.*, 270(33):19495-19500 (1995).

Pulaski et al., "Cooperativity of *Staphylococcal aureus* Enterotoxin B Superantigen, Major Histocompatibility Complex Class II, and CD80 for Immunotherapy of Advanced Spontaneous Metastases in a Clinically Relevant Postoperative Mouse Breast Cancer Model[1]," *Cancer Research*, 60:2710-2715 (2000).

Thomas J. Schall, "Biology of the Rantes/sis Cytokine Family," *Cytokine*, 3(3):165-183 (1996).

Watanabe et al., "The Selective Amination of Carbonyl Compounds Using Iron Pentacarbonyl," *Tetrahedron Lett.*, No. 22:1879-1880 (1974).

Wegner et al., "Genomic Organization and Functional Characterization of the Chemokine Receptor CXCR4, a Major Entry Co-receptor for Human Immunodeficiency Virus Type 1," *J. Biol. Chem.*, 273(8):4754-4760 (1998).

Yoshida et al., "Identification of Single C Motif-1/Lymphotactin Receptor XCR1," *J. Biol. Chem.*, 273(26):16551-16554 (1998).

* cited by examiner

INHIBITORS OF HUMAN TUMOR-EXPRESSED CCXCKR2

RELATED APPLICATIONS

This application claims priority to U.S. provisional application Ser. No. 60/434,912 filed Dec. 20, 2002 and U.S. provisional application Ser. No. 60/516,151 filed Oct. 30, 2003. The disclosures of the priority applications are incorporated by reference herein in their entirety.

BACKGROUND

The present invention is directed to novel compounds and pharmaceutical compositions that inhibit the binding of the SDF-1 chemokine (also known as the CXCL12 chemokine) or I-TAC (also known as CXCL11) to the chemokine receptor CCXCKR2. These compounds are useful in preventing tumor cell proliferation, tumor formation, and metastasis.

Chemokines are a superfamily of small, cytokine-like proteins that induce cytoskeletal rearrangement, firm adhesion to endothelial cells, and directional migration and may also effect cell activation and proliferation. Chemokines act in a coordinated fashion with cell surface proteins to direct the specific homing of various subsets of cells to specific anatomical sites.

Early research efforts by a number of groups have indicated a role for the chemokine receptor CXCR4 in metastasis and tumor growth. Muller, et al., "Involvement of Chemokine Receptors in Breast Cancer Metastasis," Nature, 410:50-56 (2001) demonstrated that breast tumor cells use chemokine-mediated mechanisms, such as those regulating leukocyte trafficking, during the process of metastasis. Tumor cells express a distinct, non-random pattern of functionally active chemokine receptors. Signaling through CXCR4 mediates actin polymerization and pseudopodia formation in breast cancer cells, and induces chemotactic and invasive responses. Additionally, the organs representing the main sites of breast cancer metastasis (such as lymph nodes, bone marrow, and lungs) are the most abundant sources of ligand for the CXCR4 receptor.

Using immunodeficient mice, Muller and colleagues succeeded in reducing the metastasis of injected human breast cancer cells by treating mice with an antibody known to bind CXCR4. Their finding suggests that breast cancer metastasis could be reduced by treating a patient with a CXCR4 antagonist.

Bertolini, et al., "CXCR4 Neutralization, a Novel Therapeutic Approach for Non-Hodgkin's Lymphoma," Cancer Research, 62:3106-3112 (2002) demonstrated a reduction of tumor volume as well as prolonged survival of immunodeficient mice injected with human lymphoma cells treated with anti-CXCR4 antibodies. They interpreted their finding to mean that tumor volume could be reduced by treating a patient with a CXCR4 antagonist.

More recent studies suggest that another chemokine receptor, CCXCKR2, may also be a potential candidate in the treatment of cancer. CCXCKR2 is preferentially expressed in transformed cells over normal cells, with detectable expression in a number of human cancers. In vitro studies indicate that proliferation of CCXCKR2 expressing cells can be inhibited by an antagonist of CCXCKR2. In vivo studies in mice indicate that CCXCKR2 antagonists can inhibit tumor formation and tumor growth.

The potential importance of CCXCKR2 is illustrated by an alternative interpretation of the reduction in tumor volume seen by Bertolini and colleagues. This reduction could clearly be the result of an antibody-mediated clearance, and not the result of the anti-CXCR4 antibody as originally believed. In an antibody-mediated clearance, any antibody that recognized a protein on the cell surface of the lymphoma cells would have had the same effect as that attributed to the anti-CXCR4 antibody. Unfortunately, Bertolini and colleagues studies are inconclusive as to whether the observed tumor response was due to antibody-mediated clearance or interaction with CXCR4.

However it is now known that the lymphoma cells used by Bertolini and colleagues express both-CXCR4 and CCX-CKR2. SDF-1 is the only ligand for CXCR4. SDF-1 and I-TAC both bind CCXCKR2. Using anti-SDF-1 antibody, it has now been shown that antagonists of CCXCKR2 are responsible for the reduction in tumor load and increased survival rate. Because SDF-1 is the only ligand for CXCR4, one would expect neutralization of SDF-1 with anti-SDF-1 antibody would be equivalent to the neutralization of CXCR4 with anti-CXCR4 antibody. However, experiments using an anti-SDF-1 antibody demonstrated only a partial reduction in tumor load and an increased survival rate. This leads one to believe that CCXCKR2 is the actual target, as the continued activity is likely due to the interactions of the second ligand, I-TAC, with CCXCKR2.

Until recently, the possible importance of CCXCKR2 in tumor cell proliferation, tumor growth, and metastasis was unknown. Now, with recent evidence pointing to the ability of certain CCXCKR2 antagonists to prevent the growth and spread of cancer, and expression patterns indicating a limited tissue distribution for the CCXCKR2 receptor, it would be beneficial to provide compounds that are able to bind specifically to the CCXCKR2 receptor on tumor cells with potentially few side effects.

SUMMARY

The present invention is directed to novel compounds and compositions containing small molecule modulators that bind to the CCXCKR2 receptor. In general, the novel compounds have the structure (I):

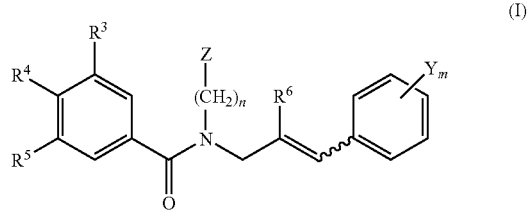

where $R^3$, $R^4$, $R^5$ and $R^6$, Y, Z, m and n are defined below.

In one embodiment, the novel compounds are of the structure (II):

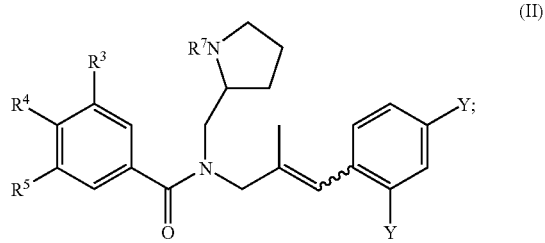

where $R^3$, $R^4$, $R^5$ and $R^7$, and Y are defined below.

In another embodiment, compositions that include the modulators of the present invention and a pharmaceutically-acceptable carrier are disclosed.

In another embodiment, a method of inhibiting the binding of SDF-1, I-TAC or both to a CCXCKR2 receptor is disclosed.

In another embodiment, a method of treating cancer is disclosed.

These and other embodiments are discussed more fully below.

DETAILED DESCRIPTION

The present invention provides compositions that include a pharmaceutically acceptable carrier and an active compound that modulates the binding of SDF-1 and/or I-TAC chemokines to the CCXCKR2 receptor expressed by cancer cells. Preferably, these active compounds bind to the CCXCKR2 receptor on tumor cells, but do not appreciably bind with lymphoid-derived cells or myeloid cells. The compounds and compositions of the present invention are useful for treating cancer, especially for reducing the incidence of breast cancer metastasis.

Definitions

When describing the compounds, compositions, methods, and processes of the invention, the following terms are defined as follows, unless otherwise indicated.

"Alkoxy" refers to an —OR' group. Representative alkoxy groups include, by way of example, methoxy, ethoxy, isopropyloxy, trifluoromethoxy and difluoromethoxy.

"Alkyl" by itself or as part of another substituent refers to a hydrocarbon group which may be linear, cyclic, or branched or a combination thereof having the number of carbon atoms designated (i.e., $C_{1-8}$ means one to eight carbon atoms). Examples of alkyl groups include methyl, ethyl, n-propyl, isopropyl, n-butyl, t-butyl, isobutyl, sec-butyl, cyclohexyl, cyclopentyl, (cyclohexyl)methyl, cyclopropylmethyl and the like. Examples of substituted alkyl include haloalkyl, thioalkyl, aminoalkyl, and the like.

"Alkylene" by itself or as part of another substituent means a divalent radical derived from an alkane, as exemplified by —CH₂CH₂CH₂CH₂—. Typically, alkyl (or alkylene) groups having 8 or fewer carbon atoms are preferred in the present invention. Representative alkylene groups include, by way of example, methylene, ethane-1,2-diyl ("ethylene"), propane-1,2-diyl, propane-1,3-diyl, butane-1,4-diyl, pentane-1,5-diyl, and the like.

"Alkenyl" refers to an unsaturated hydrocarbon group which may be linear, cyclic or branched or a combination thereof. Alkenyl groups with 2-10 carbon atoms are preferred. The alkenyl group may contain 1, 2 or 3 carbon-carbon double bonds. Examples of alkenyl groups include ethenyl, n-propenyl, isopropenyl, n-but-2-enyl, n-hex-3-enyl and the like.

"Alkynyl" refers to a monovalent unsaturated hydrocarbon group which may be linear, cyclic or branched and which has at least one, and typically 1, 2 or 3, carbon-carbon triple bonds. Unless otherwise defined, such alkynyl groups typically contain from 2 to 10 carbon atoms. Representative alkynyl groups include, by way of example, ethynyl, n-propynyl, n-but-2-ynyl, n-hex-3-ynyl, and the like.

"Aryl" refers to a polyunsaturated, aromatic hydrocarbon group having a single ring (i.e., phenyl) or multiple rings which are fused together (i.e., naphthalene) or linked covalently. Unless otherwise defined, such aryl groups typically contain from 6 to 10 carbon ring atoms. Representative aryl groups include, by way of example, phenyl and naphthalene-1-yl, naphthalene-2-yl, biphenyl and the like.

"Arylene" refers to a divalent aromatic hydrocarbon having a single ring (i.e., phenylene) or fused rings (i.e., naphthalenediyl). Unless otherwise defined, such arylene groups typically contain from 6 to 10 carbon ring atoms. Representative arylene groups include, by way of example, 1,2-phenylene, 1,3-phenylene, 1,4-phenylene, naphthalene-1,5-diyl, naphthalene-2,7-diyl, and the like.

"Aralkyl" refers to an aryl substituted alkyl group. Representative aralkyl groups include benzyl.

"Compound" refers to a specific molecule and includes its enantiomers, diastereomers, polymorphs and salts thereof.

"Condensation" refers to a reaction in which two or more molecules are covalently joined. Likewise, condensation products are the products formed by the condensation reaction.

"Cycloalkyl" refers to a monovalent saturated carbocyclic hydrocarbon group having a single ring or fused rings. Unless otherwise defined, such cycloalkyl groups typically contain from 3 to 10 carbon atoms. Representative cycloalkyl groups include, by way of example, cyclopropyl, cyclobutyl, cyclopentyl, cyclohexyl, and the like.

"Halo" or "halogen" refers to fluoro-(—F), chloro-(—Cl), bromo-(—Br), and iodo-(—I).

"Heteroatom" refers to nitrogen, oxygen, silicon, or sulfur.

"Heterocyclyl" refers to a saturated or unsaturated non-aromatic group containing at least one heteroatom. "Heteroaryl" refers to an aromatic group containing at least one heteroatom. Each heterocyclyl and heteroaryl can be attached at any available ring carbon or heteroatom. Each heterocyclyl and heteroaryl may have one or more rings. When multiple rings are present, they can be fused together or linked covalently. Each heterocyclyl and heteroaryl must contain at least one heteroatom (typically 1 to 5 heteroatoms) selected from nitrogen, oxygen or sulfur. Preferably, these groups contain 0-3 nitrogen atoms, 0-1 sulfur atoms and 0-1 oxygen atoms. Examples of saturated and unsaturated heterocyclyl groups include pyrrolidine, imidazolidine, pyrazolidine, piperidine, 1,4-dioxane, morpholine, thiomorpholine, piperazine, 3-pyrroline and the like. Examples of unsaturated and aromatic heterocycyl groups include pyrrole, imidazole, thiazole, oxazole, furan, thiophene, triazole, tetrazole, oxadiazole, pyrazole, isoxazole, isothiazole, pyridine, pyrazine, pyridazine, pyrimidine, triazine, indole, benzofuran, benzothiophene, benzimidazole, benzopyrazole, benzthiazole, quinoline, isoquinoline, quinazoline, quinoxaline and the like. Heterocyclyl and heteroaryl groups can be unsubstituted or substituted. For substituted groups, the substitution may be on a carbon or heteroatom. For example, when the substitution is =O, the resulting group may have either a carbonyl (—C(O)—) or a N-oxide (—N(O)—).

Suitable substituents for substituted alkyl, substituted alkenyl, substituted alkynyl and substituted cycloalkyl include-halogen, —OR', —NR'R", —SR', —SiR'R"R'", —OC(O)R', —C(O)R', —CO₂R', —CONR'R", —OC(O)NR'R", —NR"C(O)R', —NR'—C(O)NR"R'", —NR"C(O)₂R', —S(O)R', —S(O)₂R', —S(O)₂NR'R", —NR'S(O)₂R", —CN, oxo (=O or —O—) and —NO₂ in a number ranging from zero to (2 m'+1), where m' is the total number of carbon atoms in such radical.

Suitable substituents for substituted aryl and substituted heteroaryl include -halogen, unsubstituted or substituted alkyl, unsubstituted or substituted alkenyl, unsubstituted or substituted alkynyl, unsubstituted or substituted cycloalkyl, —OR', oxo (=O or —O), —OC(O)R', —NR'R", —SR', —R', —CN, —NO₂, —CO₂R', —CONR'R", —C(O)R', —OC(O)NR'R", —NR"C(O)R', —NR"C(O)₂R', —NR'—C(O)NR"R'", —NH—C(NH₂)=NH, —NR'C(NH₂)=NH, —NH—C(NH₂)=NR', —S(O)R', —S(O)₂R', —S(O)₂NR'R", —NR'S(O)₂R" and —N₃ in a number ranging from zero to the total number of open valences on the aromatic ring system.

Suitable substituents for substituted heterocyclyl include halogen, unsubstituted or substituted alkyl, unsubstituted or substituted alkenyl, unsubstituted or substituted alkynyl, unsubstituted or substituted cycloalkyl, —OR', oxo (=O or —O), —OC(O)R', —NR'R", —SR', —R', —CN, —NO$_2$, —OC(O)NR'R", —NR"C(O)R', —NR"C(O)$_2$R', —NR'—C(O)NR"R''', —NH—C(NH$_2$)=NH, —NR'C(NH$_2$)=NH, —NH—C(NH$_2$)=NR', —S(O)R', —S(O)$_2$NR'R", —NR'S(O)$_2$R" and —N$_3$ in a number ranging from zero to the total number of open valences on the aromatic ring system.

As used above, R', R" and R''' each independently refer to a variety of groups including hydrogen, halogen, unsubstituted or substituted C$_{1-8}$ alkyl, unsubstituted or substituted C$_{3-6}$ cycloalkyl, unsubstituted or substituted C$_{2-8}$ alkenyl, unsubstituted or substituted C$_{2-8}$ alkynyl, unsubstituted or substituted aryl, unsubstituted or substituted heteroaryl, unsubstituted or substituted heterocyclyl. Preferably, R', R" and R''' independently refer to a variety of groups selected from the group consisting of hydrogen, unsubstituted C$_{1-8}$ alkyl, unsubstituted heteroalkyl, unsubstituted aryl, aryl substituted with 1-3 halogens, unsubstituted C$_{1-8}$ alkyl, unsubstituted C$_{1-8}$ alkoxy, unsubstituted C$_{1-8}$ thioalkoxy groups, or unsubstituted aryl-C$_{1-4}$ alkyl groups. When R' and R" are attached to the same nitrogen atom, they can be combined with the nitrogen atom to form a 3-, 4-, 5-, 6-, or 7-membered ring (for example, —NR'R" includes 1-pyrrolidinyl and 4-morpholinyl).

Alternatively, two of the substituents on adjacent atoms of the aryl, heteroaryl or heterocycyl ring may optionally be replaced with a substituent of the formula -T-C(O)—(CH$_2$)$_q$—U—, wherein T and U are independently —NR'—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH$_2$)$_r$—B—, wherein A and B are independently —CH$_2$—, —O—, —NR'—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted C$_{1-6}$ alkyl.

"Pharmaceutically acceptable" carrier, diluent, or excipient is a carrier, diluent, or excipient compatible with the other ingredients of the formulation and not deleterious to the recipient thereof.

"Pharmaceutically-acceptable salt" refers to a salt which is acceptable for administration to a patient, such as a mammal (e.g., salts having acceptable mammalian safety for a given dosage regime). Such salts can be derived from pharmaceutically-acceptable inorganic or organic bases and from pharmaceutically-acceptable inorganic or organic acids, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary, tertiary and quaternary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Salts derived from pharmaceutically-acceptable acids include acetic, ascorbic, benzenesulfonic, benzoic, camphosulfonic, citric, ethanesulfonic, fumaric, gluconic, glucoronic, glutamic, hippuric, hydrobromic, hydrochloric, isethionic, lactic, lactobionic, maleic, malic, mandelic, methanesulfonic, mucic, naphthalenesulfonic, nicotinic, nitric, pamoic, pantothenic, phosphoric, succinic, sulfuric, tartaric, p-toluenesulfonic and the like.

"Salt thereof" refers to a compound formed when the hydrogen of an acid is replaced by a cation, such as a metal cation or an organic cation. Preferably, the salt is a pharmaceutically-acceptable salt, although this is not required for salts of intermediate compounds which are not intended for administration to a patient.

"Substituted" refers to a group that is bonded to a parent molecule or group. Thus, a benzene ring having a methyl substituent is a methyl-substituted benzene. Similarly, a benzene ring having 5 hydrogen substituents would be an unsubstituted phenyl group when bonded to a parent molecule.

"Therapeutically effective amount" refers to an amount of a compound, material, or composition including a compound of the present invention that is effective for producing a desired therapeutic effect by treating cancer when administered to a patient in need of treatment.

"Treating" or "treatment" refer to the administration of a composition to a patient, such as a mammal (particularly a human or a companion animal), having a disease or medical condition (such as cancer) which includes: (a) ameliorating the disease or medical condition, i.e., eliminating or causing regression of the disease or medical condition in a patient by preventing the conversion of pre-malignant cancer cells to their invasive counterparts; (b) suppressing the disease or medical condition, i.e., slowing or arresting the spread of the cancer in a patient; or (c) alleviating the symptoms of the disease or medical condition in a patient.

"Structure-activity relationship" (SAR) refers to the way in which altering the molecular structure of a compound alters its interaction with a receptor.

Modulators

The present invention provides modulators for use in the treatment of cancer. These compounds can serve as modulators of SDF-1 and I-TAC by binding with the CCXCKR2 receptor. Modulators (I) may also serve as modulators against other chemokine receptors. The chemokine family of peptides is defined on the basis of sequence homology and on the presence of variations on a conserved cysteine motif. Schall (1996) Cytokine 3:165-183; and Oppenheim et al. (1991) Annu. Rev. Immunol. 9:617-648. Chemokines display a range of in vitro and in vivo functions ranging from proinflammatory activities on a range of cell types to proliferative regulatory activities. To date several chemokine receptors have been described. See, for e.g., Neote et al. (1993) Cell 72:415-425; Ponath et al. (1996) J. Exp. Med. 183:2437-2448; and Power et al. (1995) J. Biol. Chem. 270:19495-19500.

In one embodiment, the modulators of the present invention have the general structure (I):

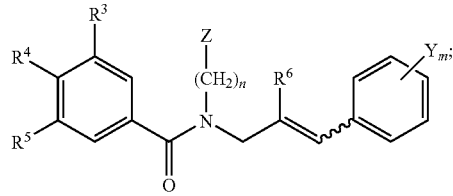

where where m is an integer from 1 to 5;

each Y is independently selected from the group consisting of hydrogen, halogen, —CN, —NO₂, —OH, —OR', —C(O)R', —CO₂R', —O(CO)R', —C(O)NR'R", —OC(O)NR'R", —SR, —SOR', —SO₂R', —SO₂NR'R", —NR'R", —NR'C(O)R", —NR'C(O)₂R", —NRSO₂R", —NR'(CO)NR"R'", unsubstituted or substituted $C_{1-8}$ alkyl, unsubstituted or substituted $C_{2-8}$ alkenyl, unsubstituted or substituted $C_{2-8}$ alkynyl, unsubstituted or substituted $C_{3-8}$ cycloalkyl, unsubstituted or substituted $C_{6-10}$ aryl, unsubstituted or substituted 5- to 10-membered heteroaryl, and unsubstituted or substituted 3- to 10-membered heterocyclyl;

where each R', R" and R'" are independently hydrogen, halogen, unsubstituted or substituted $C_{1-8}$ alkyl, unsubstituted or substituted $C_{6-10}$ aryl, unsubstituted or substituted 5- to 10-membered heteroaryl, and unsubstituted or substituted 3- to 10-membered heterocyclyl;

n is 0, 1, 2 or 3;

Z is —CHR¹R²—, —OR¹, or —NR¹R²;

R¹ and R² are each independently alkyl or hydrogen, or Z in combination with R¹ and R² form a substituted or unsubstituted 5- to 8-membered ring comprising at least one nitrogen and 0 to 3 additional heteroatoms;

R⁶ is alkyl, hydrogen, or halogen; and

R³, R⁴, and R⁵ are each independently selected from the group consisting of hydrogen, halogen, —CN, —NO₂, —OH, —OR', —C(O)R', —CO₂R', —O(CO)R', —C(O)NR'R", —OC(O)NR'R", —SR', —SOR', —SO₂R', —SO₂NR'R", —NR'R", —NR'C(O)R", —NR'C(O)₂R", —NR'SO₂R", —NR'(CO)NR"R'", unsubstituted or substituted $C_{1-8}$ alkyl, unsubstituted or substituted $C_{2-8}$ alkenyl, unsubstituted or substituted $C_{2-8}$ alkynyl, unsubstituted or substituted $C_{3-8}$ cycloalkyl, and unsubstituted or substituted 3- to 10-membered heterocyclyl;

or any two of R³, R⁴, and R⁵, together with the atoms which they substituted, form unsubstituted or substituted 3- to 10-membered heterocyclyl.

Modulators of the present invention are able to displace at least 50% of either of the chemokines SDF-1 or I-TAC from the CCXCKR2 receptor at concentrations at or below 1.1 micromolar (μM) and more preferably at concentrations at or below 300 nanomolar (nM). At present, especially preferred compounds can displace at least 50% of the SDF-1 or I-TAC from the CCXCKR2 receptor at concentrations at or below 200 nM.

The wavy bond connecting the olefin to the substituted phenyl ring signifies that the ring may be either cis or trans to R⁶. In a preferred embodiment, n is 1, 2, or 3. In another preferred embodiment, n is 2 or 3. In a further preferred embodiment, n is 3.

Known Compounds

The following compounds are known, but not as CCX-CKR2 modulators:

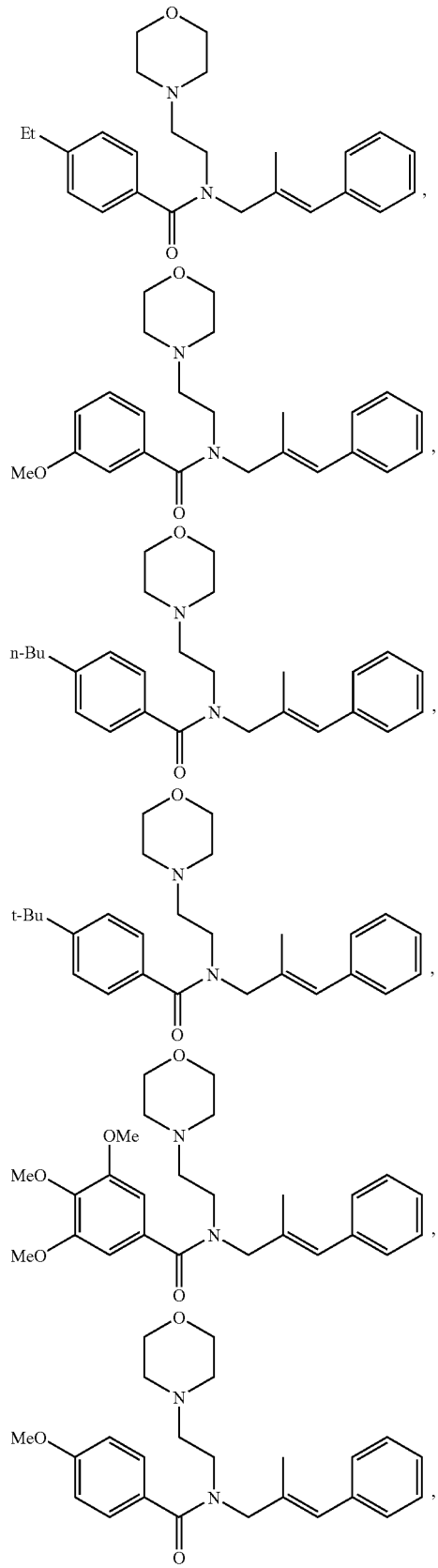

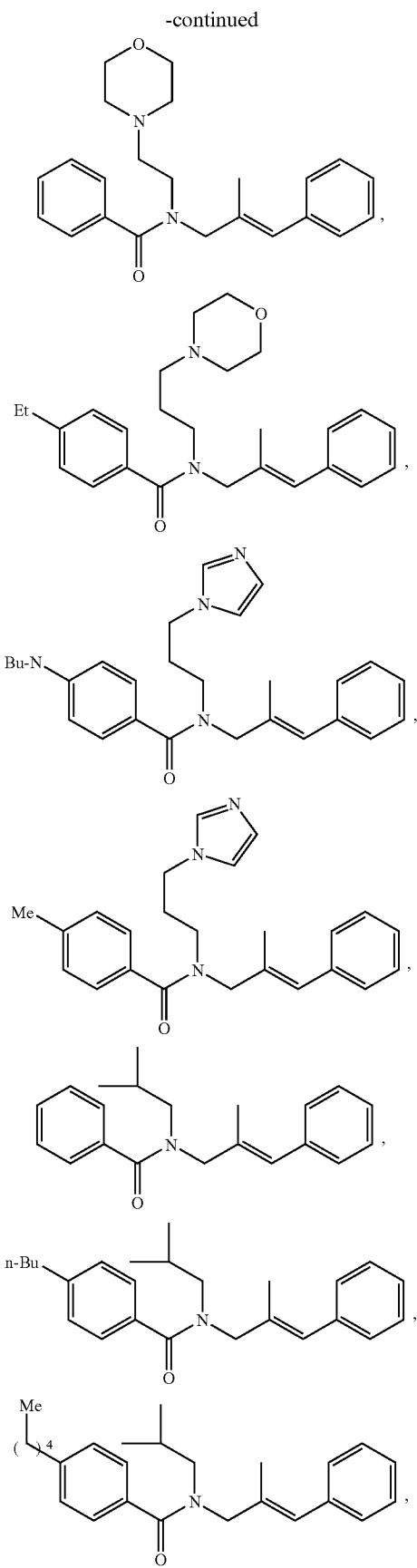

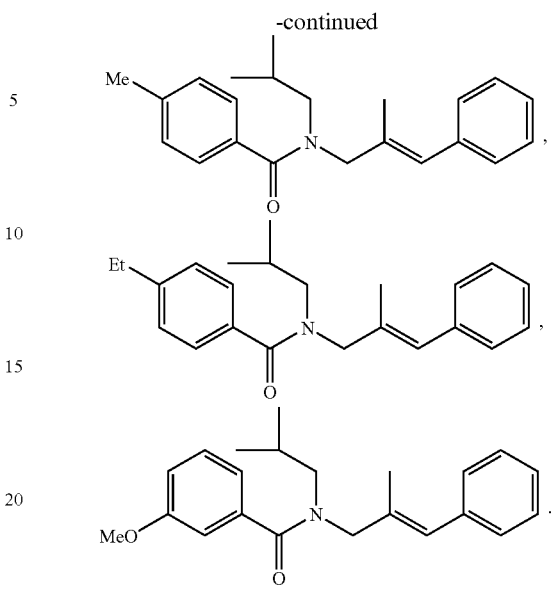

These compounds are excluded from the modulators (I) of the present invention.

Alternatively, modulators (I) of the present invention may have one or more the following provisos:

If Z is —$NR^1R^2$ and $R^1$ and $R^2$ together with Z form a morpholinyl group, then n is 3, and at least one of $R^3$, $R^4$, and $R^5$ is hydroxy, alkoxy, or aryloxy; or if n is 1 and Z is —$CHR^1R^2$, then $R^1$ and $R^2$ in combination is not —$CH_2CH_2NCH_2CH_2$—; or if n is 3 and Z is —$NR^1R^2$, then $R^1$ and $R^2$ in combination is not —CHNCHCH—; or if $R^1$ together with $R^2$ is —$CH(CH_3)(CH_2)_4$—, then Z is —CH—; or if $R^5$ is t-butyl, then $R^3$ is hydrogen; or if $R^4$ and $R^5$ together form a 5-membered ring, then at least one of the atoms bonded to the phenyl ring is carbon.

If if n=1 and Z is alkyl-$CHR^1R^2$, where $R^1$ and $R^2$ are each methyl, then neither $R^3$ or $R^5$ is can be alkyl; alternatively $R^3$, $R^4$ or $R^5$ can not each simultaneously be hydrogen; alternatively $R^4$ can not be methyl.

Preferred Substituents $R^6$ is preferably hydrogen, halogen or $C_{1-8}$ alkyl, more preferably methyl.

$R^3$, $R^4$, and $R^5$ are preferably each independently selected from the group consisting of hydrogen, —OR', and substituted or unsubstituted $C_{1-8}$ alkyl. More preferably $R^3$, $R^4$, and $R^5$ are each independently selected from the group consisting of hydrogen and —OR', where R' is substituted $C_{1-8}$ alkyl.

In an alternate preferred embodiment, $R^4$ and $R^5$ together with the atoms which they substitute may form a ring selected from the group consisting of substituted or unsubstituted 3- to 10-membered heterocyclyl. More preferably, $R^4$ and $R^5$ together with the atom which they substitute form substituted or unsubstituted 5- to 6-membered heterocyclyl containing 1 to 2 oxygen atoms.

Z is preferably —$CHR^1R^2$ or —$NR^1R^2$.

In one preferred embodiment, Z is —$CHR^1R^2$, where $R^1$ and $R^2$ together with Z form $C_{3-10}$ cycloalkyl with 0 to 3 substituents selected from the group consisting of halogen, —CN, —$NO_2$, —OH, —OR', —C(O)R', —$CO_2$R', —O(CO)R', —C(O)NR'R'', —OC(O)NR'R'', —SR', —SOR', —$SO_2$R', —$SO_2$NR'R'', —NR'R'', —NR'C(O)R'', —NR'C(O)$_2$R'', —NR'$SO_2$R'', —NR'(CO)NR''R''', unsubstituted or substituted $C_{1-8}$ alkyl, unsubstituted or substituted $C_{2-8}$ alkenyl, unsubstituted or substituted $C_{2-8}$ alkynyl, unsubstituted or substituted $C_{3-8}$ cycloalkyl, unsubstituted or substituted $C_{6-10}$ aryl, unsubstituted or substituted 5- to 10-membered heteroaryl, and unsubstituted or substituted 3- to 10-membered heterocyclyl.

In another preferred embodiment, $R^1$ and $R^2$ together with Z form a 3- to 10-membered heterocyclyl with 0 to 3 substituents selected from the group consisting of halogen, —OR, substituted or unsubstituted $C_{1-8}$ alkyl, substituted or unsubstituted $C_{1-8}$ alkenyl, substituted or unsubstituted $C_{1-8}$ alkynyl, substituted or unsubstituted $C_{6-10}$ aryl, substituted or unsubstituted 3- to 10-membered heterocycyl. More preferably, Z in combination with $R^1$ and $R^2$ is selected from the group consisting of substituted or unsubstituted morpholinyl, substituted or unsubstituted pyrrolidinyl, substituted or unsubstituted piperidinyl, and substituted or unsubstituted piperazinyl.

In other preferred embodiments, Z is a substituted or unsubstituted group of the formulae:

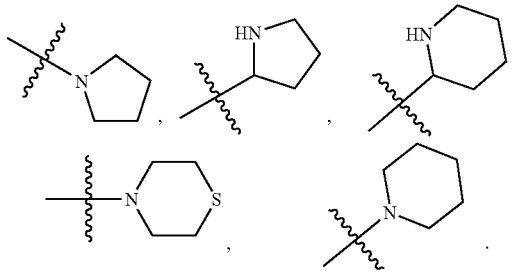

Most preferably, Z is a substituted or unsubstituted group of the formula:

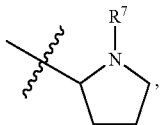

where $R^7$ is selected from the group consisting of hydrogen, —C(O)R', —CO$_2$R', —C(O)NR'R", —SO$_2$R', unsubstituted or substituted $C_{1-10}$ alkyl, unsubstituted or substituted $C_{1-8}$ alkoxyl (including, for example, $C_{1-10}$ alkoxyl alkoxyl, such as —CH2-CH$_2$OCH2-CH$_2$-OCH$_3$), unsubstituted or substituted $C_{2-10}$ alkenyl, unsubstituted or substituted $C_{2-10}$ alkynyl, unsubstituted or substituted $C_{3-10}$ cycloalkyl, unsubstituted or substituted $C_{6-10}$ aryl, unsubstituted or substituted 5- to 10-membered heteroaryl, and unsubstituted or substituted 3- to 10-membered heterocyclyl.

$R^7$ is most preferably substituted or unsubstituted $C_{1-10}$ alkyl, substituted or unsubstituted $C_{1-10}$ alkoxy, or substituted or unsubstituted $C_{3-10}$ cycloalkyl.

n is preferably 1, 2, or 3.

m is preferably 0, 1 or 2.

When present, Y is preferably halogen.

A modulator having the structure (II) or a diastereomer, enantiomer or pharmaceutically acceptable salts thereof:
  where each Y is independently hydrogen or halogen;
  $R^3$, $R^4$, and $R^5$ are each independently selected from the group consisting of hydrogen, halogen, and —OR'; or any two of $R^3$, $R^4$, and $R^5$, together with the atoms which they substituted, form unsubstituted or substituted 3- to 10-membered heterocyclyl; and $R^7$ is selected from the group consisting of hydrogen, —C(O)R', —CO$_2$R', —C(O)NR'R", —SO$_2$R', unsubstituted or substituted $C_{1-10}$ alkyl, unsubstituted or substituted $C_{1-8}$ alkoxyl (including, for example, $C_{1-10}$ alkoxyl alkoxyl, such as —CH—$_2$OCH$_2$OCH$_3$), unsubstituted or substituted $C_{2-10}$ alkenyl, unsubstituted or substituted $C_{2-10}$ alkynyl, unsubstituted or substituted $C_{3-10}$ cycloalkyl, unsubstituted or substituted $C_{6-10}$ aryl, unsubstituted or substituted 5- to 10-membered heteroaryl, and unsubstituted or substituted 3- to 10-membered heterocyclyl.

Synthetic Methods

While many synthetic routes known to those of ordinary skill in the art may be used to synthesize the active compounds of the present invention, a general synthesis method is given below in Scheme A.

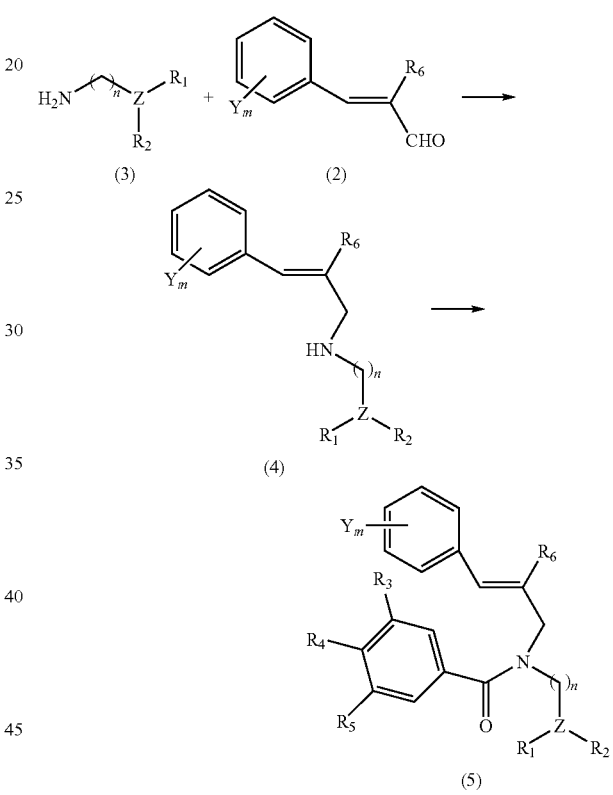

In Scheme I, aldehyde (2) undergoes a condensation reaction with primary amine (3) via reductive amination. Suitable primary amines are commercially available from Aldrich, Milwaukee, Wis., for example, or may be synthesized by chemical routes known to those of ordinary skill in the art.

The amination reaction may be carried out with a reducing agent in any suitable solvent, including, but not limited to tetrahydrofuran (THF), dichloromethane, or methanol to form the intermediate (4). Suitable reducing agents for the condensation reaction include, but are not limited to, sodium cyanoborohydride (as described in Mattson, et al., J. Org. Chem. 1990, 55, 2552 and Barney, et al., Tetrahedron Lett. 1990, 31, 5547); sodium triacethoxyborohydride (as described in Abdel-Magid, et al., Tetrahedron Lett. 1990, 31, 5595); sodium borohydride (as described in Gribble; Nutaitis Synthesis. 1987,709); iron pentacarbonyl and alcoholic KOH (as described in Watabane, et al., Tetrahedron Lett. 1974, 1879); and BH$_3$-pyridine (as described in Pelter, et al., J. Chem. Soc., Perkin Trans. 1, 1984, 717).

The transformation of intermediate (4) to compound (5) may be carried out in any suitable solvent, such as tetrahydrofuran or dichloromethane, with a suitably substituted acyl chloride in presence of a base. Tertiary amine bases are preferred. Especially preferred bases include triethylamine and Hunnings base.

Alternatively, the transformation of intermediate (4) to compound (5) can also be obtained with a suitable coupling reagent, such as propane phosphonic acid cyclic anhydride, O-(benzotriazol-1-yl)-N,N,N',N'-tetramethyluronium tetrafluoroborate, 1-ethyl-3-(3-dimethylbutylpropyl)carbodiimide or Dicyclohexyl-carbodiimide (as described in B. Neises and W. Steglich, Angew. Chem., Int. Ed. Engl., 17, 522, 1978), in the presence of a catalyst, such as 4-N,N-dimethylamino-pyridine, or in the presence of hydroxybenzotriazole (as described in K. Horiki, Synth. Commun., 7,251).

Pharmaceutical Compositions

Pharmaceutical compositions for administration of the claimed active compounds (or salts thereof) may be presented in a dosage unit form and may be prepared by any of the methods known in the art of pharmacy. Preferred methods include the step of combining the active compound, compounds, or salt thereof with one or more carrier that includes one or more accessory ingredient.

In one embodiment, pharmaceutical compositions are prepared by bringing an active compound or salt thereof into association with a liquid carrier, a finely divided solid carrier, or both. If desired, the composition may then be shaped into a product of the desired formulation. In the pharmaceutical composition, the active compound is included in a therapeutically effective amount.

Pharmaceutical compositions, including, but not limited to pharmaceutically-acceptable salts, containing the active compound may be in a form suitable for oral use, for example, as tablets, troches, lozenges, aqueous or oily suspensions, dispersible powders or granules, emulsions, hard or soft capsules, syrups, or elixirs. Compositions intended for oral use may be prepared according to any method known to the art for the manufacture of pharmaceutical compositions and such compositions may contain one or more agents selected from the group consisting of sweetening agents, flavoring agents, coloring agents, and preserving agents to provide pharmaceutically elegant and palatable preparations.

Tablets contain the active ingredient in admixture with non-toxic pharmaceutically acceptable excipients that are suitable for the manufacture of tablets. These excipients may include, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets may be uncoated or coated by known techniques to delay disintegration and absorption in the gastrointestinal tract, and thereby provide a sustained action over a longer period. For example, a time delay material such as glyceryl monostearate or glyceryl distearate may be employed. The tablet may also be coated by the techniques described in U.S. Pat. Nos. 4,256,108; 4,166,452; and 4,265,874 to form osmotic therapeutic tablets for controlled release.

Formulations for oral use may also be hard gelatin capsules, wherein the active ingredient is mixed with an inert solid diluent, for example, calcium carbonate, calcium phosphate, kaolin, or as soft gelatin capsules, wherein the active ingredient is mixed with water or an oil medium, for example peanut oil, liquid paraffin, or olive oil.

Aqueous suspensions may also contain the active compositions in a mixture with excipients suitable for the manufacture of aqueous suspensions. Such excipients are often referred to as suspending agents, dispersing agents, or wetting agents. Preferable suspending agents include, for example, sodium carboxymethylcellulose, methylcellulose, hydroxy-propylmethylcellulose, sodium alginate, polyvinylpyrrolidone, gum tragacanth, and gum acacia.

Preferable dispersing or wetting agents may be a naturally-occurring phosphatide, for example lecithin; condensation products of an alkylene oxide with fatty acids, for example polyoxyethylene stearate; condensation products of ethylene oxide with long chain aliphatic alcohols, for example heptadecaethyleneoxycetanol; condensation products of ethylene oxide with partial esters derived from fatty acids and a hexitol, such as polyoxyethylene sorbitol monooleate; or condensation products of ethylene oxide with partial esters derived from fatty acids and hexitol anhydrides, for example polyethylene sorbitan monooleate. The aqueous suspensions may also contain one or more preservatives, for example, ethyl or n-propyl p-hydroxybenzoate; one or more coloring agents; one or more flavoring agents; and one or more sweetening agents, such as sucrose or saccharin.

Oily suspensions may be formulated by suspending the active ingredient in a vegetable oil, such as arachis oil, olive oil, sesame oil, or coconut oil; or in a mineral oil, such as liquid paraffin. The oily suspensions may contain a thickening agent, for example beeswax, hard paraffin, or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in a mixture with a dispersing or wetting agent, a suspending agent, and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, such as gum acacia or gum tragacanth; naturally-occurring phosphatides, such as soy bean, lecithin, esters, and partial esters derived from fatty acids; hexitol anhydrides, such as sorbitan monooleate; and condensation products of the said partial esters with ethylene oxide, such as polyoxyethylene sorbitan monooleate. The emulsions may also contain sweetening and flavoring agents.

Syrups and elixirs may be formulated with sweetening agents, such as glycerol, propylene glycol, sorbitol or sucrose. Such formulations may also contain a demulcent, a preservative, flavoring, and coloring agents.

The pharmaceutical compositions of the invention may also be used in combined therapy to modulate chemokine receptor activity and thereby prevent and treat inflammatory and immunoregulatory disorders and diseases, including asthma and allergic diseases; as well as autoimmune pathologies such as rheumatoid arthritis, AIDS, and atherosclerosis, etc. For example, in the treatment or prevention of inflammation, the present compounds may be used in conjunction with an anti-inflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal anti-inflammatory agent, or a cytokine-suppressing anti-inflammatory agent, for example with a compound such as acetaminophen, aspirin, codene, fentanyl, ibuprofen, indomethacin, ketorolac, morphine, naproxen, phenacetin, piroxicam, a steroidal analgesic, sufentanyl, sunlindac, tenidap, and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxy-ephedrine; an antuitussive such as codeine, hydrocodone, caramiphen, carbetapentane, or dextramethorphan; a diuretic; and a sedating or non-sedating antihistamine.

Compounds of the present invention may be used in combination with other drugs that are used in the treatment/prevention/suppression or amelioration of the diseases or conditions for which compounds of the present invention are useful. Such other drugs may be administered, by a route and in an amount commonly used, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The pharmaceutical compositions may be in the form of an injectable aqueous or oleaginous suspension. This suspension may be formulated according to the known art using suitable dispersing or wetting agents and suspending agents, including those mentioned above. The injectable preparation may also be a sterile, injectable solution or suspension in a non-toxic parenterally-acceptable diluent or solvent, for example as a solution in 1,3-butane diol. Acceptable vehicles and solvents include water, Ringer's solution, and isotonic sodium chloride solution. In addition, sterile, fixed oils are conventionally employed as a solvent or suspending medium. For this purpose, any bland fixed oil may be employed including synthetic mono- or di-glycerides. In addition, fatty acids such as oleic acid find use in the preparation of injectables. The compositions of the present invention can be injected directly into a solid tumor, into tissue surrounding the solid tumor, or into a blood vessel vascularizing the solid tumor.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols.

For topical use, patches, creams, ointments, jellies, solutions, suspensions, and dispersions that contain one or more of the compounds of the present invention may be utilized. Topical application also includes mouth washes and gargles. The pharmaceutical compositions and methods of the present invention may further comprise other therapeutically active compounds that are used in the treatment of cancer.

In the treatment of cancer with the modulators of the present invention, an appropriate dosage level of the antagonist will generally be about 0.01 to 500 mg per kg patient body weight per day, which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day.

For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0,150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen that includes 1 to 4 dosages per day, preferably once or twice per day.

It will be understood, however, that the specific dose level and frequency of dosage for any particular patient may be varied and will depend upon a variety of factors. These factors include the activity of the specific compound employed, the metabolic stability and length of action of that compound, the age, body weight, general health, sex, diet, mode and time of administration, rate of excretion, drug combination, the severity of the particular condition, and the host undergoing therapy.

Methods of Blocking the CCXCKR2 Receptor

While not wishing to be bound by any particular theory, the compositions of the present invention are believed to provide a method of inhibiting the binding of SDF-1 and/or I-TAC to the CCXCKR2 receptor. SDF-1 is known to provide a target for interfering with the development or spread of cancer cells in a mammal, such as a human. As shown below in paragraphs 406-408, inhibition of the binding of I-TAG to the CCXCKR2 receptor prevents the formation of vascularized tumors. By contacting the compositions described above with a cancer cell that expresses the CCXCKR2 receptor, the invasive response that would otherwise trigger in the cancer cell can be reduced. Accordingly, the present invention is also directed to methods that are useful in the prevention and/or treatment of cancer, particularly solid tumor cancers, more particularly breast cancer.

As determined by radiolabeled SDF-1 binding and I-TAC displacement, CCXCKR2 was preferentially expressed in human transformed cells. Included in TABLE 1 are those tissue types in which CCXCKR2 was expressed (CCXCKR2$^+$) as well as those tissue types in which CCXCKR2 was not expressed (CCXCKR2).

TABLE 2

| CCXCKR2$^+$ | CCXCKR2$^-$ |
|---|---|
| Human Cervical Adenocarcinoma | Normal Mouse Adult Progenitors (c-kit+ & CD34+ BM derived) |
| Human Adenocarcinoma, Mammary Gland | Human Acute Lymphoblastic Leukemia, T Cell |
| Human Burkitt's Lymphoma, B Lymphocyte | Normal Murine Bone Marrow |
| Human Glioblastoma Multiforme, Brain | Normal Murine Thymus |
| Human Carcinoma, Prostate | Normal Murine Lung |
| Murine Lymphoblastic Leukemia, B Lymphocyte | Normal Murine Spleen |
| Murine Mammary Gland Tumor | Normal Murine Liver |
| Normal Murine Fetal Liver | Normal Murine PBL |
| Normal Mouse Brain | Normal Human PBL |
| Normal Mouse Kidney | Normal Murine Heart |
| | Normal Murine Pancreas |

In one embodiment, a preferred method of inhibiting the binding of the chemokines SDF-1 and/or I-TAC to a CCXCKR2 receptor includes contacting one or more of the previously mentioned compounds with a cell that expresses the CCXCKR2 receptor for a time sufficient to inhibit the binding of these chemokines to the CCXCKR2 receptor.

Methods of Treating Cancer

The present invention also provides a method of treating cancer. A preferred method of treating cancer, includes administering a therapeutically effective amount of one or more of the previously mentioned compounds (or salts thereof) to a cancer patient for a time sufficient to treat the cancer.

For treatment, the compositions of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

Standard in vivo assays demonstrating that the compositions of the present invention are useful for treating cancer include those described in Bertolini, F., et al., *Endostatin, an antiangiogenic drug, induces tumor stabilization after chemotherapy or anti-CD20 therapy in a NOD/SCID mouse model of human high-grade non-Hodgkin lymphoma*. Blood, No. 1, Vol. 96, pp. 282-87 (1 Jul. 2000); Pengnian, L., *Anti-angiogenic gene therapy targeting the endothelium-specific receptor tyrosine kinase Tie2*. Proc. Natl. Acad. Sci. USA, Vol. 95, pp. 8829-34 (July 1998); and Pulaski, B. Cooperativity of *Staphylococcal aureus Enterotoxin B Superantigen, Major Histocompatibility Complex Class II, and CD80 for Immunotherapy of Advanced Spontaneous Metastases in a Clinically Relevant Postoperative Mouse Breast Cancer Model*. Cancer Research, Vol. 60, pp. 2710-15 (May 15, 2000).

The preceding description does not limit the scope of the invention to the described embodiments, but rather enables a person of ordinary skill in the art of organic chemistry and pharmacology to make and use the invention. Similarly, the examples below are not to be construed as limiting the scope of the appended claims or their equivalents, and are provided solely for illustration. It is to be understood that numerous variations can be made to the compositions and methods below, which lie within the scope of the appended claims and their equivalents.

EXAMPLES

Example 1

Synthesis of (2-Methyl-3-phenyl-allyl)-[2-(1-methyl-pyrrolidin-2-yl)-ethyl]-amine

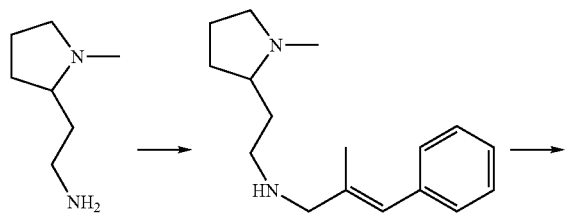

-continued

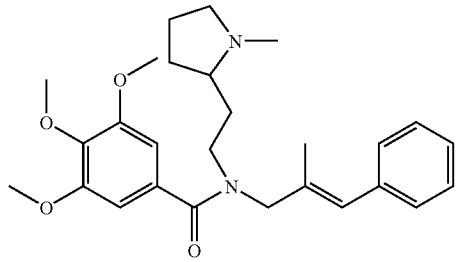

0.5 g of 2-(1-methyl-prrolidin-2-yl)-ethylamine (3.89 mmol) and 0.56 g of 2-methyl-3-phenyl-propenal were combined in 20 ml of anhydrous dichloromethane. The mixture was stirred under nitrogen on 5 g of magnesium sulfate. After two days, thin layer chromatography (TLC) using a 9:1:0.1 dichloromethane/methanol/ammonium hydroxide eluent showed an absence of the starting material. The reaction mixture was filtered, and the collected solid was washed with dichloromethane. The resultant organic layer was then concentrated under vacuum. Ten ml of dry methanol was added to the residual mixture under nitrogen and the solution was cooled to 0° C. To this mixture was added 0.14 g of sodium borohydride. TLC showed an absence of starting material after about 15 minutes. The reaction was then quenched with acetone (1 ml), and the solvent was removed by distillation. The mixture was partitioned between 5 ml of water in chloroform and the layers were separated. The aqueous layer was then extracted 3 times with 30 ml chloroform. The combined organic layer was washed with brine, dried over sodium sulfate, and filtered. Concentration under vacuum gave 0.78 g of a pale yellow solid. Yield: 77%.

LC-MSD, m/z for $C_{17}H_{26}N_2$ [M+H]+: 259, [M+2H]+: 260 $^1$H NMR (400 MHz, CDCl$_3$): δ1.4-1.6 (m, 2H), 1.67-1.82 (m, 3H), 1.9-2.0 (m, 3H), 2.02-2.20 (m, 2H), 2.38 (s, 3H), 2.58-2.79 (m, 2, H), 3.02-3.08 (m, 1H), 3.39 (s, 2H), 7.16-7.39 (m, 5H).

Example 2

3,4,5-Trimethoxy-N-(2-methyl-3-phenyl-allyl)-N-[2-(1-methyl-pyrrolidin-2-yl)-thyl]-benzamide 1-ethyl-3-(3-dimethylaminopropyl)carbodiimide hydrochloride 0.48 g (2.4 mmol) was added to 20 ml of anhydrous tetrahydrofuran. To this stirred solution, anhydrous triethylamine 0.23 ml (2.4 mmol) was added. After about 15 minutes, 3,4,5 trimethoxy benzoic acid 0.52 g (2.4 mmol) was added. The reaction mixture was stirred for 1 hour under nitrogen at room temperature. Then 1-hydroxybenzotriazole 0.24 g (1.76 mmol) was added and after an additional 30 minutes, (2-Methyl-3-phenyl-allyl)-[2-(1-methyl-pyrrolidin-2-yl)-ethyl]-amine 0.42 g (1.6 mmol) was added. After stirring overnight at room temperature, the reaction was quenched with 5 ml of water, and extracted with 20 ml of ethyl acetate. The combined organic layer was washed with brine, dried over magnesium sulfate, and concentrated under vacuum. The mixture was purified by elution from silica gel with 9:1 dichloromethane/methanol to give 0.38 g of a colorless oil. Yield: 53%.

LC-MSD, m/z for $C_{27}H_{36}N_2O_4$ [M+H]+: 453.2, [M+2H]+: 454.2. $^1$H NMR (400 MHz, CDCl$_3$): δ 1.44-2.22 (m, 10H), 2.35 (s, 3H), 2.92-3.18 (m, 2H), 3.2-3.4 (m, 2H), 3.60-3.66 (m, 1H), 3.8-4.02 (m, 9H), 4.2-4.4 (m, 2H), 6.45 (s, 1H), 6.63-6.71 (m, 2H), 7.21-7.35 (m, 5H).

Example 3

3,4-Bis-difluoromethoxy-3-methoxy-N-(2-methyl-3-phenyl-allyl)-N-[2-(1-methyl-pyrrolidin-2-yl)-ethyl]-benzamide

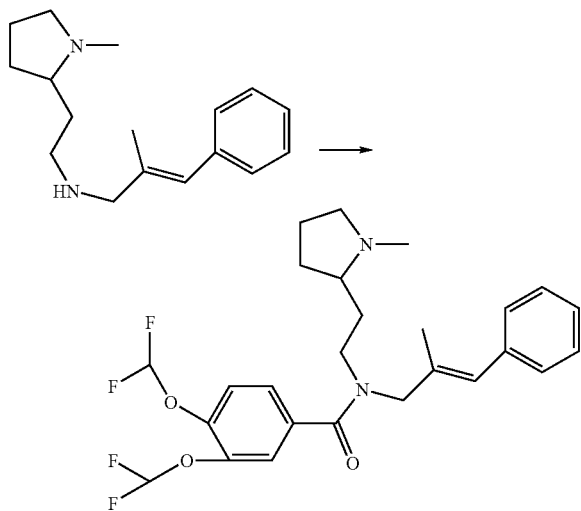

A mixture of (2-methyl-3-phenyl-allyl)-[2-(1-methyl-pyrrolidin-2-yl)-ethyl]-amine 0.1 g (0.4 mmol) and 3,4-bis-difluoromethoxy-benzoic acid 0.11 g (0.44 mmol) was dissolved in ethyl acetate 20 ml. Triethyl amine 0.16 ml was added to the mixture and stirred at room temperature for 20 minutes. A solution of 1-propanephosphonic acid cyclic anhydride (50% in ethyl acetate) 0.25 ml (0.44 mmol) was then added to the mixture, and was stirred overnight at room temperature. A saturated solution of sodium bicarbonate 5 ml was added to the mixture and stirred for 5 min. The layers were separated. The aqueous layer was extracted with ethyl acetate and combined with the organic layer. The organic layer was then dried, concentrated, and subjected to column chromatography on silica gel elution with dichloromethane 9.5:methanol 0.5, yielding the free amine.

The compound was dissolved in dichloromethane and cooled to 0° C. under nitrogen atmosphere and was transformed to the HCl salt with HCl-ether solution, yielding 34 mg of a white, hydroscopic compound. Yield: 7%.

LC-MSD, m/z for $C_{26}H_{30}F_4N_2O_3$ [M+H]+: 495.1 $^1$H NMR (400 MHz, CDCl$_3$): δ 1.7 (s, 3H), 1.9-2.5 (m, 5H), 2.7-3.0 (m, 3H), 3.1-3.5 (m, 1H), 3.3-3.5 (m, 1H), 3.6-4.0 (m, 6H), 6.2-6.4 (m, 1H), 6.5-6.8 (m, 2H), 7.1-7.5 (m, 8H).

Example 4

3,4,5-Triethoxy-N-(2-methyl-3-phenyl-allyl)-N-[2-(1-methyl-pyrrolidin-2-yl)-ethyl-benzamide

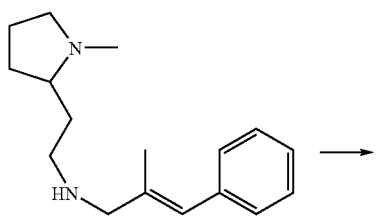

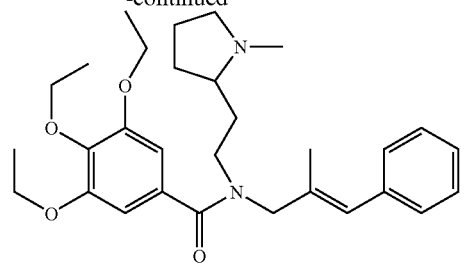

An analogous procedure to that discussed in Example 2 was used with 3,4,5-triethoxy carboxylic acid 0.22 g (0.8 mmol) and (2-Methyl-3-phenyl-allyl)-[2-(1-methyl-pyrrolidin-2-yl)-ethyl]-amine 0.1 g (0.38 mmol), 1-ethyl-3-(3-dimethylaminopropyl)carbodiimide hydrochloride 0.11 g (0.57 mmol), 1-hydrobenzotriazole 0.05 g (0.418 mmol), and triethylamine 0.08 ml. The resulting product was purified by preparatory high pressure liquid chromatography with a mobile phase gradient including 20% to 80% acetonitrile and 0.1% trifluoroacetic acid in water. 84.3 mg (0.13 mmol) of a white powder was obtained as a TFA salt. Yield: 30%.

LC-MSD, m/z for $C_{30}H_{42}N_2O_4$ [M+H]+: 495.3, [M+2H]+: 496.3.

Example 5

4-Difluoromethoxy-3-methoxy-N-(2-methyl-3-phenyl-allyl)-N-[2-(1-methyl-pyrrolidin-2-yl)-ethyl]-benzamide

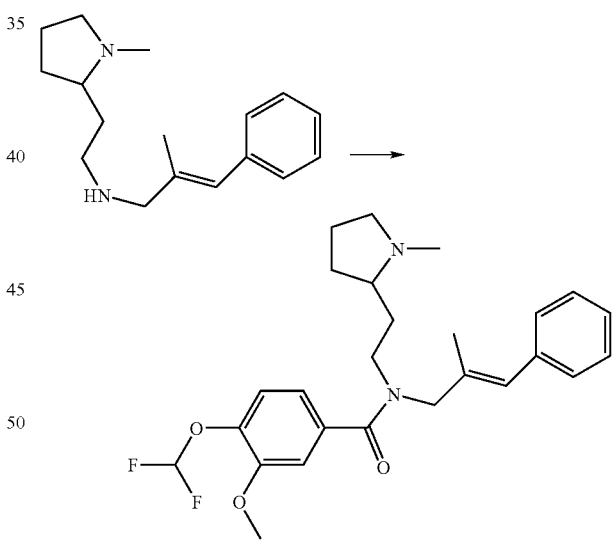

Experimental condition analogous to Example 3 were used with (2-Methyl-3-phenyl-allyl)-[2-(1-methyl-pyrrolidin-2-yl)-ethyl]-amine 0.1 g (0.4 mmol), 4-difluoromethoxy-3-methoxy-benzoic acid 0.93 g (0.44 mmol), 1-propanephosphonic acid cyclic anhydride (50% ethyl-acetate) 0.25 ml (0.4 mmol), and triethylamine 0.16 ml. The resulting free amine was transformed to 38 mg of a white, hydroscopic solid as a HCl salt. Yield: 8%.

Analytical $C^{18}$ HPLC using 20-95% acetonitrile gradient in 20 min, the compound elute at 14.504 minute LC-MSD, m/z for $C_{26}H_{32}N_2O_3F_2$ [M+H]+: 459.1, [M+2H]+: 460.1, [M+3H]: 461.2

Example 6

3,4-Dimethoxy-N-(2-methyl-3-phenyl-allyl)-N-[2-(1-methyl-pyrrolidine-2-yl)ethyl]-benzamide

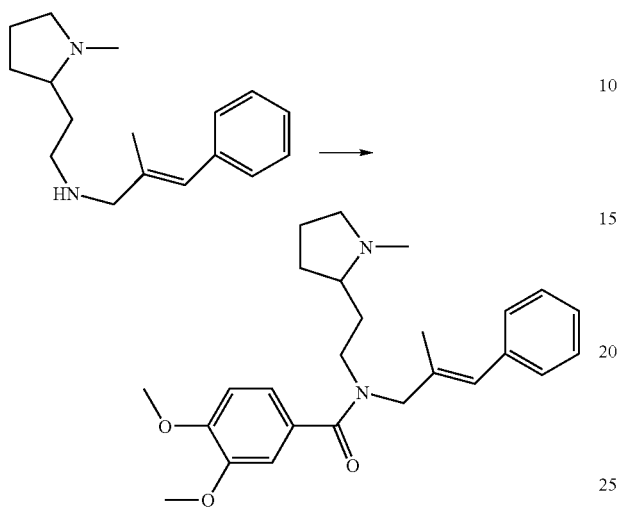

An analogous procedure to that discussed in Example 2 was used with 3,4-dimethoxycarboxylic acid 0.1 g (0.38 mmol) and (2-methyl-3-phenyl-allyl)-[2-(1-methyl-pyrrolidine-2-yl)-ethyl]-amine 0.1 g (0.38 mmol), 1-ethyl-3-(3-dimethylaminopropyl)carbodiimide hydrochloride 0.11 g (0.57 mmol), 1-hydroxybenzotriazole 0.05 g (0.41 mmol) and triethylamine 0.08 ml, to give 179 mg light yellow oil. Yield: 41%.

LC-MSD, m/z for $C_{28}H_{32}N_2O$ [M+H]+: 423.2.2, [M+2H]+:424.2

Example 7

3,5-Dimethoxy-N-(2-methyl-3-phenyl-allyl)-N-[2-(1-methyl-pyrrolidine-2-yl)ethyl]-benzamide

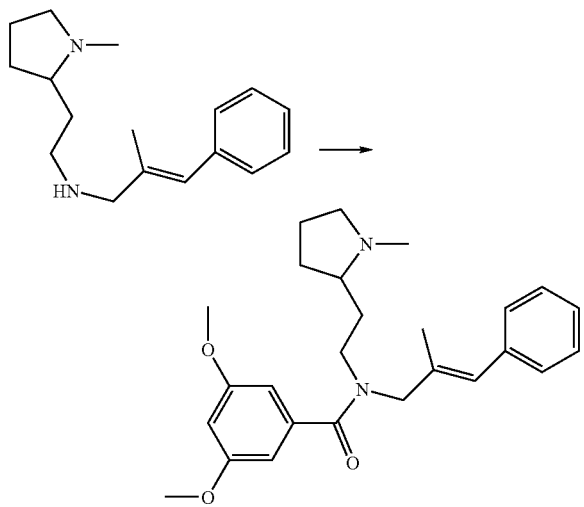

An analogous procedure to that discussed in Example 2 was used with 3,5-dimethoxycarboxylic acid 0.1 g (0.38 mmol) and (2-methyl-3-phenyl-allyl)-[2-(1-methyl-pyrrolidine-2-yl)-ethyl]-amine 0.1 g (0.38 mmol), 1-ethyl-3-(3-dimethylaminopropyl)carbodiimide hydrochloride 0.11 g (0.57 mmol), 1-hydroxybenzotriazole 0.05 g (0.41 mmol) and triethylamine 0.08 ml to give 140 mg of a light yellow oil. Yield: 33%.

LC-MSD, m/z for $C_{26}H_{34}N_2O_3$ [M+H]+: 423.2.2, [M+2H]+: 424.2 $^1$H NMR (400 MHz, CDCl$_3$): δ 1.44-2.00 (m, 14H), 2.25 (s, 3H), 2.92-3.08 (m, 1H), 3.2 (m, 1H), 3.6 (m, 1H), 3.7 (s, 3H), 3.8 (s, 2H), 6.3-6.5 (m, 3H), 7.1-7.4 (m, 5H)

Example 8

7-Methoxy-2,2-dimethyl-benzo[1,3]dioxole-5-carboxylic acid (2-methyl-3-phenyl-allyl)-[2-(1-methyl-pyrrolidin-2-yl)-ethyl]-amide

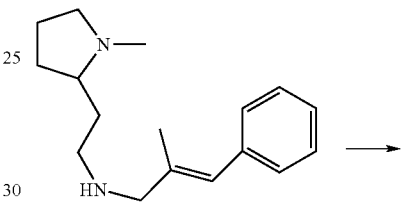

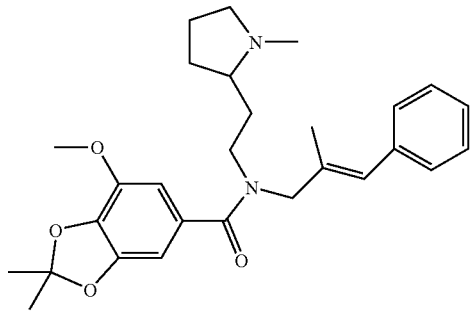

An analogous procedure to that discussed in Example 2 was used with 7-methoxy-2,2-dimethyl-benzo[1,3]dioxole-5-carboxylic acid 0.07 g (0.3 mmol) and (2-Methyl-3-phenyl-allyl)-[2-(1-methyl-pyrrolidin-2-yl)-ethyl]-amine 0.05 g (0.2 mmol), 1-ethyl-3-(3-dimethylaminopropyl)carbodiimide hydrochloride 0.56 g (0.28 mmol), 1-hydrobenzotriazole 0.05 g (0.2 mmol), and triethylamine 0.04 ml. The resulting product was purified by preparatory high pressure liquid chromatography with a mobile phase gradient including 20% to 70% acetonitrile and 0.1% trifluoroacetic acid in water. 16.3 mg (0.13 mmol) of white powder was obtained as a HCl salt. Yield: 4%.

Analytical $C^{18}$ HPLC using 20-95% acetonitrile gradient in 20 min, the compound elute at 15.196 minute LC-MSD, m/z for $C_{28}H_{36}N_2O_4$ [M+H]+: 465.2, [M+2H]+: 466.2.

Example 9

3,5-Dibromo-N-(2-methyl-3-phenyl-allyl)-N-[2-(1-methyl-pyrrolidin-2-yl)-ethyl]-benzamide

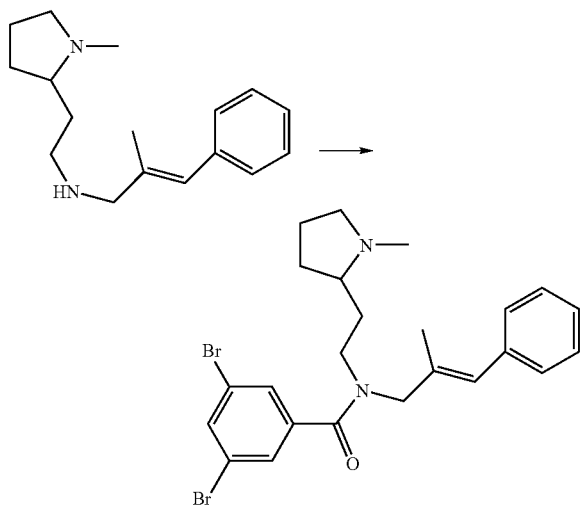

An analogous procedure to Example 2 was used with 3,5-dibromo-benzoic acid 0.16 g (0.38 mmol) and (2-methyl-3-phenyl-allyl)-[2-(1-methyl-pyrrolidine-2-yl)-ethyl]-amine 0.1 g (0.38 mmol), 1-ethyl-3-(3-dimethylaminopropyl)carbodiimide hydrochloride 0.11 g (0.57 mmol), 1-hydroxybenzotriazole 0.05 g (0.41 mmol) and triethylamine 0.08 ml. Reverse phase prep HPLC with a gradient 20-80% for the acetonitrile phase gavel 53 mg as a TFA salt. Yield: 63%.

LC-MSD, m/z for $C_{24}H_{28}N_2OBr_2$ [M+H]+: 519.3, [M+2H]+: 520.3, [M+3H]+: 521.3, [M+4H]+: 522.3, [M+5H]+: 523.3, [M+6H]+: 524.3

Example 10

3,5-Dimethyl-N-(2-methyl-3-phenyl-allyl)-N-[2-(1-methyl-pyrrolidin-2-yl)-ethyl]-benzamide

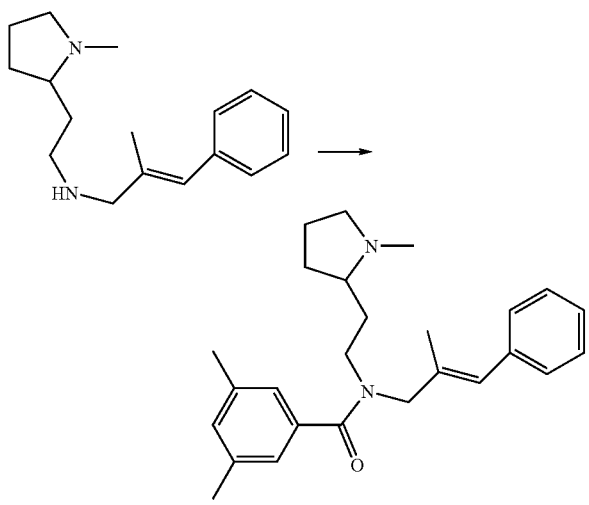

An analogous procedure to Example 2 was used with 3,5-dimethyl-benzoic acid 0.16 g (0.38 mmol) and (2-methyl-3-phenyl-allyl)-[2-(1-methyl-pyrrolidine-2-yl)-ethyl]-amine 0.1 g (0.38 mmol), 1-ethyl-3-(3-dimethylaminopropyl)carbodiimide hydrochloride 0.11 g (0.57 mmol), 1-hydroxybenzotriazole 0.05 g (0.41 mmol) and triethylamine 0.08 ml. Reverse phase prep HPLC with a gradient 20-80% for the acetonitrile with 0.1% trifluoroacetic acid phase gave 60 mg as a TFA salt. Yield: 32%.

LC-MSD, m/z for $C_{26}H_{34}N_2O$ [M+H]+: 391.5 [M+2H]+: 392.4

Example 11

4-Methoxy-3,5-dimethyl-N-(2-methyl-3-phenyl-allyl)-N-[2-(1-methyl-pyrrolidin-2-yl)-ethyl]-benzamide

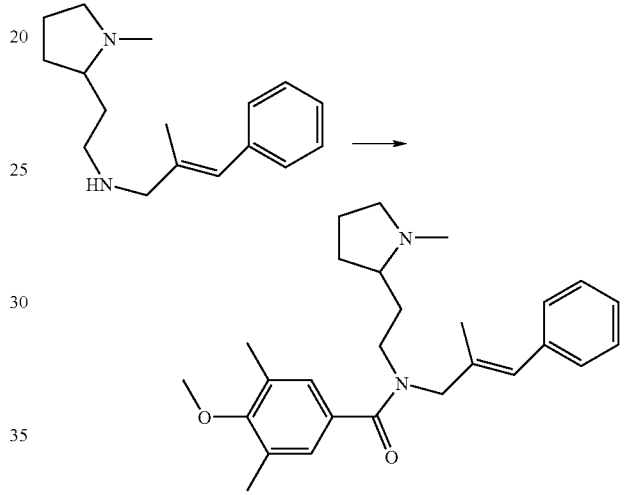

An analogous procedure to Example 2 was used with 4-methoxy-3,5-dimethyl-benzoic acid 0.108 g (0.58 mmol) and (2-methyl-3-phenyl-allyl)-[2-(1-methyl-pyrrolidine-2-yl)-ethyl]-amine 0.1 g (0.38 mmol), 1-ethyl-3-(3-dimethylaminopropyl)carbodiimide hydrochloride 0.11 g (0.57 mmol), 1-hydroxybenzotriazole 0.05 g (0.41 mmol) and triethylamine 0.08 ml. Reverse phase prep HPLC with a gradient 20-80% for the acetonitrile with 0.1% trifluoroacetic acid phase gave 45.4 mg as a TFA salt. Yield: 22%.

LC-MSD, m/z for $C_{27}H_{36}N_2O_2$ [M+H]+: 421.2 [M+2H]+: 422.2

Example 12

3,4-Dihydro-2H-benzo[b][1,4]dioxepine-7-carboxylic acid(2-methyl-3-phenyl-allyl)-2[-(1-methyl-pyrrolidine-2-yl)-ethyl]-amide

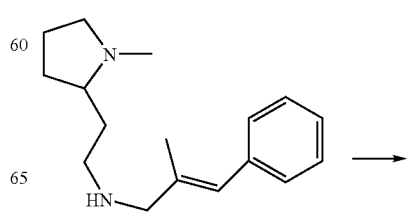

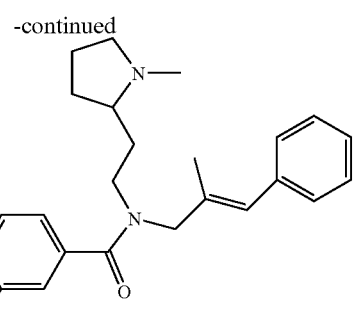

A mixture of (2-methyl-3-phenyl-allyl)-[2-(1-methyl-pyrrolidine-2-yl)-ethyl]-amine 0.1 g (0.38 mmol) and 0.08 ml (0.58 mmol) of triethylamine was stirred in 5 ml anhydrous dichloromethane at 0° C. under nitrogen. To this mixture was added 3,4-dihydro-2H-benzo[b][1,4]dioxepine-7-carbonyl chloride 0.098 g (0.456 mmol). To the reaction mixture was added 25 ml of ethyl acetate and 5 ml water. The organic layer was separated from aqueous, then dried with sodium sulfate. The organic layer was filtrated and evaporated under vacuum. Purification using flash chromatography, elution with ethyl acetate 9.5, methanol 0.5 and ammonium hydroxide 0.05, gave a brown oil.

LC-MSD, m/z for $C_{27}H_{34}N_2O_3$ [M+H]+: 435.2, [M+2H]+: 436.2.

Example 13

3,4,5-Trimethoxy-N-(2-methyl-3-phenyl-allyl)-N-(2-pyrrolidin-2-yl-ethyl)-benzamide Scheme 1: Preparation of 2-[2-(2-Methyl-3-phenyl-allylamino)-ethyl-pyrrolidine-1-carboxylic acid tert-butyl ester

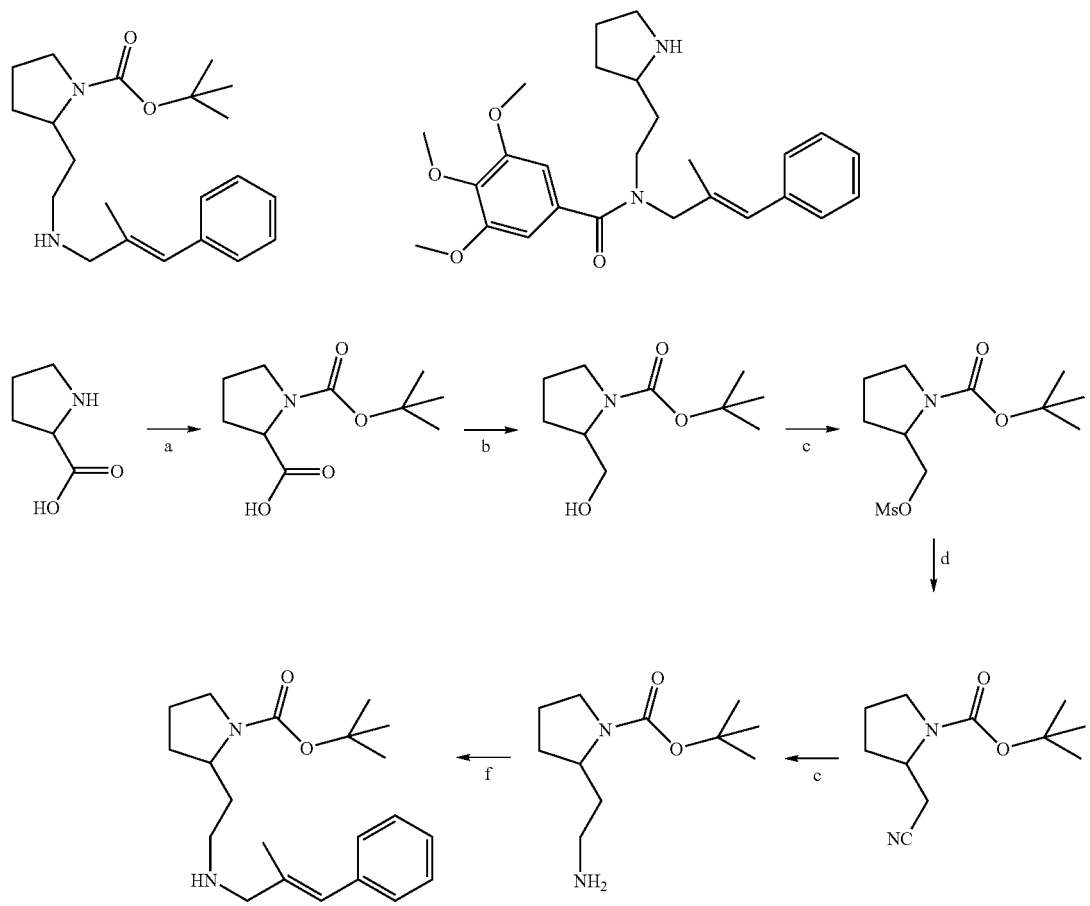

a: BOC-anhydride, NaOH, acetonitrile, 3 h, RT
b: Borane dimethylsulfide, THF, 14 h, RT
c: Methanesulfonylchloride, triethylamine, dichloromethane, 4 h, RT
d: Sodium cyanide, dimethylformamide, 5 h, RT
e: Raney nickel, ammonia gas in methanol, $H_2$ 2.5 kg pressure, 14 h
f: 1/ 1-methyl cinnamaldehyde, dichloromethane, 16 h, RT, $N_2$
  2/ Sodium borohydride, methanol, 30 minutes at 0° C.

To a solution of the compound 2-[2-(2-Methyl-3-phenyl-allylamino)-ethyl-pyrrolidine-1-carboxylic acid tert-butyl ester (prepared from racemic proline according to the scheme1), 0.6 g (2 mmol) and 3,4,5-trimethoxy benzoic acid 0.513 g (2.4 mmol) in dry dichloromethane 10 ml, triethyl amine 0.2 ml was added and stirred at room temperature for 20 min. Then was added O-(benzotriazole-1-yl)-N,N,N',N'-tetramethyl uranium tetrafluoroborate 1.3 g (4 mmol) at 0° C. The reaction mixture was stirred at room temperature overnight. The reaction mixture was diluted with DCM and was washed with 10% NaHCO$_3$ solution, water and brine, dried, concentrated and subjected to column chromatography silica gel using CHCl$_3$/MeOH as eluent to obtain 1 g of 2-{2-[(2-Methyl-3-phenyl-allyl)-3,4,5-trimethoxy-benzoyl)-amino]-ethyl}-pyrrolidine-1-carboxylic acid tert-butyl ester.

This compound was dissolved in 10 ml of dioxane and 6N HCl 10 ml was added to it. The reaction mixture was stirred at room temperature for 14 hr, basified with 10% NaOH solution and was extracted twice with ethyl acetate (15 ml). The organic layer was washed with water, brine, dried over anhydrous sodium sulfate, concentrated and purified by column chromatography over silica gel to obtain the free amine 0.35 g. The free amine 100 mg was converted to its hydrochloride salt using dry HCl in ether to yield 88 mg as a white solid. Yield: 39%.

LC-MSD, m/z for $C_{26}H_{34}N_2O_4$ [M+H]+: 439.3 $^1$H NMR (300 MHz, MeOD/D2O): δ 1.6-1.8 (m, 4H), 1.9-2.1 (m, 4H), 2.25 (m, 1H), 3.2 (m, 3H), 3.5-3.8 (m, 12H), 4.1 (s, 2H), 6.5 (s, 1H), 6.7-6.9 (m, 2H), 7.2-7.5 (m, 5H)

Example 14

N-[2-(1-Benzyl-pyrrolidin-2-yl)-ethyl]-3,4,5-trimethoxy-N-(2-methyl-3-phenyl-allyl)-benzamide

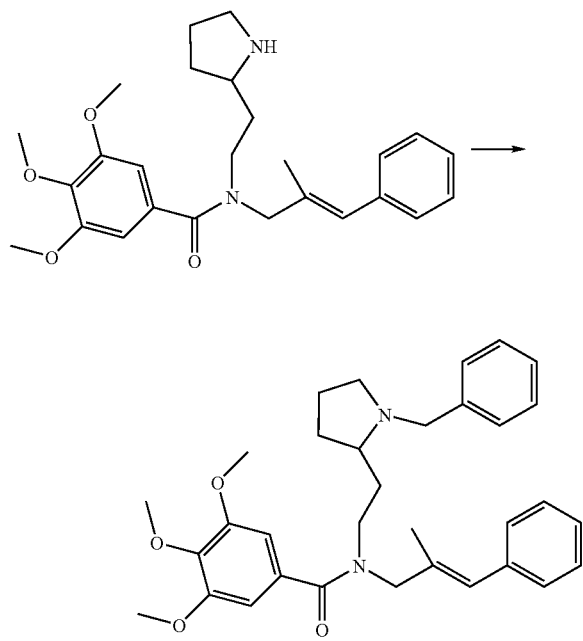

3,4,5-Trimethoxy-N-(2-methyl-3-phenyl-allyl)-N-(2-pyrrolidin-2-yl-ethyl)-benzamide 0.11 g (2.5 mmol) and freshly distilled benzaldehyde 0.026 g (2.5 mmol) was taken in 10 ml of dry methanol. Acetic acid 0.022 ml (3.7 mmol) was added at 0° C. The reaction mixture was stirred at room temperature for 30 min and sodium cyanoborohydride 0.023 g (3.7 mmol) was added at 0° C. The reaction mixture was gradually warmed to room temperature and stirred for 14 hr. The reaction mixture was concentrated, and the residue was diluted with water and extracted with chloroform (3×20 ml). Organic layer was washed with 10% NaHCO$_3$ solution, water and brine, dried over anhydrous sodium sulfate, concentrated and the residue was purified by column chromatography over silica gel to yield the pure desired compound. This was converted to its hydrochloride salt using dry HCl in ether to obtain 90 mg of product. Yield: 63%.

LC-MSD, m/z for $C_{33}H_{40}N_2O_4$ [M+H]+: 529.3 $^1$H NMR (300 MHz, MeOD/D2O): δ 1.8-2.2 (m, 10H), 2.5 (m, 1H), 3.4-3.6 (m, 4H), 3.7 (m, 1H), 3.8 (m, 9H), 4.0 (s, 3H), 4.2-4.5 (m, 2H), 4.7 (d, 1H), 6.25 (s, 1H), 6.8 (s, 2H), 7.2-7.6 (m, 10H).

Example 15

N-[2-(1-ethyl-pyrrolidin-2-yl)-ethyl]-3,4,5-trimethoxy-N-(2-methyl-3-phenyl-allyl)-benzamide

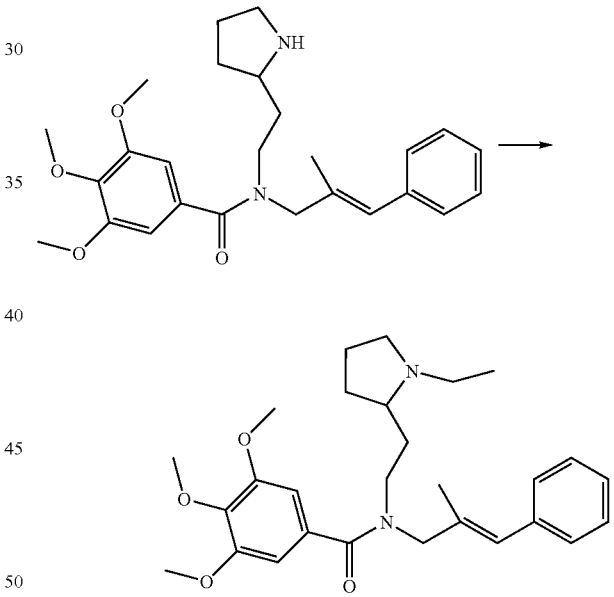

To a solution of 3,4,5-trimethoxy-N-(2-methyl-3-phenyl-allyl)-N-(2-pyrrolidin-2-yl-ethyl)-benzamide 0.1 g (2.28 mmol) in dry dichloromethane 5 ml, sodium bicarbonate 0.01 g (2.7 mmol) was added followed by ethyl bromide 0.037 g (3.4 mmol) at 0° C. The reaction mixture was stirred at room temperature for 14 hrs. Inorganics were filtered off and filtrate was concentrated. Crude material was subjected to column chromatography on silica gel, elution with chloroform-methanol to yield desired compound as a free amine. This was converted to its hydrochloride salt 42 mg as a yellow semi-solid.

LC-MSD, m/z for $C_{28}H_{38}N_2O_4$ [M+H]+: 467.4 $^1$H NMR (300 MHz, MeOD): δ 1.1-2.4 (m, 4H), 2.7 (s, 3H), 1.7-2.1 (m, 4H), 2.4-2.5 (m, 2H), 3.0-3.2 (m, 2H), 3.4-3.6 (m, 2H), 3.6-3.9) m, 10H), 4.1-4.2 (m, 2H), 6.4-7.5 (m, 8H).

Example 16

3,4,5-Trimethoxy-N-(2-methyl-3-phenyl-allyl)-N-(2-(S)-pyrrolidin-2-yl-ethyl)-benzamide washed with 10% sodium bicarbonate solution, water and brine, dried, concentrated and subjected to column chromatography (silica gel, n-hexane: ethylacetate as eluent) to yield 0.57 g 2-{2-[(2-methyl-3-phenyl-allyl)-3,4,5-trimethoxy-

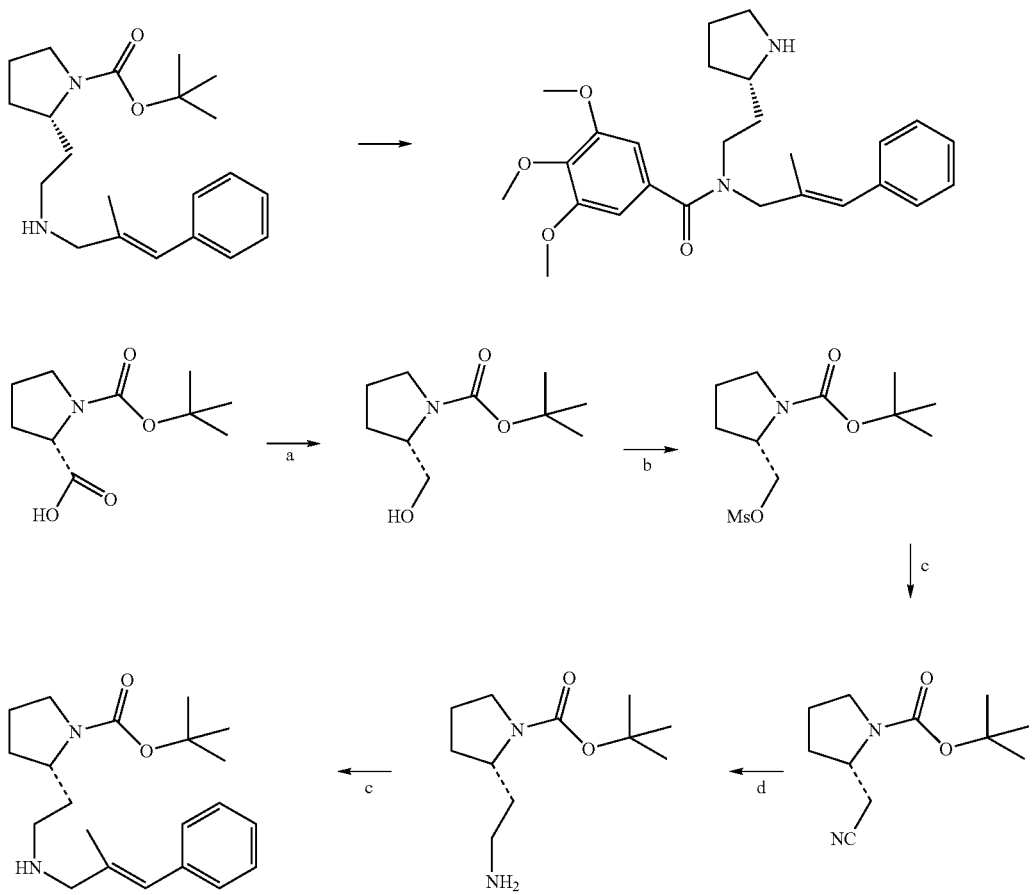

Scheme 2: Preparation of 2-[2-(2-Methyl-3-phenyl-allylamino)-ethyl-(S)-pyrrolidine-1-carboxylic acid tert-butyl ester a: Borane dimethylsulfide, THF, 14 h, RT
b: Methanesulfonylchloride, triethylamine, dichloromethane, 4 h, RT
c: Sodium cyanide, dimethylformamide, 5 h, RT
d: Raney nickel, ammonia gas in methanol, $H_2$ 2.5 kg pressure, 14 h
e: 1/ 1-methyl cinnamaldehyde, dichloromethane, 16 h, RT, $N_2$
  2/ Sodium borohydride, methanol, 30 minutes at 0° C.

Compound 2-[2-(2-Methyl-3-phenyl-allylamino)-ethyl-(S)-pyrrolidine-1-carboxylic acid tert-butyl ester (prepared from (S)-Pyrrolidine-1,2-dicarboxylic acid-1-tert-butyl ester according to the scheme 2) 0.47 g (1.3 mmol) and 3,4,5-trimethoxy benzoic acid 0.3 g (1.6 mmol) in dry dichloromethane 10 ml, triethyl amine 0.1 ml was added and stirred at room temperature for 20 min. Then 1-dimethylaminopropyl-3-ethyl carbodiimide 0.3 g (2 mmol) and 1-hydroxybenzotriazole 0.018 g (0.13 mmol) was added at 0° C. The reaction mixture was stirred at room temperature overnight. The reaction mixture was diluted with dichloromethane and was benzoyl)-amino]-ethyl}-(S)-pyrrolidine-1-carboxylic acid tert-butyl ester (Yield: 76%). The compound 0.22 g (0.4 mmol) was dissolved in 5 ml of dry ether and 5 ml of dry ether saturated with HCl was added at 0° C. The reaction mixture was stirred at room temperature for 10 hrs. The ether was concentrated and the residue was washed with dry ether three to four times to yield 0.12 g as a white solid. Yield: 30%.

LC-MSD, m/z for $C_{26}H_{34}N_2O_4$ [M+H]+: 439.3 $^1$H NMR (300 MHz, MeOD): δ 1.6-1.8 (m, 4H), 2.0-2.25 (m, 6H), 3.3-3.5 (m, 3H), 3.2 (m, 3H), 3.5-4.0 (m, 12H), 4.1 (s, 1H), 6.5 (s, 1H), 6.8-7.0 (m, 2H), 7.2-7.5 (m, 5H).

Example 17
3,4,5-Trimethoxy-N-(2-methyl-3-phenyl-allyl)-N-(2-(R)-pyrrolidin-2-yl-ethyl)-benzamide Scheme 3: Preparation of 2-[2-(2-Methyl-3-phenyl-allylamino)-ethyl-(R)-pyrrolidine-1-carboxylic acid tert-butyl ester

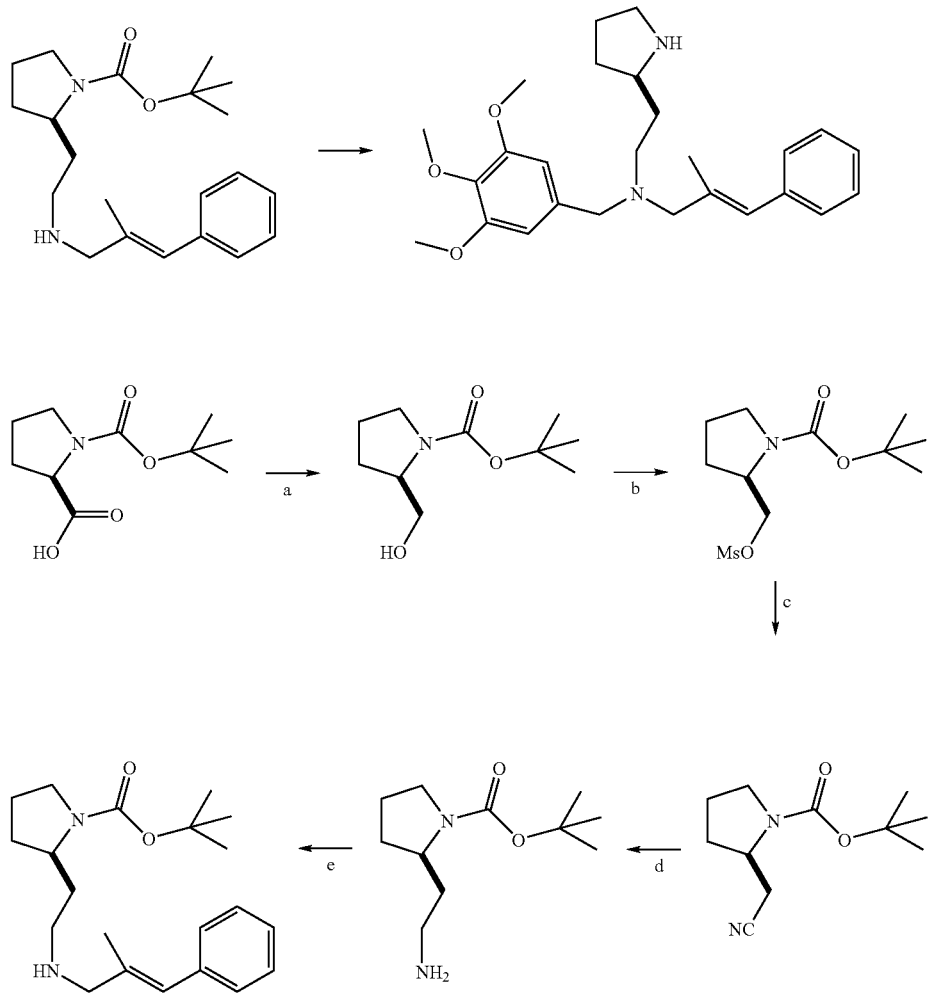

a: Borane dimethylsulfid, THF, 14 h, RT
b: Methansulfonylchloride, triethylamine, dichloromethane, 4 h, RT
c: Sodium cyanide, dimethylformamide, 5 h, RT
d: Raney nickel, ammonia gas in methanol, $H_2$ 2.5 kg pressure, 14 h
e: 1/ 1-methyl cinnamaldehyde, dichloromethane, 16 h, RT, $N_2$
   2/ Sodium borohydride, methanol, 30 minutes at 0° C.

Experimental condition analogous to Example 13 were used with 2-[2-(2-Methyl-3-phenyl-allylamino)]-ethyl-(R)-pyrrolidine-1-carboxylic acid tert-butyl ester (prepared from (R)-Pyrrolidine-1,2-dicarboxylic acid-1-tert-butyl ester according to the scheme 3) 0.6 g (2 mmol), 3,4,5-trimethoxy benzoic acid 0.51 g (2.4 mmol), O-(benzotriazole-1-yl)-N,N,N',N'-tetramethyluronium tetrafluoroborate 1.3 g (4 mmol) and triethylamine 0.2 ml. The intermediate 2-{2-[(2-methyl-3-phenyl-allyl)-(3,4,5-trimethoxy-benzoyl)-amino-]-ethyl}-pyrrolidine-1-carboxylic acid tert-butyl ester was dissolved in 10 ml of dioxane and 5 ml of 6 N HCl, yielding 0.35 g of the compound after basic work-up and purification. Yield: 39%.

LC-MSD, m/z for $C_{26}H_{34}N_2O_4$ [M+H]+: 439.3 $^1$H NMR (300 MHz, MeOD/D2O): δ 1.8 (s, 4H), 1.9-2.25 (m, 6H), 3.2 (m, 3H), 3.5-4.0 (m, 12H), 4.1 (s, 1H), 6.5 (s, 1H), 6.8-7.0 (m, 2H), 7.2-7.5 (m, 5H).

Example 18

3,4,5-Trimethoxy-N[2-(S)-methoxymethyl-pyrrolidin-1-yl)-propyl]-N-(2-methyl-3-phenyl-allyl)-benzamide

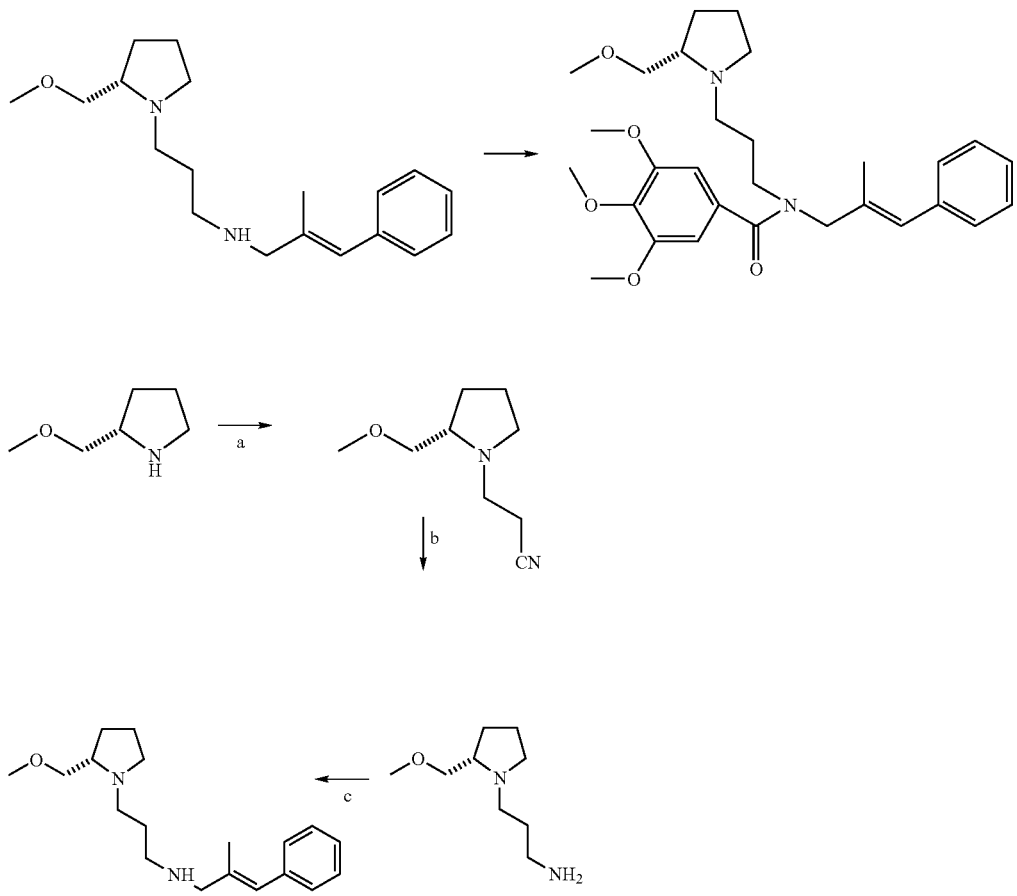

Scheme 4: Preparation of [2-(2-(S)-methoxymethyl-pyrrolidin-1-yl)-propyl]-(2-methyl-3-phenyl-allyl)-amine a: Acrylonitrile, 70° C., 14 h
b: Raney nickel, ammonia gas, methanol, $H_2$ 3 kg pressure
c: 1/ α-methyl cinnamaldehyde, dichloromethane, $N_2$, 18 h, RT
   2/ Sodium borohydride, methanol, 0° C., 15 minutes 3,4,5-trimethoxy benzoic acid 0.335 g (1.58 mmol) and thionyl chloride 0.35 ml (2.64 mmol) were refluxed at 80° C. for 3 hr. The reaction mixture was concentrated to get the corresponding acid chloride. [2-(2-(S)-methoxymethyl-pyrrolidin-1-yl)-propyl]-(2-methyl-3-phenyl-allyl)-amine (prepared from 3-(S)-2-methoxy-ethylpyrrolidine according to the scheme 4) 0.4 g (1.32 mmol) was taken in dry dichloromethane 20 ml. Triethylamine 0.1 ml was added to it at room temperature followed by a solution of 3,4,5-trimethoxy benzoyl chloride in dry dichloromethane 15 ml at 0° C. The reaction mixture was gradually warmed to room temperature, stirred for 2 hr and worked up with dichloromethane. Column chromatographic purification over silica gel gave pure product which was converted to the corresponding hydrochloride salt using HCl in ether to obtain the desired compound 90 mg as a white solid. Yield: 13%.

LC-MSD, m/z for $C_{29}H_{40}N_2O_5$ [M+H]+: 497.3 $^1$H NMR (300 MHz, MeOD): δ 175 (m, 4H), 2.01.9-2.25 (m, 5H), 3.0 (m, 1H), 3.4 (s, 3H), 3.6-4 (m, 17H), 4.1 (s, 1H), 6.4 (s, 1H), 6.8 (s, 2H), 7.2-7.5 (m, 5H).

Example 19

N-[3-(R)-(2-Ethoxy-pyrrolidin-1-yl)-propyl]-3,4,5-trimethoxy-N(2-methyl-3-phenyl-allyl)-benzamide lamine 0.5 ml and O-(benzotriazol-1-yl)-N,N,N',N'-tetramethyluronium tetrafluoroborate 0.893 g (2.78 mmol). The reaction yielded the free amine, which was converted to its hydrochloride using dry HCl in ether to obtain a solid compound 50 mg. Yield: 4%.

Scheme 5: Preparation of [2-(2-(R)-methoxymethyl-pyrrolidin-1-yl)-propyl]-(2-methyl-3-phenyl-allyl)-amine

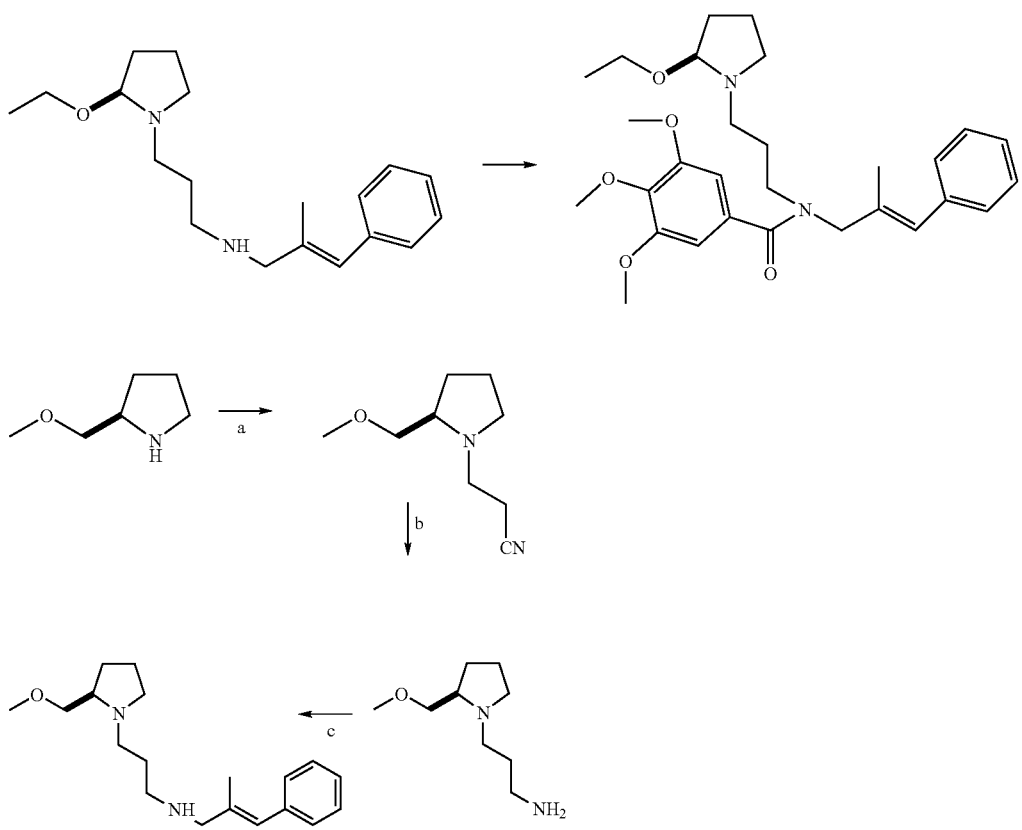

a: Acrylonitrile, 70° C., 14 h
b: Raney nickel, ammonia gas, methanol, H$_2$ 3 kg pressure
c: 1/ α-methyl cinnamaldehyde, dichloromethane, N$_2$, 18 h, RT
   2/ Sodium borohydride, methanol, 0° C., 15 minutes Experimental condition analogous to Example 13 were used with [3-(R)-(ethoxy-pyrrolidin-1-yl)-propyl]-(2-methyl-3-phenyl-allyl)-amine (prepared (R)-2-(methoxymethyl)pyrrolidine described in scheme 5) 0.7 g (2.3 mmol) and 3,4,5-trimethoxy benzoic acid 0.611 g, (2.89 mmol), triethy- LC-MSD, m/z for $C_{29}H_{40}N_2O_5$ [M+H]+: 497.3 $^1$H NMR (300 MHz, MeOD): δ 1.75 (m, 4H), 2.01.9-2.25 (m, 5H), 3.0 (m, 1H), 3.4 (s, 3H), 3.6-4 (m, 17H), 4.1 (s, 1H), 6.4 (s, 1H), 6.8 (s, 2H), 7.2-7.5 (m, 5H).

Example 20

3,4,5-Trimethoxy-N-(2-methyl-3-phenyl-allyl)-N[3-(3-methyl-piperidin-1-yl)-propyl]-benzamide Scheme 6: Preparation of (2-methyl-3-phenyl-allyl)-[3-(3-methyl- piperidin- 1-yl_-propyl-amine

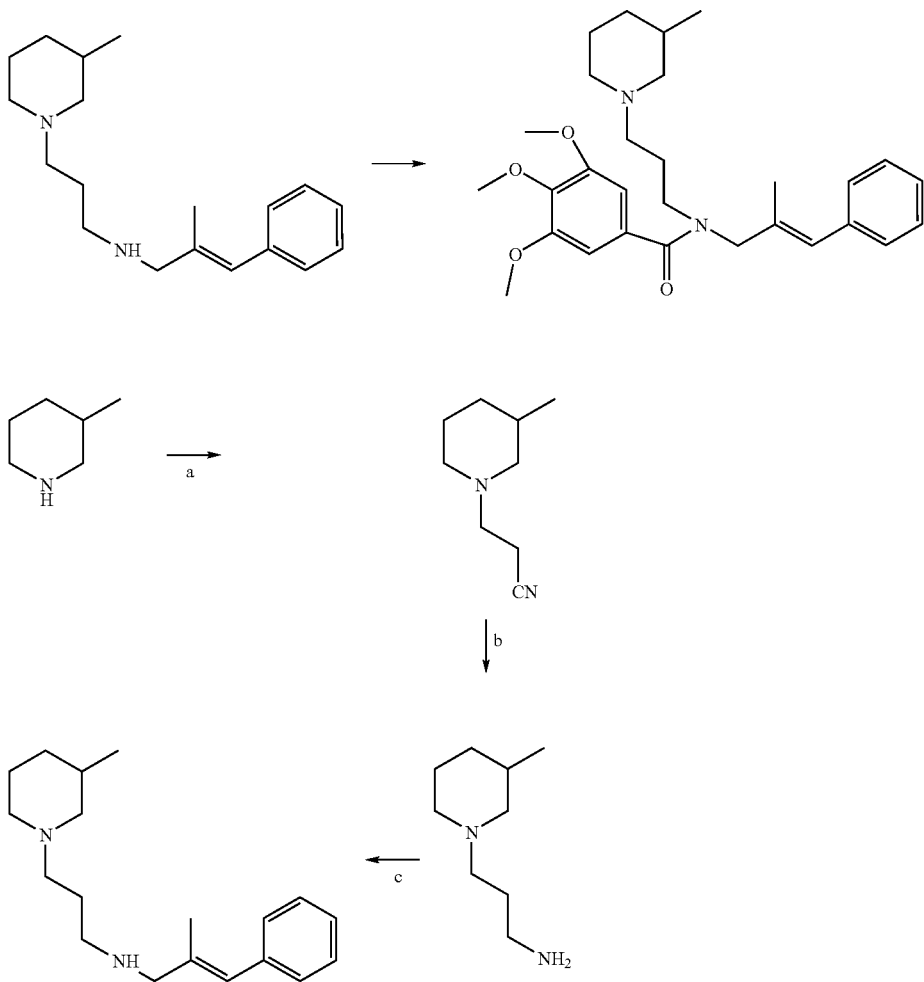

a: Acrylonitrile, 70° C., 14 h
b: Raney nickel, ammonia gas, methanol, $H_2$ 3 kg pressure
c: 1/ α-methyl cinnamaldehyde, dichloromethane, $N_2$, 18 h, RT
  2/ Sodium borohydride, methanol, 0° C., 15 minutes Experimental condition analogous to Example 13 were used with (2-methyl-3-phenyl-allyl)-[3-(3-methyl-piperidin-1-yl)-propyl]-amine (prepared from 3-methyl-piperidine described on the scheme 6) 1 g (3.5 mmol), 3,4,5-trimethoxy benzoic acid 0.89 g (4.2 mmol), triethylamine 0.5 ml and O-(benzotriazol-1-yl)-N,N,N',N'-tetramethyluronium tetrafluoroborate 1.68 g (5.7 mmol). The reaction yielded the free amine, which was converted to its hydrochloride salt (using dry HCl in ether) 0.9 g as white solid. Yield: 49%.

LC-MSD, m/z for $C_{29}H_{40}N_2O_4$ [M+H]+: 481.2, [M+2H]+: 482.2. $^1$H NMR (300 MHz, MeOD): δ 0.8-1.1 (m, 4H), 1.1-1.3 (m, 1H), 1.3-1.4 (s, 1H), 1.6-2.0 (m, 3H), 2.1-2.3 (m, 2H), 2.4-2.5 (m, 1H), 2.5-2.7 (m, 1H), 3.0-3.1 (m, 2H), 3.3-3.5 (m, 2H), 3.5-3.7 (m, 2H), 3.7-3.9 (m, 10H), 4.0-4.4 (m, 2H), 6.5 (s, 1H), 6.7-7.0 (m, 2H), 7.2-7.5 (m, 5H).

Example 21

1-{3-[(2-methyl-3-phenyl-allyl)-(3,4,5-trimethoxy-benzoyl)-amino]-propyl}-pyrrolidine-2(S)-carboxylic acid dimethylamide

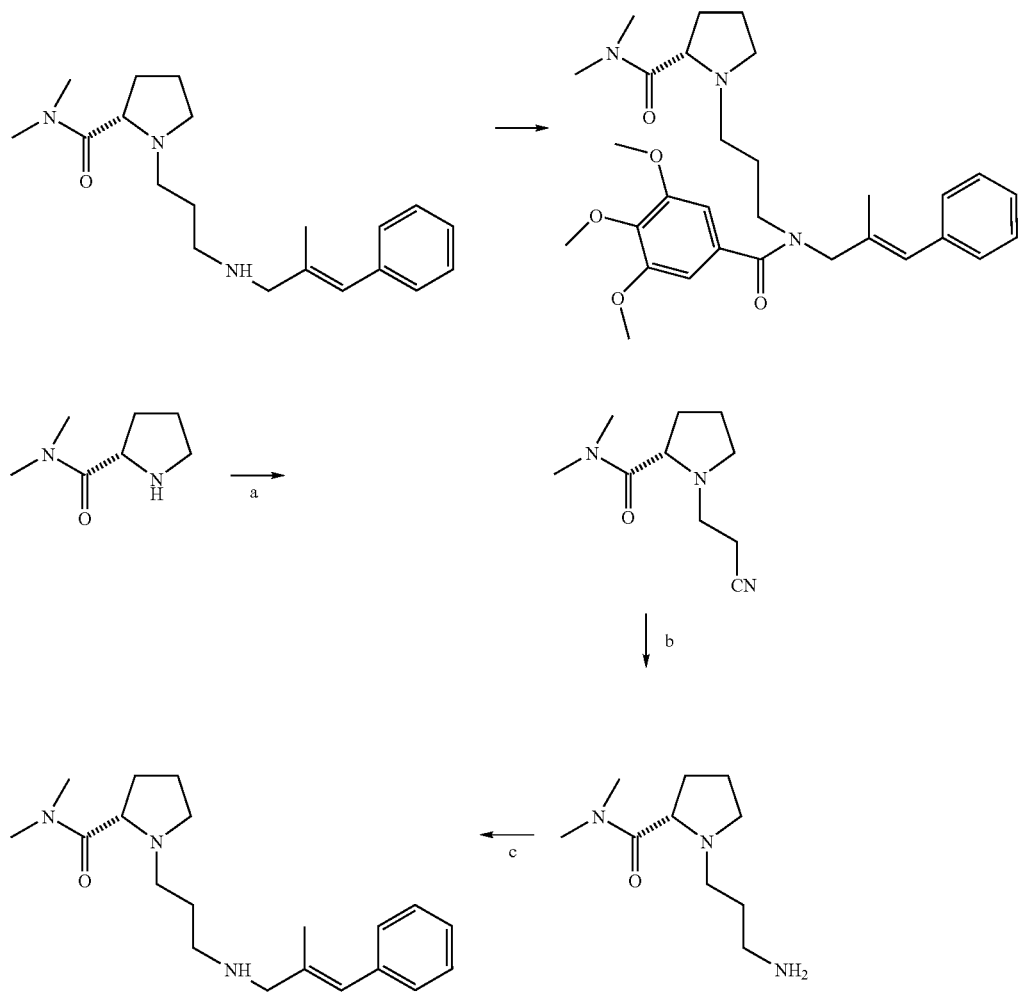

Scheme 7: Preparation of 1-[3-(S)-2-methyl-3-phenyl-allylamino)-propyl]-pyrrolidin-2-carboxylic acid dimethylamide a: Acrylonitrile, 70° C., 14 h
b: Raney nickel, ammonia gas, methanol, $H_2$ 3 kg pressure
c: 1/ α-methyl cinnamaldehyde, dichloromethane, $N_2$, 18 h, RT
  2/ Sodium borohydride, methanol, 0° C., 15 minutes Experimental condition analogous to Example 3 were used with 1-[3-(S)-(2-methyl-3-phenyl-allylamino)-propyl]-pyrrolidin-2-carboxylic acid dimethylamide (prepared from (S)-Pyrrolidin-2-carboxylic acid dimethylamide described on the scheme 7) 0.15 g (0.455 mmol), 3,4,5-trimethoxybenzoic acid 0.125 g (0.58 mmol), triethylamine 0.3 ml and 1-propanephosphonic acid cyclic anhydride solution (50% in ethyl acetate). The reaction yielded 55 mg of free amine.

The compound was dissolved in dry ether and cooled to 0° C. under nitrogen atmosphere, yielding the HCl salt as a white precipitate. The ether layer was decanted off and dried under vacuum to yield 55 mg of a white foam of the HCl salt.

LC-MSD, m/z for $C_{30}H_{41}N_3O_5$ [M+H]+: 524.3 $^1$H NMR (300 MHz, MeOD): δ 1.1-1.3 (m, 1H), 1.75 (m, 3H), 1.75-2.2 (m, 6H), 2.5-2.75 (m, 1H), 2.9-3.1 (m, 7H), 3.2-3.4 (m, 1H), 3.5-3.6 (m, 1H), 3.7-3.9 (m, 9H), 4.0-4.1 (m, 3H), 4.6-4.8 g (m, 1H), 6.4 (s, 1H), 6.8 (s, 2H), 7.1-7.4 (m, 5H).

Example 22

N-[3-(R)-(3-hydroxy-pyrrolidin-1-yl)-propyl]-3,4,5-trimethoxy-N-(2-methyl-3-phenyl-ally)-benzamide

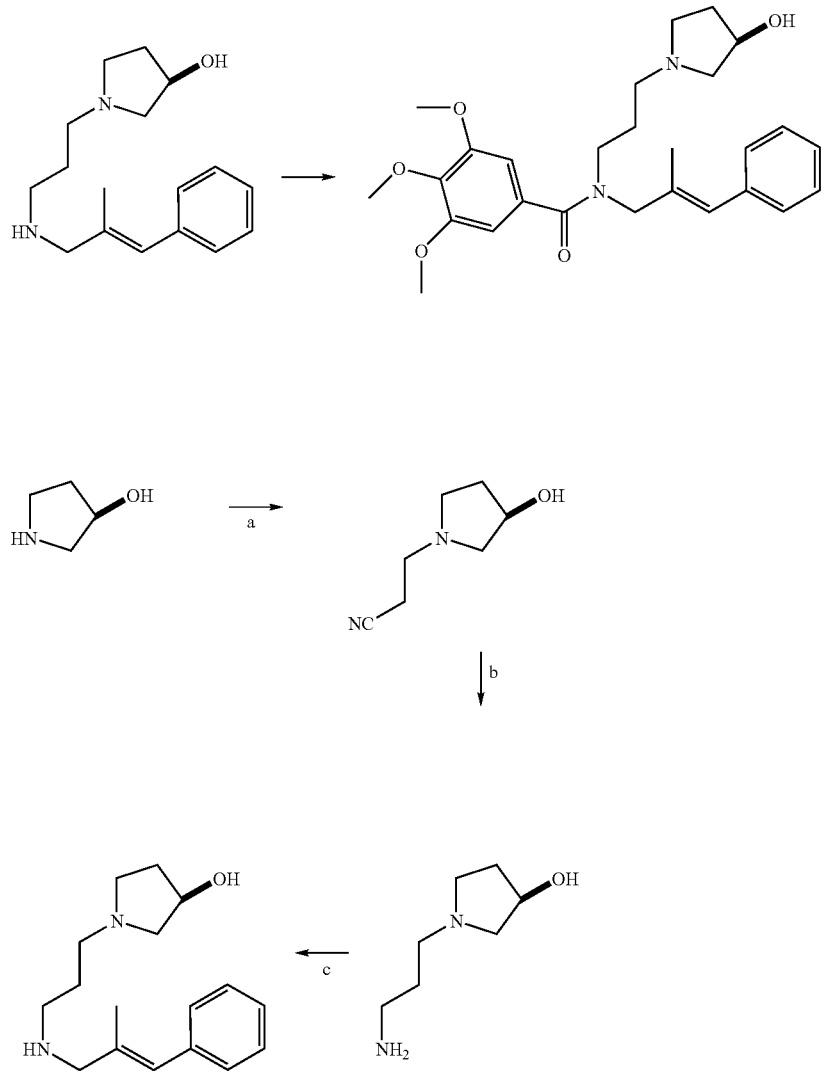

Scheme 8: Preparation of 1-(R)-[3-(2-methyl-3-phenyl-allylamino)- propyl]-pyrrolidin-3-ol a: Acrylonitrile, 70° C., 14 h
b: Raney nickel, ammonia gas, methanol, $H_2$ 3 kg pressure
c: 1/ α-methyl cinnamaldehyde, dichloromethane, $N_2$, 18 h, RT
   2/ Sodium borohydride, methanol, 0° C., 15 minutes Experimental condition analogous to Example 3 were used with 1-(R)-[3-(2-methyl-3-phenyl-allylamino)-propyl]-pyrrolidin-3-ol (prepared from (R)-pyrrolidin-3-ol described in the scheme 8) 0.5 g (1.845 mmol), 3,4,5-trimethoxybenzoic acid 0.46 g (2.1 mmol), triethylamine 0.3 ml, and 1-propane-phosphonic acid cyclic anhydride solution (50% in ethyl acetate) 0.34 g in 20 ml ethyl acetate. The reaction yielded 28 mg of free amine. The compound was dissolved in dry ether and transformed to the HCl salt, giving 30 mg of white solid. Yield: 3%.

LC-MSD, m/z for $C_{27}H_{36}N_2O_5$ [M+H]+: 469.4

Example 23

N-[3-(2-benzyl-piperidin-1-yl)-propyl]-3,4,5-trimethoxy-N-(2-methyl-3-phenyl-allyl)-benzamide

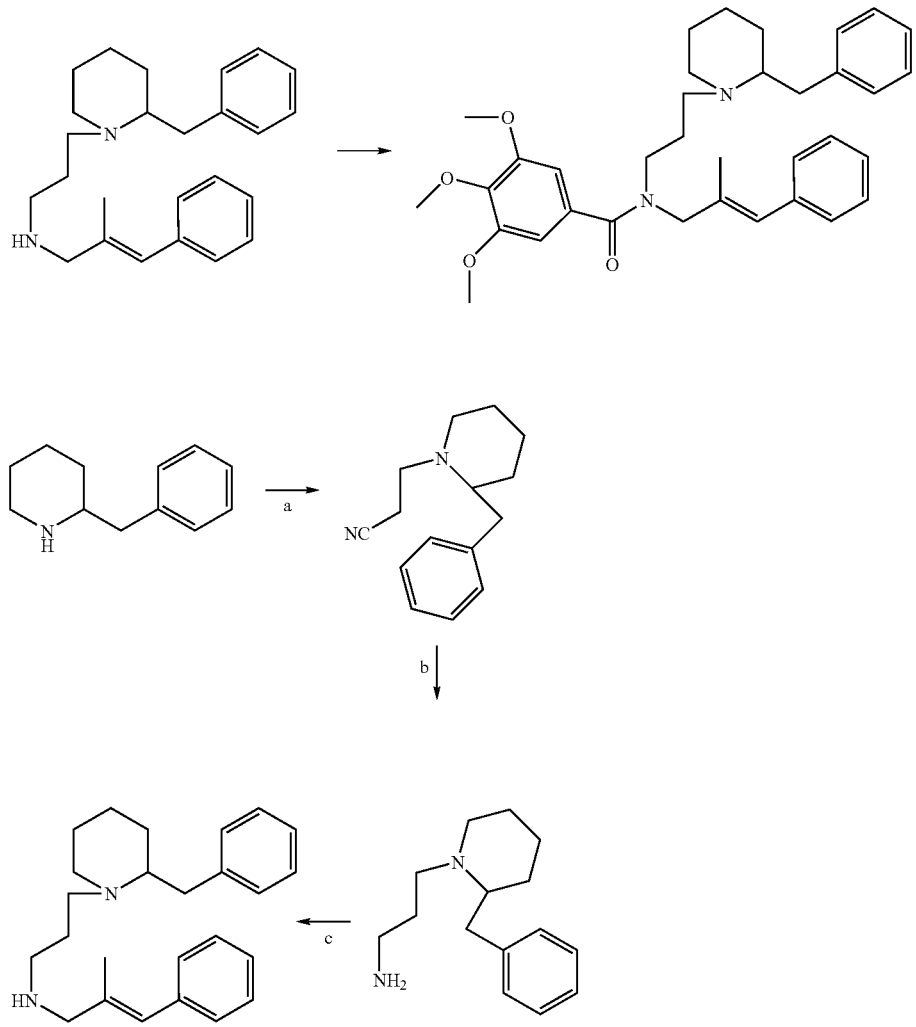

Scheme 9: Preparation of [3-(2-benzyl-piperidin-1-yl)-propyl]-(2-methyl-3- phenyl-allyl)-amine a: Acrylonitrile, 70° C., 14 h
b: Raney nickel, ammonia gas, methanol, $H_2$ 3 kg pressure
c: 1/ α-methyl cinnamaldehyde, dichloromethane, $N_2$, 18 h, RT
  2/ Sodium borohydride, methanol, 0° C., 15 minutes Experimental condition analogous to Example 3 were used with [3-(2-benzyl-piperidin-1-yl)-propyl]-(2-methyl-3-phenyl-allyl)-amine (prepared from 2-benzyl piperidine described on scheme 9) 0.2 g (0.5 mmol), 3,4,5-trimethoxybenzoic acid 0.139 g (0.65 mmol), triethylamine 0.6 ml, and 1-propanephosphonic acid cyclic anhydride solution (50% in ethyl acetate) 0.5 g in 20 ml ethyl acetate. The free amine was transformed to the HCl salt in ether, yielding 90 mg of off-white solid. Yield: 30%.

LC-MSD, m/z for $C_{35}H_{44}N_2O_4$ [M+H]+: 557.5 $^1$H NMR (300 MHz, MeOD): δ 1.05 (t, 1H), 1.3-1.8 (m, 10H), 2.0-2.2 (m, 2H), 2.7-2.8 (m, 1H), 2.8-3.9 (m, 20H), 4.4.2 (m, 2H), 6.4 (s, 1H), 6.8 (s, 2H), 7.1-7.4 (m, 5H).

Example 24

3,4,5-Trimethoxy-N-(2-methyl-3-phenyl-allyl)-N-[3-(2-methyl-pyrrolidin-1-yl)-propyl]-benzamide Scheme 10: Preparation of (2-methyl-3-phenyl-allyl)-[3-(2-methyl- pyrrolidin-1-yl)-propyl]-amine

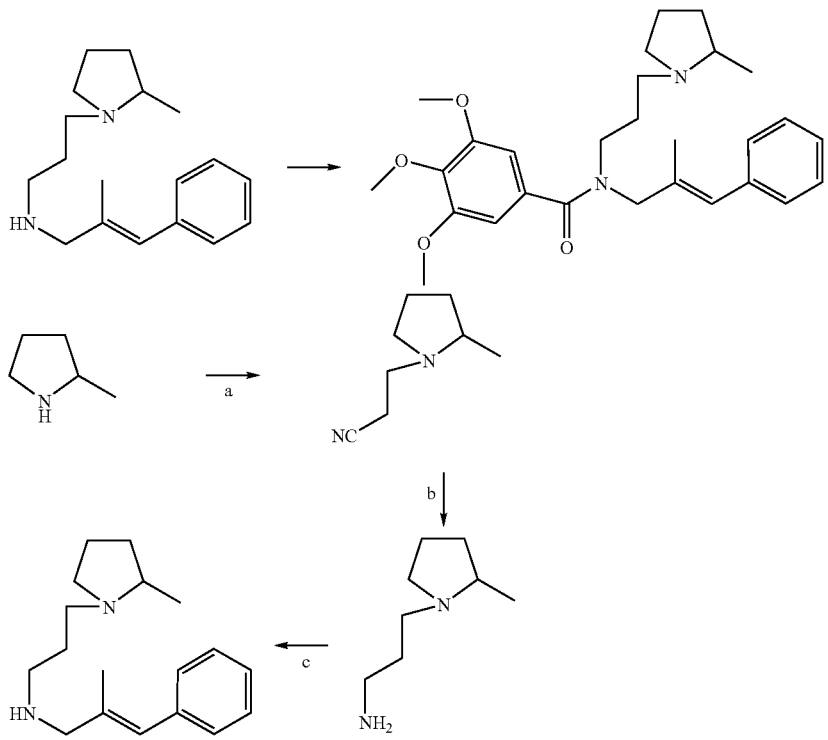

a: Acrylonitrile, 70° C., 14 h
b: Raney nickel, ammonia gas, methanol, H$_2$ 3 kg pressure
c: 1/ α-methyl cinnamaldehyde, dichloromethane, N$_2$, 18 h, RT
2/ Sodium borohydride, methanol, 0° C., 15 minutes Experimental condition analogous to Example 3 were used with (2-Methyl-3-phenyl-allyl)-[3-(2-methyl-pyrrolidin-1-yl)-propyl]-amine (prepared from 2-methyl-pyrrolidine describe on scheme 10) 0.14 g (0.5 mmol), 3,4,5-trimethoxybenzoic acid 0.130 g (0.65 mmol), triethylamine 0.1 ml, and propanephosphonic acid cyclic anhydride solution (50% in ethyl acetate) solution (50% in ethyl acetate) 0.7 g in 10 ml ethyl acetate. The free amine was transformed to the HCl salt in ether, giving 40 mg of a brown semi-solid. Yield: 15%.

LC-MSD, m/z for C$_{28}$H$_{38}$N$_2$O$_4$ [M+H]+: 467.2 $^1$H NMR (300 MHz, MeOD): δ1.0 (m, 1H)1.2 (t, 2H), 1.3-1.5 (m, 2H), 1.7-1.8 (m, 4H), 2.1-2.5 (m, 5H), 3.0-3.2 (m, 2H), 3.5-3.6 (m, 2H), 3.6-3.9 (m, 9H), 4.2 (m, 2H), 6.5 (s, 1H), 6.9 (s, 2H), 7.2-7.5 (m, 5H).

Example 25

N-(3-Hydroxy-propyl)-3,4,5-trimethoxy-N-(2-methyl-3-phenyl-allyl)-benzamide

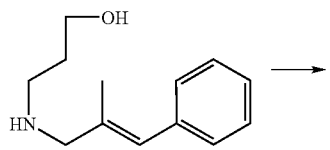

-continued

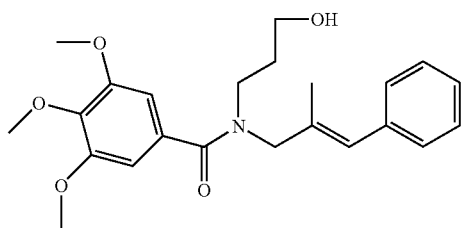

3,4,5-trimethoxybenzoic acid 6.1 g (28 mmol) and thionyl chloride 5.22 g were refluxed together under nitrogen for 4.5 h. Excess thionyl chloride was then evaporated under vacuum and dried in a high vacuum pump. This dry acid chloride was then dissolved in anhydrous THF 5 ml and added to an ice cold 10% NaOH solution 3-(2-methyl-3-phenyl-allylamino)-propan-1-ol stirring. The reaction mixture was then allowed to come to room temperature gradually. After 2 h, the reaction was completed. The mixture was then extracted with dichloromethane and solvent evaporated followed by drying with sodium sulfate. The crude alcohol was then purified by column chromatography in silica gel (9/1: CHCl3/MeOH) to afford the pure alcohol as white solid 8 g. Yield: 71%.

$^1$H NMR (300 MHz, CDCl$_3$): δ1.8-2.0 (m, 5H), 3.5-4.0 (m, 16H), 6.5 (s, 1H), 6.9 (s, 2H), 7.2-7.5 (m, 5H).

Example 26

N-[3-(4-Benzyl-piperazine-1-yl)-propyl]-3,4,5-trimethoxy-N(2-methyl-3-phenyl-allyl)-benzamide

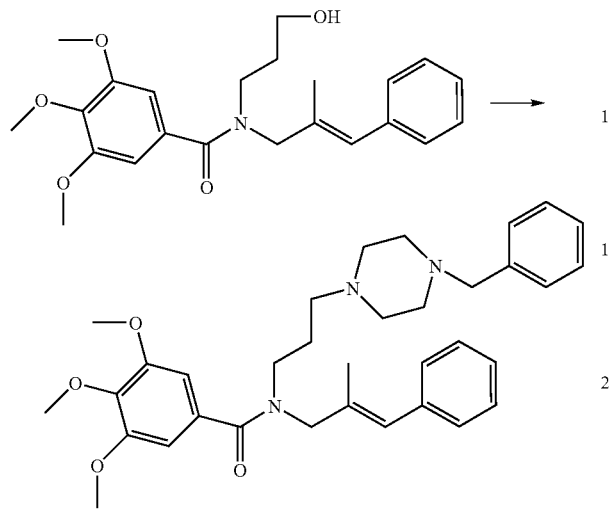

N-(3-Hydroxy-propyl)-3,4,5-trimethoxy-N-(2-methyl-3-phenyl-allyl)-benzamide 1 g (2.5 mmol) was dissolved in 20 ml dry ether under nitrogen. The solution was then cooled to 0° C. and phosphorus tribromide 0.34 g was added drop-wise with stirring. The mixture was allowed to warm to room temperature gradually and stirred at room temperature for 1 h. Crushed ice was then added to the reaction mixture. The organic layer was washed with 10% sodium bicarbonate solution and brine. The organic layer was dried with sodium sulfate and concentrated to obtain the intermediate N-(3-hydroxy-propyl)-3,4,5-trimethoxy-N-(2-methyl-3-phenyl-allyl)-benzamide. This bromo intermediate 0.6 g (1.3 mmol) in 5 ml dimethylformamide, was added to a mixture of 1-benzyl piperazine 0.26 g (1.4 mmol) and 0.3 g (1.5 mmol) of potassium carbonate in 5 ml DMF. The reaction mixture was warmed at room temperature, and was stirred for 17 hours. 30 ml of water was added to this mixture and extracted with chloroform (3×30 ml). The organic layer was dried with sodium sulfate and evaporated to get a mixture of compounds. Purification using silica gel column elution with 5% methanol in chloroform yielded 80 mg of the free amine. Yield: 11%. The free amine was then transformed to HCl salt gave white powder 40 mg.

LC-MSD, m/z for $C_{34}H_{43}N_3O_4$ [M+H]+: 558.3 $^1$H NMR (300 MHz, MeOD): δ1.0 (m, 1H), 1.2 (t, 2H), 1.3-1.5 (m, 2H), 1.7-1.8 (m, 2H), 2.1-2.5 (m, 2H), 3.2 (s, 4H), 3.4-3.5 (m, 3H), 3.6-4.0 (m, 9H), 4.1 (m, 2H), 4.5 (m, 2H), 6.5 (s, 1H), 6.9 (s, 2H), 7.2-7.6 (m, 10H).

Example 27

N-[3-(4-Benzyl-piperidin-1-yl)-propyl]-3,4,5-trimethoxy-N-(2-methyl-3-phenyl-allyl)-benzamide

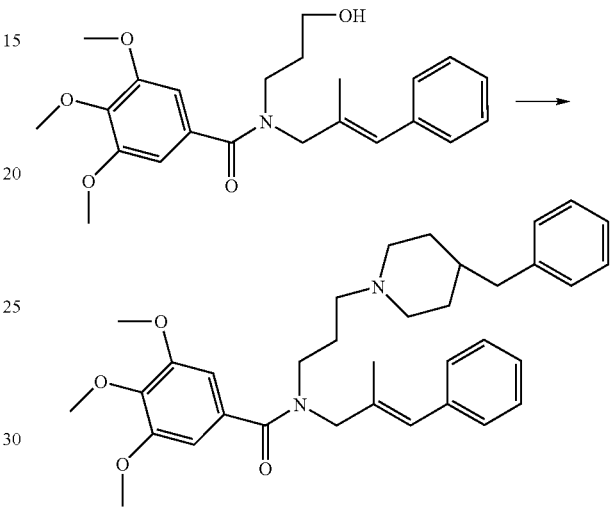

Experimental condition analogous to Example 26 were used with N-(3-hydroxy-propyl)-3,4,5-trimethoxy-N-(2-methyl-3-phenyl-allyl)-benzamide intermediate (prepared from N-(3-Hydroxy-propyl)-3,4,5-trimethoxy-N-(2-methyl-3-phenyl-allyl)-benzamide) 0.4 g (0.8 mmol), 4-benzyl piperidine 0.13 g (0.74 mmol) and 0.4 g potassium carbonate, gave 80 mg as a free amine. This compound was transformed to HCl salt, gave 87 mg of brown solid. Yield: 19%.

LC-MSD, m/z for $C_{35}H_{44}N_2O_4$ [M+H]+: 557.3

Example 28

N-[3-(S)-(3-Benzyl-piperazin-1-yl)-propyl]-3,4,5-trimethoxy-N-(2-methyl-3-phenyl-allyl)-benzamide Scheme 11: Preparation of [3-(S)-(3-benzyl-piperazin-1-yl)-propyl]-(2-methyl-3-phenyl-allyl)-amine

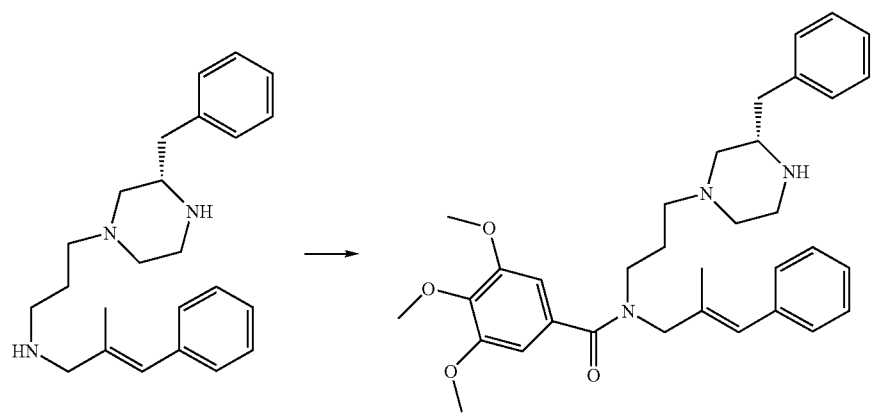

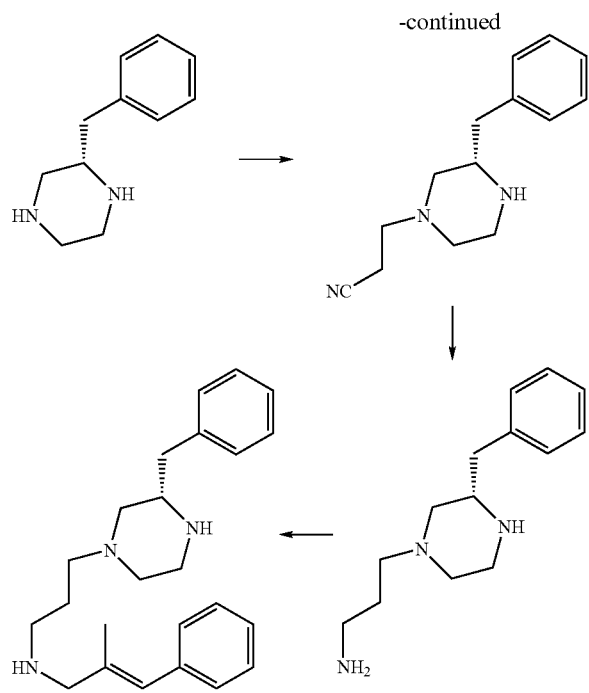

a: Acrylonitrile, 70° C., 14 h
b: Raney nickel, ammonia gas, methanol, $H_2$ 3 kg pressure
c: 1/ α-methyl cinnamaldehyde, dichloromethane, $N_2$, 18 h, RT
  2/ Sodium borohydride, methanol, 0° C., 15 minutes Experimental condition similar to Example 18 were used with [3-(S)-(3-benzyl-piperazin-1-yl)-propyl]-(2-methyl-3-phenyl-allyl)-amine (prepared from (S)-2-benzyl piperazine described on scheme 11) 0.08 g (0.24 mmol), 3,4,5-trimethoxy benzoic acid 0.05 g (0.24 mmol), thionyl chloride 0.02 ml (0.46 mmol) and triethylamine. The free amine after purification was transformed to HCl salt, yielding 45 mg of a brown, semi-solid salt. Yield: 7%.

LC-MSD, m/z for $C_{34}H_{43}N_3O_4$ [M+H]+: 558.3 $^1$H NMR (300 MHz, MeOD): δ1.2 (t, 2H), 1.7-1.9 (m, 3H), 2.3-1.4 (m, 1H), 3.0-4.2 (m, 24H), 6.5 (s, 1H), 6.8 (s, 2H), 7.1-7.4 (m, 10H).

Example 29

3,4,5-Trimethoxy-N-(2-methyl -3-phenyl-ally)-N-(S)-pyrrolidin-2-yl-methyl-benzamide Scheme 12: Preparation of 2-(S)-[(2-methyl-3-phenyl-allylamino)-methyl]-pyrrolidin-1-carboxylic acid tert-butyl ester

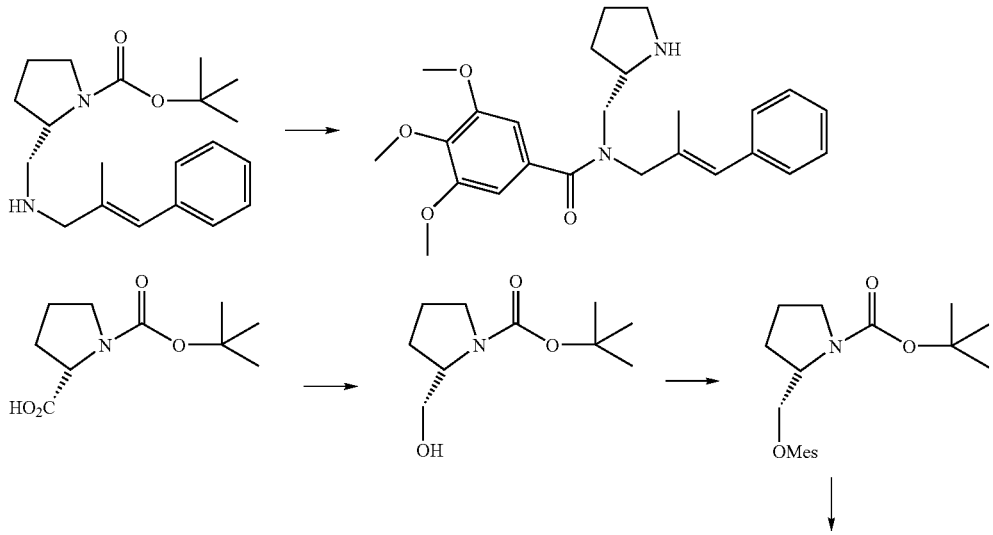

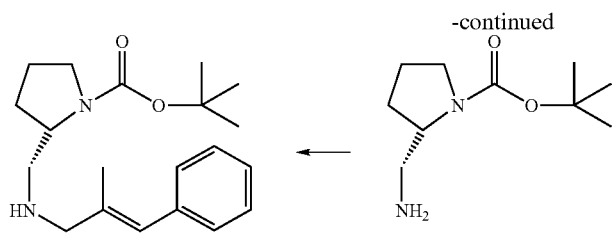 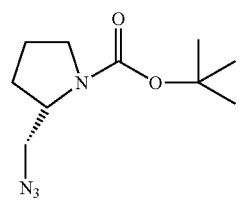

Experimental condition analogous to Example 3 were used with 2-[(2-methyl-3-phenyl-allylamino)-methyl]-pyrrolidin-1-carboxylic acid tert-butyl ester (prepared from 2-(S)-aminomethyl-pyrrolidine-1-carboxylic acid tert-butyl ester according to the scheme 12) 0.6 g (1.8 mmol), 3,4,5-trimethoxy benzoic acid 0.46 g (2.1 mmol), triethylamine 0.1 ml, and propanephosphonic acid cyclic anhydride solution (50% in ethyl acetate) 1.15 g (3.63 mmol) in 20 ml ethyl acetate. The reaction yielded 0.13 g of compound.

2-(S)-[2-Methyl-3-phenyl-allyl)-(3,4,5-trimethoxy-benzoyl)-amino]-methyl-pyrrolidin-1-carboxylic acid tert-butyl ester 0.1 g (0.24 mmol) was dissolved in 5 ml dioxane. To this mixture was added 4 ml of 6 N HCl. The mixture was stirred overnight at room temperature. To this mixture was added a 10% solution of sodium hydroxide. The mixture was extracted with chloroform and the organic layer was washed with brine and dried over sodium sulfate before concentration. Conversion of the free amine into a hydrochloride salt gave 80 mg (0.18 mmol) of a white powder.

LC-MSD, m/z for $C_{25}H_{32}N_2O_4$ [M+H]+: 425.3. $^1$H NMR (300 MHz, MeOD/D$_2$O): δ1.2 (s, 1H), 1.7-1.9 (m, 4H), 2.0-2.2 (m, 2H), 2.2-2.3 (m, 1H), 3.2-3.5 (m, 3H), 3.5-4.0 (m, 10H), 4.1 (s, 1H), (6.5 (s, 1H), 7.0 (s, 2H), 7.2-7.4 (m, 5H).

Example 30

(S)-N-(1-benzyl-pyrrolidin-2-ylmethyl)-3,4,5-trimethoxy-N-(2-methyl-3-phenyl-allyl)-benzamide

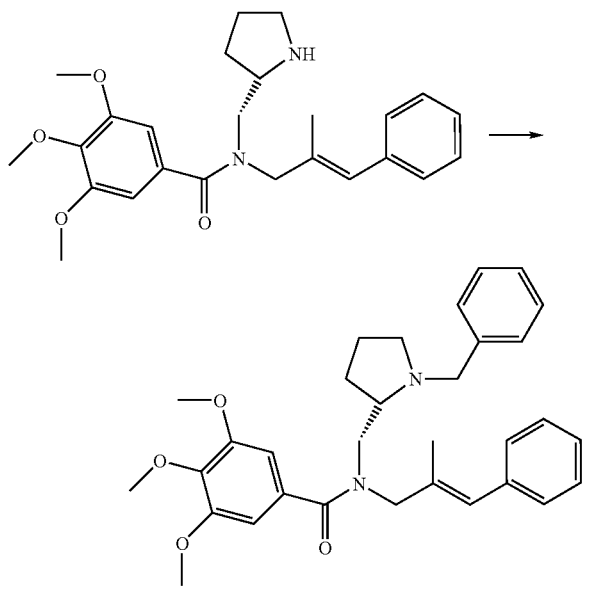

Experimental condition analogous to Example 14 from 3,4,5-Trimethoxy-(S)-N-(2-methyl-3-phenyl-allyl-N-pyrrolidin-2-ylmethyl-benzamide, 0.2 g (0.4 mmol). Benzaldehyde, 0.14 ml (1.4 mmol), and acetic acid, 0.04 ml (0.7 mmol), and sodium cyanoborohydride, 0.04 g (0.7 mmol), gave 120 mg of a white powder. Yield: 50%.

LC-MSD, m/z for $C_{32}H_{38}N_2O_4$ [M+H]+: 515.5. $^1$H NMR (300 MHz, MeOD): δ1.1 (t, 1H), 1.5-1.7 (s, 3H), 1.9-2.2 (m, 3H), 2.2-2.4 (m, 1H), 3.3-3.7 (m, 2H), 3.8 (s, 10H), 4.0-4.1 (m, 3H), 4.4 (d, 1H), 4.6 (d, 1H), 6.4 (s, 1H), 6.8 (s, 2H), 7.2-7.4 (m, 5H), 7.5 (s, 3H), 7.7 (s, 2H)

Example 31

3,4,5-Trimethoxy-N-(2-methyl-3-phenyl-allyl)-N-(S)-(1-methyl-pyrrolidin-2-yl-methyl)-benzamide

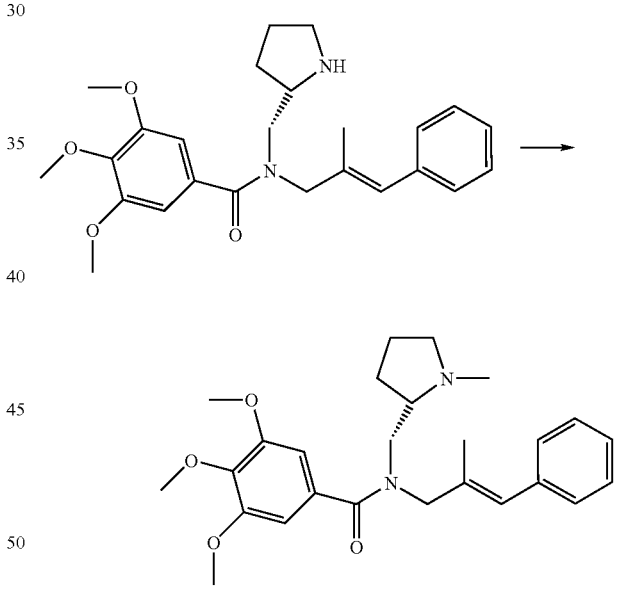

Experimental condition analogous to Example 14 were used with 3,4,5-trimethoxy-(S)-N-(2-methyl-3-phenyl-allyl-N-pyrrolidin-2-ylmethyl-benzamide 0.1 g (0.23 mmol), para formaldehyde 0.035 g (0.11 mmol), acetic acid 0.021 ml (0.35 mmol) and sodium cyanoborohydride 0.02 g (0. 35 mmol). After transforming the free base to HCl salt, 65 mg of white solid was obtained. Yield: 54%.

LC-MSD, m/z for $C_{26}H_{34}N_2O_4$ [M+H]+: 439.4 $^1$H NMR (300 MHz, MeOD): δ1.7 (s, 3H), 1.9-2.2 (m, 3H), 2.2-2.4 (m, 1H), 3.0 (s, 3H), 3.1-3.3 (m, 1H), 3.6-3.8 (m, 11H), 3.8-4.1 (m, 2H), 4.1-4.3 (m, 2H), 4.6 (d, 1H), 6.4 (s, 1H), 6.8 (s, 2H), 7.1-7.4 (m, 5H).

Example 32

N-(S)-(1-Ethyl-pyrrolidin-2-ylmethyl)-3,4,5-tri-methoxy-N-(2-methyl-3-phenyl-allyl)-benzamide

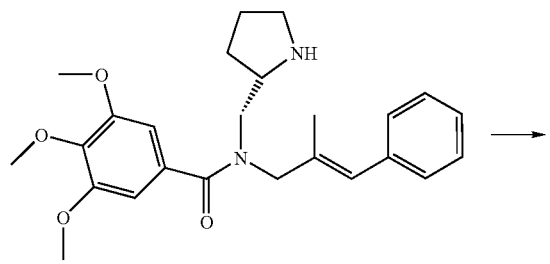

Experimental condition analogous to Example 14 were used with 3,4,5-trimethoxy-(S)-N-(2-methyl-3-phenyl-allyl-N-pyrrolidin-2-ylmethyl-benzamide 0.2 g (0.23 mmol), acetaldehyde 0.1 g (2.3 mmol), acetic acid 0.04 ml (0.7 mmol) and sodium cyanoborohydride 0.043 g (0.7 mmol). After transforming the free base to HCl salt, 40 mg of white solid was obtained. Yield: 35%.

LC-MSD, m/z for $C_{27}H_{36}N_2O_4$ [M+H]+: 453.4 $^1$H NMR (300 MHz, MeOD/$D_2O$): δ1.3-1.5 (m, 3H), 1.5-1.7 (s, 3H), 1.9-2.2 (m, 4H), 2.4-2.5 (m, 1H), 3.1-3.4 (m, 3H), 3.5-3.6 (s, 1H), 3.7-3.8 (m, 9H), 3.7-4.0 (m, 2H), 4.0-4.2 (m, 1H), 4.2 (s, 2H), 6.5 (s, 1H), 6.9 (s, 2H), 7.2-7.5 (m, 5H).

Example 33

N-(S)-[1-(4-Fluoro-benzyl)-pyrrolidin-2-ylmethyl]-3,4,5-trimethoxy-N-(2-methyl-3-phenyl-allyl)-benzamide

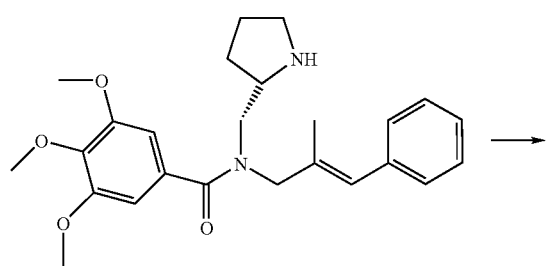

Experimental condition analogous to Example 30 were used with 3,4,5-trimethoxy-(S)-N-(2-methyl-3-phenyl-allyl-N-pyrrolidin-2-ylmethyl-benzamide 0.2 g (0.47 mmol), 4-fluoro benzaldehyde 0.17 g (1.41 mmol), acetic acid 0.04 ml (0.7 mmol) and sodium cyanoborohydride 0.044 g (0.7 mmol). After transforming the free base to HCl salt, 80 mg of white solid was obtained. Yield: 35%.

LC-MSD, m/z for $C_{32}H_{37}N_2O_4F$ [M+H]+: 533.3 $^1$H NMR (300 MHz, MeOD/$D_2O$): δ1.6-1.8 (s, 3H), 2.0-2.3 (m, 3H), 2.4-2.6 (m, 1H), 3.1-3.4 (m, 3H), 3.4-3.5 (m, 1H), 3.5-3.6 (m, 1H), 3.7 (s, 9H), 4.0-4.2 (m, 4H), 4.5 (dd, 3H), 6.5 (s, 1H), 6.9 (s, 2H), 7.1-7.5 (m, 7H), 7.7 (s, 2H).

Example 34

N-(S)-(1-Isopropyll-pyrrolidin-2-ylmethyl)-3,4,5-trimethoxy-N-(2-methyl-3-phenyl-allyl)-benzamide

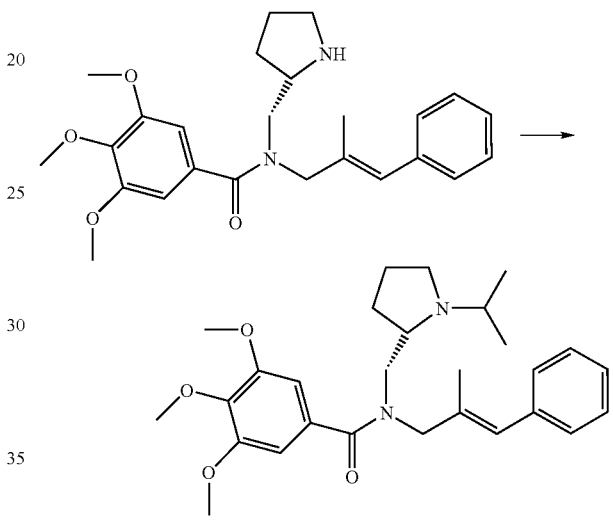

Experimental condition analogous to Example 14 were used with 3,4,5-trimethoxy-(S)-N-(2-methyl-3-phenyl-allyl-N-pyrrolidin-2-ylmethyl-benzamide 0.15 g (0.3 mmol), dry acetone 0.07 g (1 mmol), acetic acid 0.03 ml (0.5 mmol) and sodium cyanoborohydride 0.033 g (0.5 mmol). After transforming the free base to HCl salt, 90 mg of an off-white solid was obtained. Yield: 58%.

LC-MSD, m/z for $C_{28}H_{38}N_2O_4$ [M+H]+: 467.4 $^1$H NMR (300 MHz, MeOD): δ1.4-1.6 (m, 5H), 1.9 (s, 3H), 2.0-2.2 (m, 3H), 2.4-2.5 (m, 1H), 3.3-3.5 (m, 1H), 3.5-3.6 (m, 1H), 3.7-3.9 (m, 12H), 4.0-4.2 (m, 2H), 4.4 (s, 2H), 6.5 (s, 1H), 7.0 (s, 2H), 7.2-7.5 (m, 5H).

Example 35

N-(S)-(1-Cyclohexylmethyl-pyrrolidin2-yl-methyl)-3,4,5-trimethoxy-N-(2-methyl-3-phenyl-allyl)-benzamide

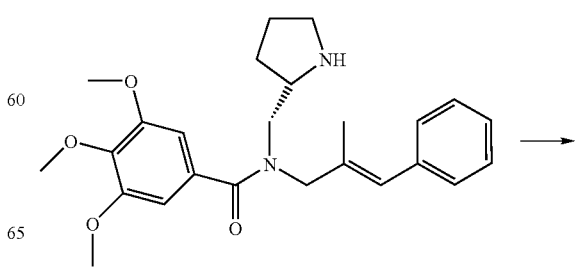

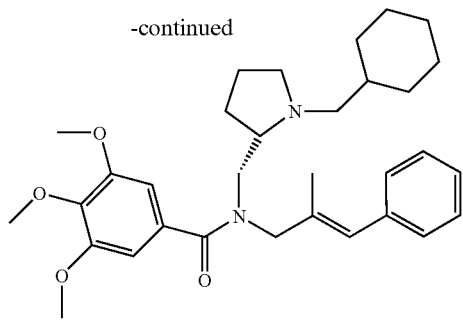

Experimental condition analogous to Example 30 were used with 3,4,5-trimethoxy-(S)-N-(2-methyl-3-phenyl-allyl-N-pyrrolidin-2-ylmethyl-benzamide 0.1 g (0.23 mmol), cyclohexane carboxaldehyde 0.037 g (0.28 mmol), acetic acid 0.02 ml (0.35 mmol) and sodium cyanoborohydride 0.022 g (0.35 mmol). After transforming the free base to HCl salt, 60 mg of a pale yellow solid was obtained. Yield: 46%.

LC-MSD, m/z for $C_{32}H_{44}N_2O_4$ [M+H]+: 521.5 $^1$H NMR (300 MHz, MeOD): δ1.0-1.5 (m, 6H), 1.6-1.9 (m, 8H), 2.0-2.1 (m, 2H), 2.1-2.3 (m, 2H), 2.4-2.5 (m, 1H), 3.0-3.1-3.6 (m, 1H), 3.6-3.9 (m, 12H), 3.9-4.1 (m, 2H), 4.1-4.4 (q, 2H), 6.5 (s, 1H), 7.0 (s, 2H), 7.2-7.5 (m, 5H).

Example 36

3,4,5-Trimethoxy-N-(2-methyl-3-phenyl-allyl)-N-(R)-pyrrolidin-2-ylmethyl-benzamide Experimental condition analogous to Example 22 were used with 2-(R)-[(2-methyl-3-phenyl-allylamino)-methyl]-pyrrolidine-1-carboxylic acid tert-butyl ester (prepared according to the scheme 13) were used with 2-(R)-carboxymethyl-pyrrolidine-1-carboxylic acid tert-butyl ester) 0.5 g (1.51 mmol), 3,4,5-trimethoxy benzoic acid 0.38 g (1.8 mmol), triethylamine 0.1 ml, 1-(dimethylaminopropyl)-3-ethylcarbodiimide 0.43 g (2.2 mmol), and 1-hydroxybenzotriazole 0.2 g (1.5 mmol) in 10 ml DCM. The reaction yielded 0.46 g of 2-(R){[2-methyl-3-phenyl-allyl)-3,4,5-trimethoxy-benzoyl)-amino]-methyl}-pyrrolidine-1-carboxylic acid tert-butyl ester. After BOC deprotection analogous to the Example 13, the compound was transformed to the HCl salt, 0.35 g of a white solid was obtained. Yield: 50%

LC-MSD, m/z for $C_{25}H_{32}N_2O_4$ [M+H]+: 425.4 $^1$H NMR (300 MHz, MeOD): δ 1.1-1.4 (m, 1H), 1.6-1.9 (m, 3H), 2.0-2.2 (m, 2H), 2.2-2.3 (m, 1H), 3.2-3.5 (m, 3H), 3.5-3.7 (m, 1H), 3.7-3.10 (m, 10H), 4.1 (s, 3H), 6.5 (s, 1H), 7.0 (m, 2H), 7.2-7.5 (m, 5H).

Scheme 13: Preparaton of 2-(R)-[(2-methyl-3-phenyl-allylamino)-methyl]-pyrrolidin-1-carboxylic acid tert-butyl ester

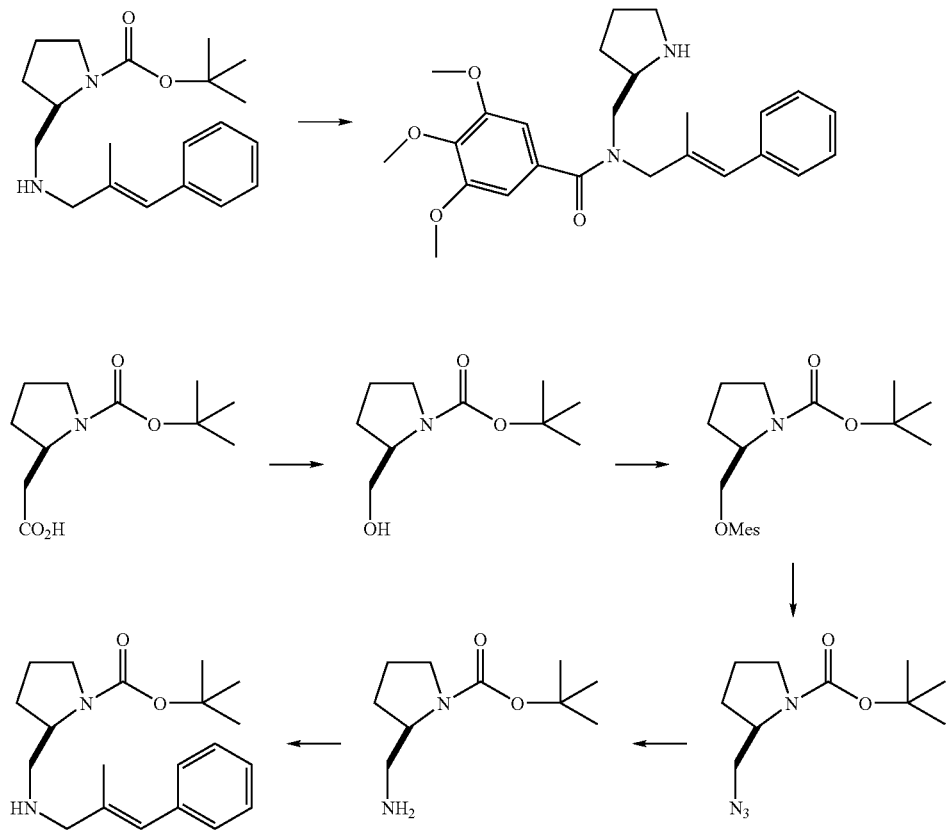

Example 37

N-[3-(4-Fluoro-phenyl)-2-methyl-allyl]-3,4,5-tri-methoxy-N-pyrrolidin-2-ylmethyl-benzamide Scheme 14: Preparation of 3-(4-fluoro-phenyl)-2-methyl-propenal

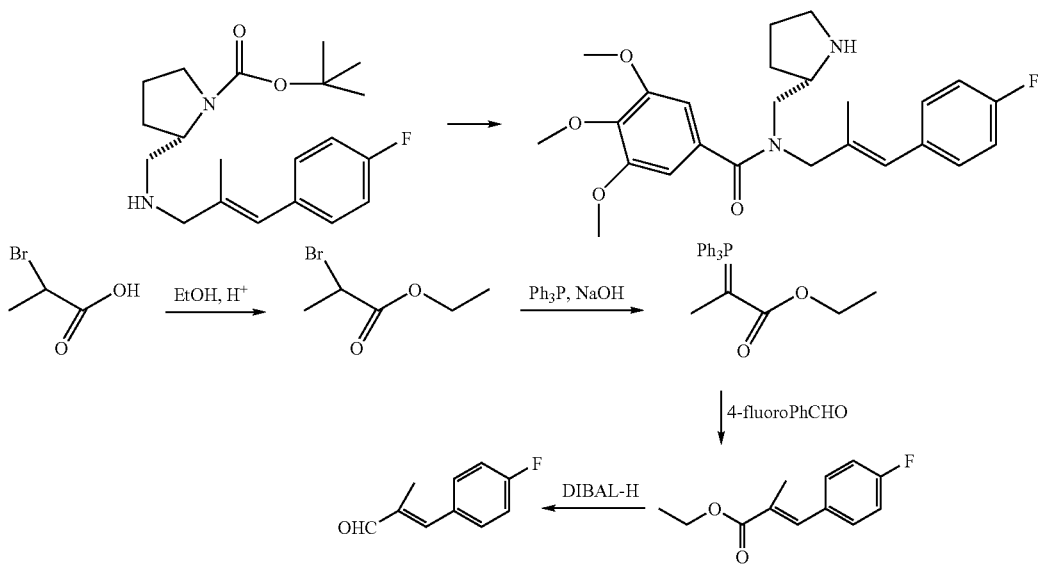

Experimental condition analogous to Example 2 were used with 2-(S)-{[3-(4-fluoro-phenyl)-2-methyl-allylamino]-methyl}-pyrrolidine-1-carboxylic acid tert-butyl ester were used with 2-(S)-carboxymethyl-pyrrolidine-1-carboxylic acid tert-butyl ester and 3-(4-fluoro-phenyl)-2-methyl-propenal described in scheme 14) 0.36 g (1.03 mmol), 3,4,5-trimethoxy benzoic acid 0.26 g (1.2 mmol), triethylamine 0.2 ml, 1-(dimethylaminopropyl)-3-ethylcarbodiimide 0.29 g (1.55 mmol), and 1-hydroxybenzotriazole 0.014 g (0.1 mmol) in 10 ml DCM. The reaction yielded 0.32 g of 2-(S)-{[3-(4-fluoro-phenyl)-2-methyl-allylamino]-methyl}-pyrrolidine-1-carboxylic acid tert-butyl ester. The BOC deprotection analogous to Example 13, the compound was transformed to the HCl salt, yielding 69 mg of a white solid. Yield: 14%.

LC-MSD, m/z for $C_{25}H_{31}FN_2O_4$ [M+H]+: 443.4 $^1$H NMR (300 MHz, MeOD): δ 1.6-2.0 (m, 5H), 2.0-2.3 (m, 3H), 2.3-2.5 (m, 1H), 3.2-3.6 (m, 2H), 3.6-4.0 (m, 10H), 4.1-4.3 (m, 4H), 6.5 (s, 1H), 7.0 (m, 2H), 7.2-7.4 (m, 4H).

Example 38

N-[3-(2,4-Difluoro-phenyl)-2-methyl-allyl]-3,4,5-trimethoxy-N-pyrrolidin-2-ylmethyl-benzamide

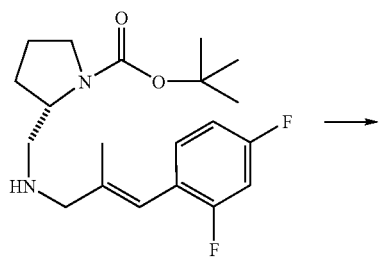

Experimental condition analogous to Example 2 were used with 2-(S)-{[3-(2,4-difluoro-phenyl)-2-methyl-allylaminmo]-methyl}-pyrrolidine-1-carboxylic acid tert-butyl ester were used with 2-(S)-carboxymethyl-pyrrolidine-1-carboxylic acid tert-butyl ester and 3-(2,4-difluoro-phenyl)-2-methyl-propenal described in scheme 15) 0.4 g (1 mmol), 3,4,5-trimethoxy benzoic acid 0.27 g (1.3 mmol), triethylamine 0.1 ml, 1-(dimethylaminopropyl)-3-ethylcarbodiimide 0.31 g (1.63 mmol), and 1-hydroxybenzotriazole 0.014 g (0.1 mmol) in 10 ml DCM. The reaction yielded 0.49 g of 2-(S)-{[3-(2,4-difluoro-phenyl)-2-methyl-allylamino]-methyl}-pyrrolidine-1-carboxylic acid tert-butyl ester. The compound was transformed to the HCl salt, yielding 45 mg of a white solid. Yield: 14%.

LC-MSD, m/z for $C_{25}H_{30}F_2N_2O_4$ [M+H]+: 443.4 $^1$H NMR (300 MHz, MeOD): δ 1.6 (s, 2H), 1.7-2.0 (m, 1H), 2.0-2.2 (m, 2H), 2.2-2.5 (m, 1H), 3.2-3.5 (m, 3H), 3.5-4.0 (m, 10H), 4.1-4.3 (m, 4H) 6.4 (s, 1H), 6.9-7.5 (m, 5H).

Example 39

N-(S)-(1-Cyclobutyl-pyrrolidin-2-ylmethyl)-N-[3-(2,4-difluoro-phenyl)-2-methyl-allyl]-3,4,5-trimethoxy-benzamide

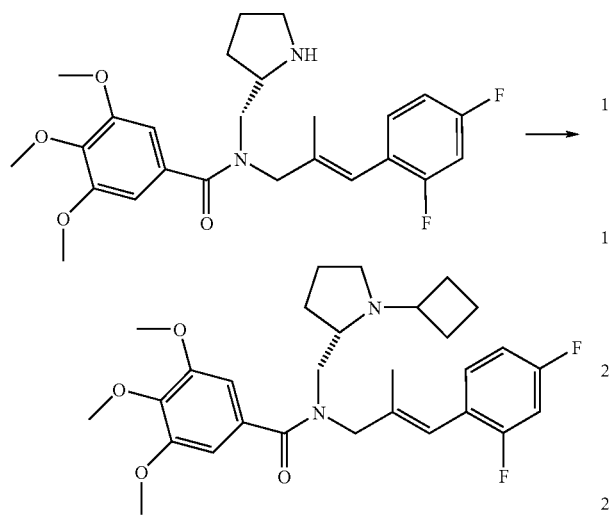

Experimental condition analogous to Example 14 were used with N-(S)-[3-(2,4-difluoro-phenyl)-2-methyl-allyl]-3,4,5-trimethoxy-N-pyrrolidin-2-ylmethyl-benzamide 0.15 g (0.32 mmol), cyclobutanone 0.027 g (0.39 mmol), acetic acid 0.027 ml (0.48 mmol) and sodium cyanoborohydride 0.024 g (0.48 mmol). After transforming the free base to the HCl salt, yielding 90 mg of a white solid. Yield: 46%.

LC-MSD, m/z for $C_{29}H_{36}F_2N_2O_4$ [M+H]+: 515.5

Example 40

N-(S)-(1-Cyclopentyl-pyrrolidin-2-ylmethyl)-N-[3-(2,4-difluoro-phenyl)-2-methyl-allyl]-3,4,5-trimethoxy-benzamide

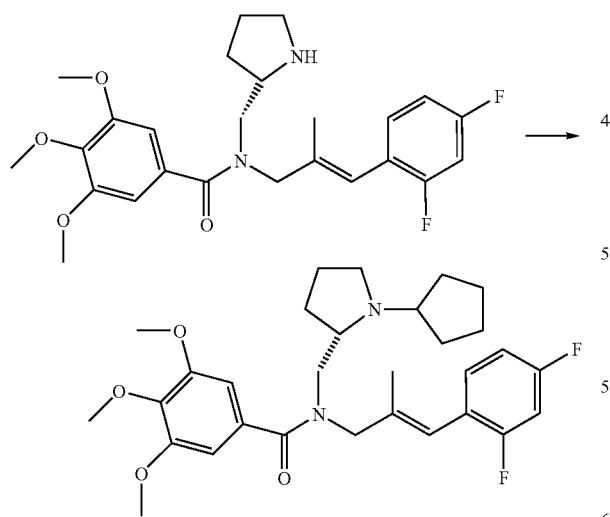

Experimental condition analogous to Example 14 were used with N-(S)-[3-(2,4-Difluoro-phenyl)-2-methyl-allyl]-3,4,5-trimethoxy-N-pyrrolidin-2-ylmethyl-benzamide 0.12 g (0.26 mmol), cyclopentanone 0.026 g (0.313 mmol), acetic acid 0.023 ml (0.39 mmol) and sodium cyanoborohydride 0.025 g (0.391 mmol). The free base was converted to the HCl salt, yielding 90 mg of colorless semi-solid. Yield: 61%.

LC-MSD, m/z for $C_{30}H_{38}F_2N_2O_4$ [M+H]+: 529.5 $^1$H NMR (300 MHz, MeOD): δ 1.5-2.0 (m, 9H), 2.0-2.5 (m, 6H), 3.2-3.5 (m, 1H), 3.7-4.0 (m, 13H), 4.1-4.4 (m, 3H) 6.4 (s, 1H), 6.8-7.4 (m, 5H).

Example 41

N-[3-2,4-Difluoro-phenyl)-2-methyl-allyl]-3,4,5-trimethoxy-N-(S)-[1-(tetrahydro-pyran-4-ylmethyl)-pyrrolidin-2-ylmethyl]-benzamide

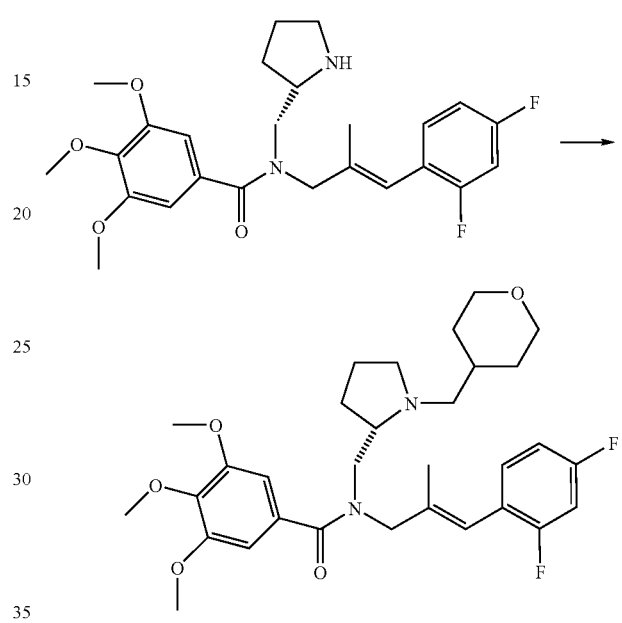

Experimental condition analogous to Example 14 were used with N-(S)-[3-(2,4-Difluoro-phenyl)-2-methyl-allyl]-3,4,5-trimethoxy-N-pyrrolidin-2-ylmethyl-benzamide 0.1 g (0.2 mmol), pyrane-4-carboxaldehyde 0.029 g (0.26 mmol), acetic acid 0.018 ml (0.32 mmol) and sodium cyanoborohydride 0.029 g (0.32 mmol). The free base was converted to the HCl salt, yielding 40 mg of pale yellow solid. Yield: 33%.

LC-MSD, m/z for $C_{31}H_{40}F_2N_2O_5$ [M+H]+: 559.5 $^1$H NMR (300 MHz, MeOD): δ 1.3-1.5 (m, 2H), 1.5-1.7 (m, 4H), 2.0-2.5 (m, 7H), 3.2-3.5 (m, 3H), 3.6-4.0 (m, 16H), 4.0-4.4 (q, 1H), 6.4 (s, 1H), 6.8-7.4 (m, 5H).

Example 42

N-[3-(2,4-Difluoro-phenyl)-2-methyl-allyl]-3,4,5-trimethoxy-N-(S)-[1-(tetrahydro-pyran-4-yl)-pyrrolidin-2-ylmethyl]-benzamide

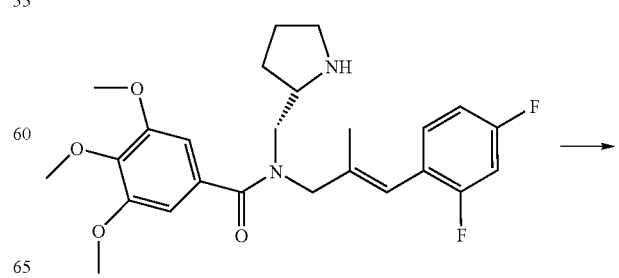

-continued

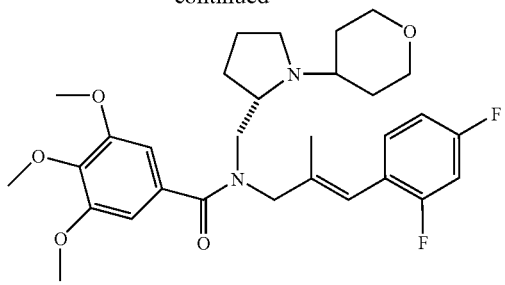

Experimental condition analogous to Example 14 were used with N-(S)-[3-(2,4-Difluoro-phenyl)-2-methyl-allyl]-3,4,5-trimethoxy-N-pyrrolidin-2-ylmethyl-benzamide 0.13 g (0.28 mmol), tetrahydro-4H-pyran-4-one 0.034 g (0.33 mmol), acetic acid 0.026 ml (0.42 mmol) and sodium cyanoborohydride 0.027 g (0.43 mmol). The free base was converted to the HCl salt, yielding 70 mg of colourless semi-solid. Yield: 43%.

LC-MSD, m/z for $C_{30}H_{38}F_2N_2O_5$ [M+H]+: 545.6 $^1$H NMR (300 MHz, MeOD): δ 1.5-1.8 (m, 3H), 1.8-2.0 (m, 2H), 2.0-2.5 (m, 6H), 3.4-3.6 (m, 3H), 3.5-4.0 (m, 13H), 4.0-4.2 (m, 3H), 4.2-4.4 (m, 2H), 6.4 (s, 1H), 6.8-7.4 (m, 5H).

Example 43

N-[3-(2,4-Difluoro-phenyl)-2-methyl-allyl]-3,4,5-trimethoxy-N-(S)-1-pyridin-4-ylmethyl-pyrrolidin-2-ylmethyl)-benzamide

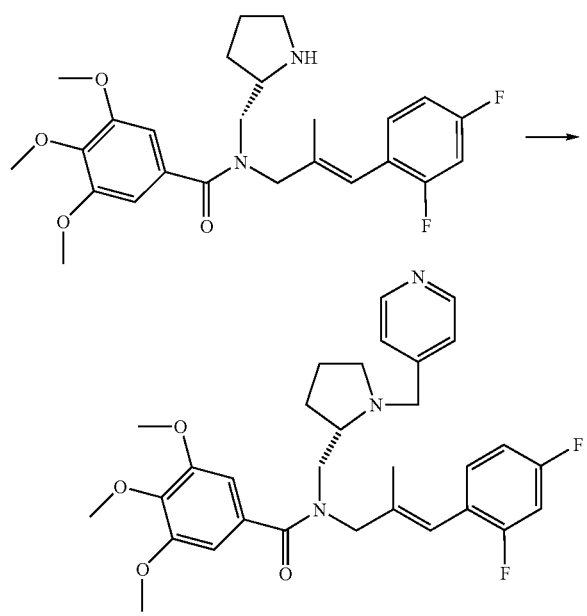

Experimental condition analogous to Example 14 were used with N-(S)-[3-(2,4-Difluoro-phenyl)-2-methyl-allyl]-3,4,5-trimethoxy-N-pyrrolidin-2-ylmethyl-benzamide 0.15 g (0.32 mmol), pyridine-4-carboxaldehyde 0.041 g (0.39 mmol), acetic acid 0.029 ml (0.48 mmol) and sodium cyanoborohydride 0.03 g (0.48 mmol). The free base was converted to the HCl salt, yielding 90 mg of white solid. Yield: 47%.

LC-MSD, m/z for $C_{31}H_{35}F_2N_3O_5$ [M+H]+: 552.4

Example 44

N-(S)-(1-Cyclopentylmethyl-pyrrolidin-2-ylmethyl)-N-[3-(2,4-difluoro-phenyl)-2-methyl-allyl]-3,4,5-trimethoxy-benzamide

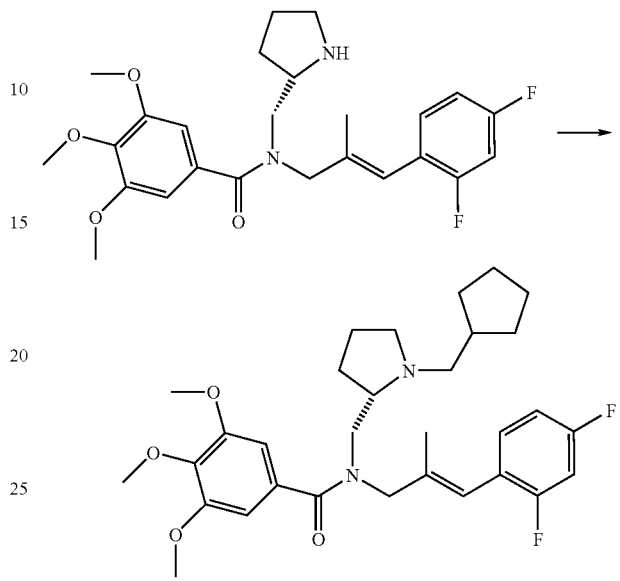

To a solution of N-(S)-[3-(2,4-difluoro-phenyl)-2-methyl-allyl]-3,4,5-trimethoxy-N-pyrrolidin-2-ylmethyl-benzamide 0.09 g (0.19 mmol), dry acetonitrile 10 ml was added anhydrous potassium carbonate 0.07 g (0.5 mmol), potassium iodide 0.0032 g (0.019 mmol) and methanesulfonic acid cyclopentylmethyl ester 0.1 g (0.56 mmol) at room temperature under nitrogen atmosphere. The reaction mixture was heated at 70° C. for 40 hours, was then poured into ice cold water 20 ml and was extracted with chloroform (2×15 ml). Organic layer was washed with brine, dried over anhydrous sodium sulfate and concentrated. Crude material was column purified silica gel, 60-120, chloroform:methanol to get the free amine. This was converted to its hydrochloride to get 15 mg yellow solid.

LC-MSD, m/z for $C_{31}H_{40}F_2N_2O_4$ [M+H]+: 543.60 $^1$H NMR (300 MHz, MeOD): δ 12-1.5 (m, 3H), 1.5-1.8 (m, 8H), 1.8-2.0 (m, 3H), 2.0-2.1 (m, 2H), 2.3-2.5 (m, 2H), 3.1-3.4 (m, 3H), 3.5-4.0 (m, 11H), 4.0-4.4 (m, 2H), 6.4 (s, 1H), 6.8-7.4 (m, 5H).

Example 45

N-[3-(2,4-Difluoro-phenyl)-2-methyl-allyl]-3,4,5-trimethoxy-N-(R)-(1-piperidin-4-ylmethyl)-benzamide

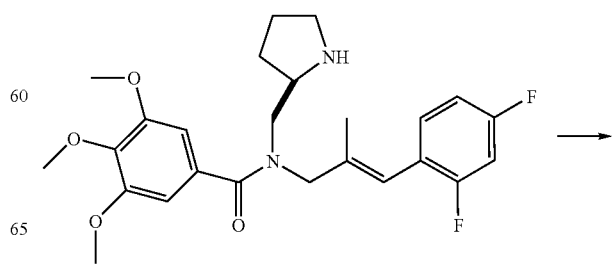

-continued

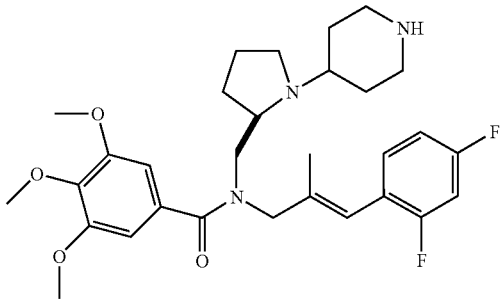

Experimental condition analogous to Example 14 were used with N-(R)-[3-(2,4-Difluoro-phenyl)-2-methyl-allyl]-3,4,5-trimethoxy-N-pyrrolidin-2-ylmethyl-benzamide 0.1 g (0.21 mmol), 4-oxo-piperidine-1-carboxylic acid tert-butyl ester 0.051 g (0.26 mmol), acetic acid 0.018 ml (0.32 mmol) and sodium cyanoborohydride 0.016 g (0.32 mmol). The reaction yielded 120 mg of 4-(2-(R)-{[[3-(2,4-Difluoro-phenyl)-2-methyl-allyl]-(3,4,5-trimethoxy-benzoyl)-amino]-methyl}-pyrrolidin-1-yl)-piperidine-1-carboxylic acid tert-butyl ester. The compound was dissolved in 5 ml of dry ether and 5 ml of dry ether saturated with HCl was added at 0° C. The reaction mixture was stirred at room temperature for 10 hrs. Ether was concentrated and residue was washed with dry ether 3-4 times, yielding 80 mg of a yellow solid.

LC-MSD, m/z for $C_{30}H_{39}F_2N_2O_5$ [M+H]+: 544.6 $^1$H NMR (300 MHz, MeOD): δ 11 (t, 1H), 1.6 (s, 1H), 1.7 (s, 2H), 2.0-2.4 (m, 4H), 2.4-2.5 (m, 2H), 2.5-2.6 (m, 1H), 3.0-3.1 (m, 1H), 3.2 (s, 2H), 3.4-3.7 (m, 6H), 3.7-3.8 (3 s, 9H), 3.9-4.4 (m, 4H), 6.4 (s, 1H), 6.8-7.4 (m, 5H).

Example 46

N-[3-(2,4-Difluoro-phenyl)-2-methyl-allyl]-3,4,5-trimethoxy-N-(R)-1-pyridin-4-ylmethyl-pyrrolidin-2-ylmethyl)-benzamide

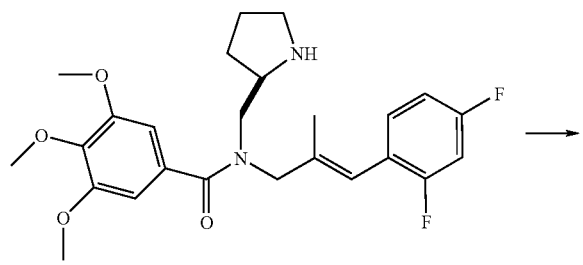

Experimental condition analogous to Example 14 were used with N-(R)-[3-(2,4-difluoro-phenyl)-2-methyl-allyl]-3,4,5-trimethoxy-N-pyrrolidin-2-ylmethyl-benzamide 0.1 g (0.21 mmol), pyridine-4-carboxaldehyde 0.027 g (0.26 mmol), acetic acid 0.018 ml (0.32 mmol) and sodium cyanoborohydride 0.016 g (0.32 mmol). The free base was converted to the HCl salt, yielding 80 mg of white solid. Yield: 47%.

LC-MSD, m/z for $C_{31}H_{35}F_2N_3O_5$ [M+H]+: 552.4 $^1$H NMR (300 MHz, MeOD): δ 1.6 (s, 3H), 2.1-2.4 (s, 3H), 2.5-2.6 (s, 1H), 3.2-3.5 (m, 1H), 3.6-3.9 (m, 10H), 4.1-4.4 (m, 5H), 5.4 (d, 1H), 6.4 (s, 1H), 7.0 (s, 5H), 7.4 (m, 1H), 8.5 (s, 2H), 9.0 (s, 2H).

Example 47

N-(R)-(1-Cyclohexyl-pyrrolidin-2-ylmethyl)-N-[3-(2,4-difluoro-phenyl)-2-methyl-allyl]-3,4,5-trimethoxy-benzamide

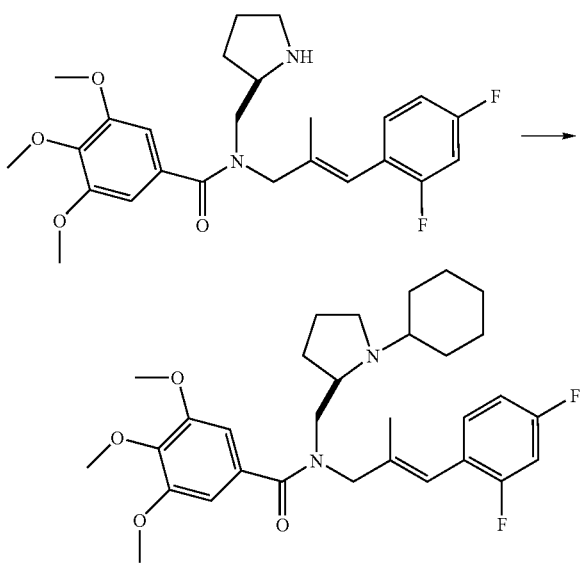

Experimental condition analogous to Example 14 were used with N-(R)-[3-(2,4-difluoro-phenyl)-2-methyl-allyl]-3,4,5-trimethoxy-N-pyrrolidin-2-ylmethyl-benzamide 0.1 g (0.21 mmol), cyclohexanone 0.026 g (0.26 mmol), acetic acid 0.018 ml (0.32 mmol) and sodium cyanoborohydride 0.016 g (0.32 mmol). The free base was converted to the HCl salt, yielding 100 mg of white solid. Yield: 47%.

LC-MSD, m/z for $C_{31}H_{40}F_2N_2O_4$ [M+H]+: 543.5 $^1$H NMR (300 MHz, MeOD): δ 12-2.4 (m, 18H), 3.2-3.5 (m, 2H), 3.5-3.6 (m, 1H), 3.6-3.9 (m, 10H), 4.1-4.4 (m, 3H), 6.4 (s, 1H), 6.9 (s, 2H), 6.9-7.1 (m, 2H), 7.4-7.5 (m, 1H).

Example 48

N-(1-Cyclobutyl-pyrrolidin-2-ylmethyl)-N-[3-(2,4-difluoro-phenyl)-2-methyl-allyl]-3,4,5-trimethoxy-benzamide

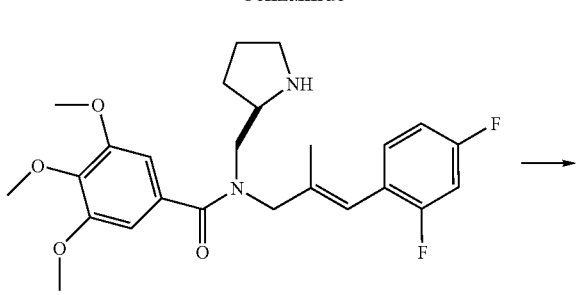

-continued

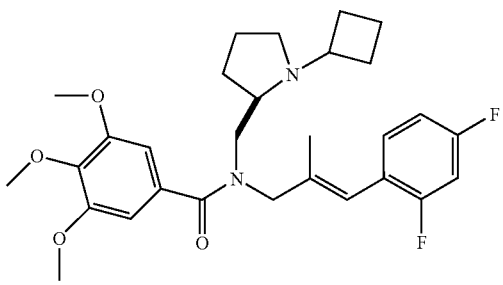

Experimental condition analogous to Example 14 were used with N-(R)-[3-(2,4-Difluoro-phenyl)-2-methyl-allyl]-3,4,5-trimethoxy-N-pyrrolidin-2-ylmethyl-benzamide 0.1 g (0.21 mmol), cyclobutanone 0.019 g (0.26 mmol), acetic acid 0.018 ml (0.32 mmol) and sodium cyanoborohydride 0.016 g (0.32 mmol). The free base was converted to the HCl salt, yielding 110 mg of white solid. Yield: 47%.

LC-MSD, m/z for $C_{29}H_{36}F_2N_2O_4$ [M+H]+: 515.5 $^1$H NMR (300 MHz, MeOD): δ 1.5 (s, 3H), 1.9-2.1 (m, 2H), 2.1-2.4 (m, 4H), 2.4-2.5 (m, 5H), 3.1-3.6 (m, 2H), 3.64.1 (m, 11H), 4.3 (s, 3H), 6.4 (s, 1H), 6.9 (s, 2H), 6.9-7.1 (m, 2H), 7.4-7.5 (m, 1H).

Example 49

3,5-Dimethoxy-N-(S)-(2-methyl-3-phenyl-allyl)-N-pyrrolidin-2-ylmethyl-benzamide

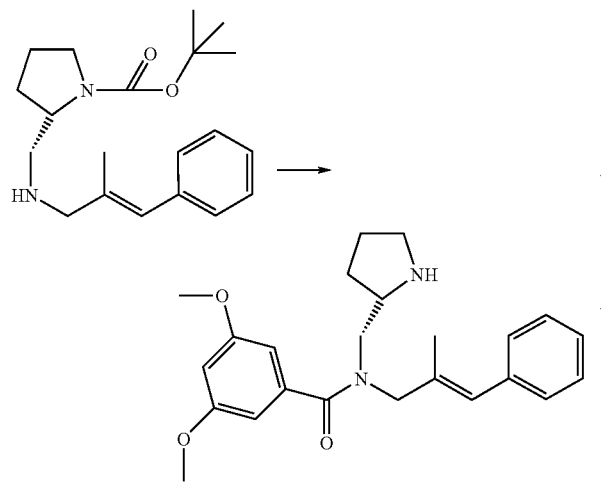

Experimental condition analogous to Example 2 were used with 2-[(2-methyl-3-phenyl-allylamino)-methyl]-(S)-pyrolidine-1-carboxylic acid-tert-butyl ester 0.09 g (0.27 mmol), 3,5 dimethoxybenzoic acid 0.075 g (0.4 mmol), 1-ethyl-3-(dimethylaminopropyl)carbodiimide hydrochloride 0.078 g (0.4 mmol), 1-hydroxybenzotriazole 0.04 g (0.4 mmol) and triethylamine 0.05 ml, in 3 ml tetrahydrofuran. The reaction yielded 88 mg of yellow oil. This oil was dissolved in 1 ml dichloromethane and 0.14 ml of trifluoroacetic acid. The mixture was purified using reverse phase HPLC with a gradient of acetonitrile 20-80% in 40 minutes. The compound was converted to HCl salt, giving 48 mg of a light yellow oil.

LC-MSD, m/z for $C_{24}H_{30}N_2O_3$ [M+H]+: 395.2 $^1$H NMR (400 MHz, CDCl$_3$): δ 1.6-1.8 (m, 3H), 2.0-2.6 (m, 7H), 3.2-3.4 (m, 3H), 3.8 (s, 6H), 4.0-4.4 (s, 4H), 6.18 (s, 1H), 6.25 (s, 1H), 6.6-6.7 (m, 2H), 7.0-7.2 (m, 5H).

Example 50

N-(S)-(1-Cyclohexylmethyl-pyrrolidin-2-ylmethyl)-3,5-dimethoxy-N-(2-methyl-3-phenyl-allyl)-benzamide

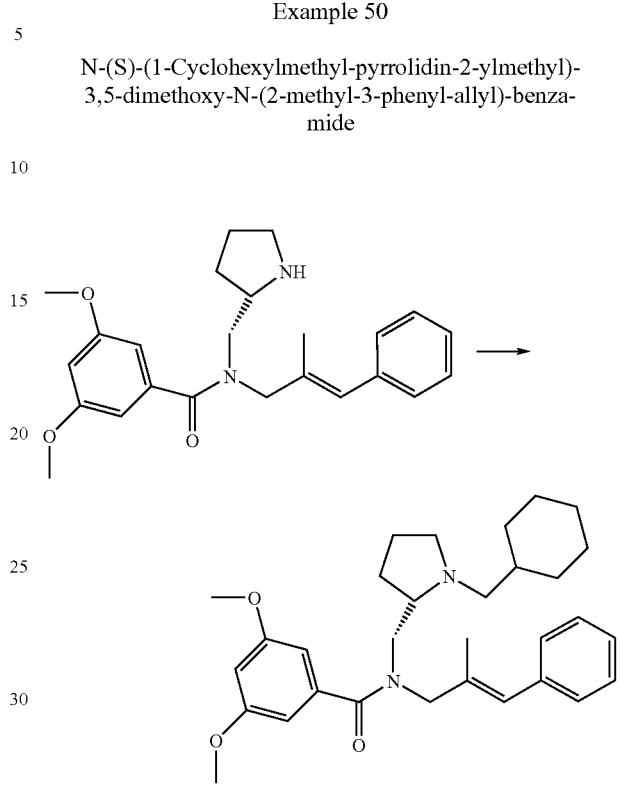

A mixture of 3,5-Dimethoxy-N-(S)-(2-methyl-3-phenyl-allyl)-N-pyrrolidin-2-ylmethyl-benzamide 0.04 g (0.1 mmol), cyclohexanecarbaldehyde 0.012 g (0.11 mmol), and sodium triacethoxy borohydride 0.04 mg (0.2 mmol) in 1 ml dichloromethane, was stirred at room temperature under nitrogen. Work up conditions analogous to Example 14 were used.

The mixture was purified using reverse phase HPLC with a gradient of acetonitrile 20-80% in 40 minutes. The compound was converted to HCl salt to give 22 mg of white powder.

LC-MSD, m/z for $C_{31}H_{42}N_2O_3$ [M+H]+: 491.3, [M+2H]: 492.3, [M+3H]: 493.3

Example 51

N-(S)-(1-Cyclohexylmethyl-pyrrolidin-2-ylmethyl)-N-[3-(4-fluoro-phenyl)-2-methyl-allyl]-3,5-dimethoxy-benzamide

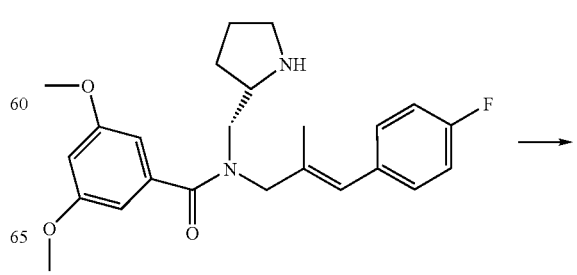

-continued

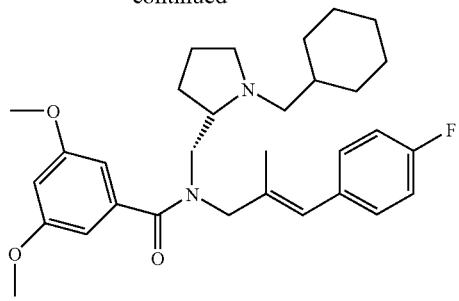

Experimental condition analogous to Example 51 were used with N-[3-(4-fluoro-phenyl)-2-methyl-allyl]-3,5-dimethoxy-N-pyrrolidin-2-ylmethyl-benzamide 0.032 g (0.07 mmol), cyclohexanecarbaldehyde 0.008 g (0.077 mmol), sodium triacethoxy-borohydride, 0.033 g (0.14 mmol). The reaction yielded 25.5 mg of a hydroscopic white compound as a TFA salt. Yield: 58%.

LC-MSD, m/z for $C_{31}H_{41}N_2O_3F$ [M+H]+: 509.2, [M+2H]: 510.2, [M+3H]: 511.2 $^1$H NMR (400 MHz, CDCl$_3$): δ 1.0-1.4 (m, 5H), 1.6-1.8 (m, 5H), 1.9-2.6 (m, 8H), 2.8-3.3 (m, 5H), 3.8 (s, 6H), 3.9-4.2 (m, 4H), 6.22 (s, 1H), 6.4-6.6 (m, 2H), 6.9-7.1 (m, 2H), 7.15-7.25 (m, 3H).

Example 52

N-(R)-(1-Cyclohexylmethyl-pyrrolidin-2-ylmethyl)-N-[3-(2,4-difluoro-phenyl)-2-methyl-allyl]-3,5-dimethoxy-benzamide

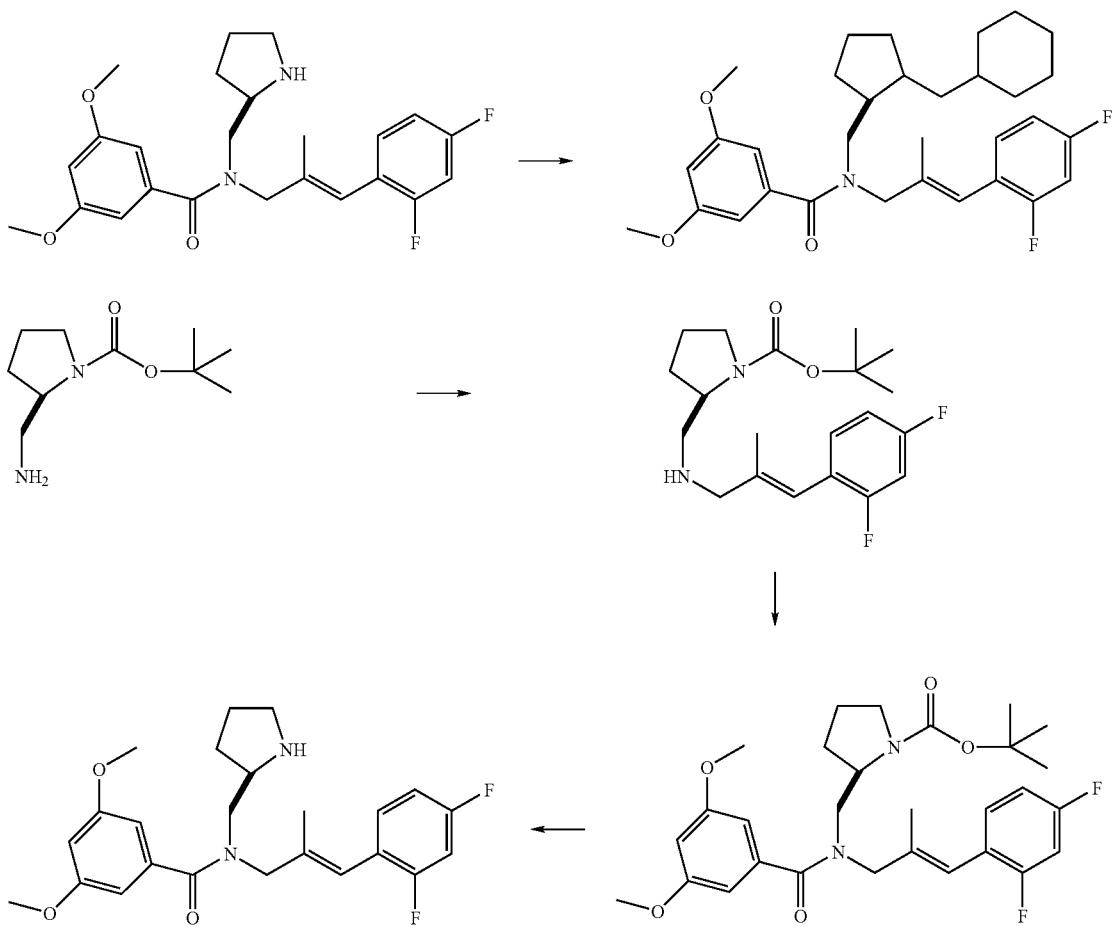

Scheme 15: Preparation of N-[3-(2,4-difluoro-phenyl)-2-methyl-allyl]-3,5-dimethoxy-N-(R)-pyrrolidin-2-ylmethyl-benzamide Experimental condition analogous to Example 51 were used with N-[3-(2,4-difluoro-phenyl)-2-methyl-allyl]-3,5-dimethoxy-N-(R)-pyrrolidin-2-ylmethyl-benzamide (prepared according to the scheme 15) 0.13 g (0.32 mmol), cyclohexane carboxaldehyde 0.039 g (0.35 mmol), and sodiumtriacethoxyborohydride 0.1 g (0.48 mmol). The compound was purified with reverse phase HPLC, with a gradient of 20 to 80% of acetonitrile. The purified compound converted to the HCl salt to yield 80 mg of white powder. Yield: 44%.

LC-MSD, m/z for $C_{31}H_{40}N_2O_3F_2$ [M+H]+: 527.2, [M+2H]: 528.2, [M+3H]: 529.2

Example 53

N-(R)-(1-Cyclohexylmethyl-pyrrolidin-2-ylmethyl)-N-[3-(2,4-difluoro-phenyl)-2-methyl-allyl]-3,5-diethoxybenzamide

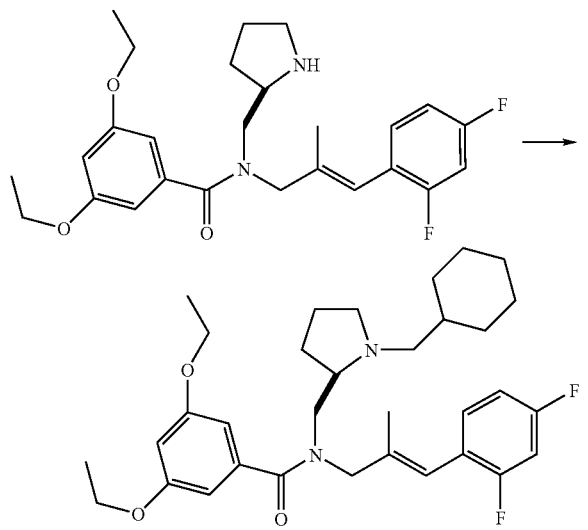

Experimental condition analogous to Example 51 were used with N-[3-(2,4-difluoro-phenyl)-2-methyl-allyl]-3,5-diethoxy-N-(R)-pyrrolidin-2-ylmethyl-benzamide 0.13 g (0.29 mmol), cyclohexane carboxaldehyde 0.037 g (0.31 mmol), and sodiumtriacethoxy-borohydride 0.09 g (0.43 mmol). The compound was purified with reverse phase HPLC, with a gradient of 20 to 80% of acetonitrile. The purified compound was converted to the HCl salt, yielding 30 mg of white powder. Yield: 16%.

LC-MSD, m/z for $C_{33}H_{44}N_2O_3F_2$ [M+H]+: 555.2, [M+2H]: 556.3.2, [M+3H]: 557.2

Example 54

N-(R)-(1-Cyclohexylmethyl-pyrrolidin-2-ylmethyl)-N-[3-(2,4-difluoro-phenyl)-2-methyl-allyl]-3,4,5-trimethoxybenzamide

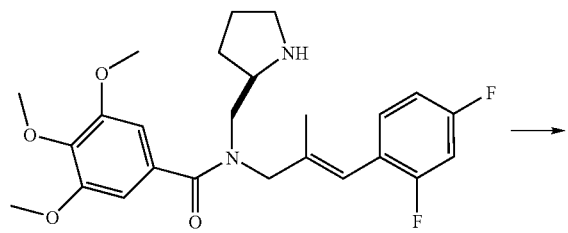

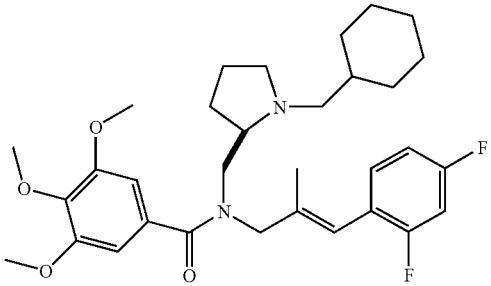

Experimental condition analogous to Example 51 were used with N-[3-(2,4-difluoro-phenyl)-2-methyl-allyl]-3,4,5-trimethoxy-N-(R)-pyrrolidin-2-ylmethyl-benzamide 0.16 g (0.35 mmol), cyclohexane carboxaldehyde 0.041 g (0.38 mmol), and sodium triacethoxy-borohydride 0.11 g (0.52 mmol). The compound was purified with reverse phase HPLC, with a gradient of 20 to 80% of acetonitrile. The purified compound was converted to the HCl salt to yield 100 mg of white powder. Yield: 48%.

LC-MSD, m/z for $C_{32}H_{42}N_2O_4F_2$ [M+H]+: 557.2, [M+2H]: 558.2, [M+3H]: 559.2 $^1$H NMR (400 MHz, CDCl$_3$): δ 1.0-1.4 (m, 7H), 1.5-2.0 (m, 7H), 2.0-2.6 (m, 8H), 3.6-3.9 (s, 9H), 4.0-4.5 (m, 4H), 6.22-6.7 (m, 6H)

Example 55

N-(1-Cyclohexylmethyl-pyrrolidin-2-ylmethyl)-N-[3-(2,4-difluoro-phenyl)-2-methyl-allyl-3,5-diethoxybenzamide

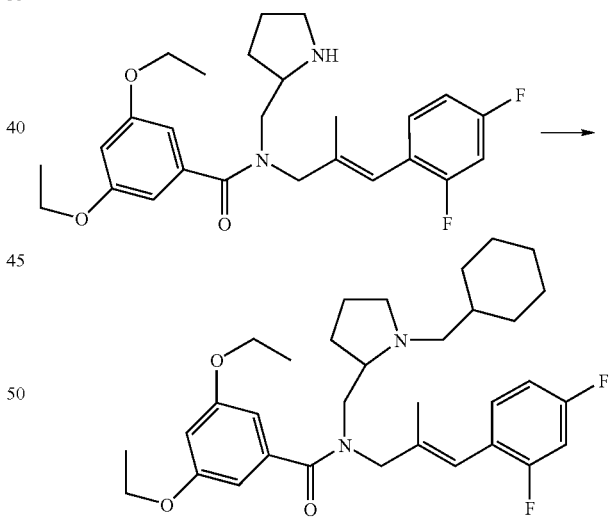

Experimental condition analogous to Example 51 were used with N-[3-(2,4-difluoro-phenyl)-2-methyl-allyl]-3,5-diethoxy-N-pyrrolidin-2-ylmethyl-benzamide 0.15 g (0.35 mmol), cyclohexane carboxaldehyde 0.043 g (0.38 mmol), and sodium triacethoxyborohydride 0.11 g (0.52 mmol). The compound was purified with reverse phase HPLC with a gradient of 20 to 80% of acetonitrile. The purified compound was converted to the HCl salt to yield 50 mg of white powder. Yield: 24%.

LC-MSD, m/z for C33H44N2O3F2 [M+H]+: 555.2, [M+2H]: 556.2, [M+3H]: 557.2

Example 56
N-[1-(S)-(1-Cyclohexyl-ethyl)-pyrrolidin-2-ylmethyl]-N-[3-(2,4-difluoro-phenyl)-2-methyl-allyl]-3,4,5-trimethoxy-benzamide methoxy benzoic acid 0.16 g (0.79 mmol), thionyl chloride 0.1 ml (1.3 mmol), and triethylamine 0.1 ml. After purification the reaction yielded the free amine, which was then converted to 22 mg of HCl salt as a white semi-solid.

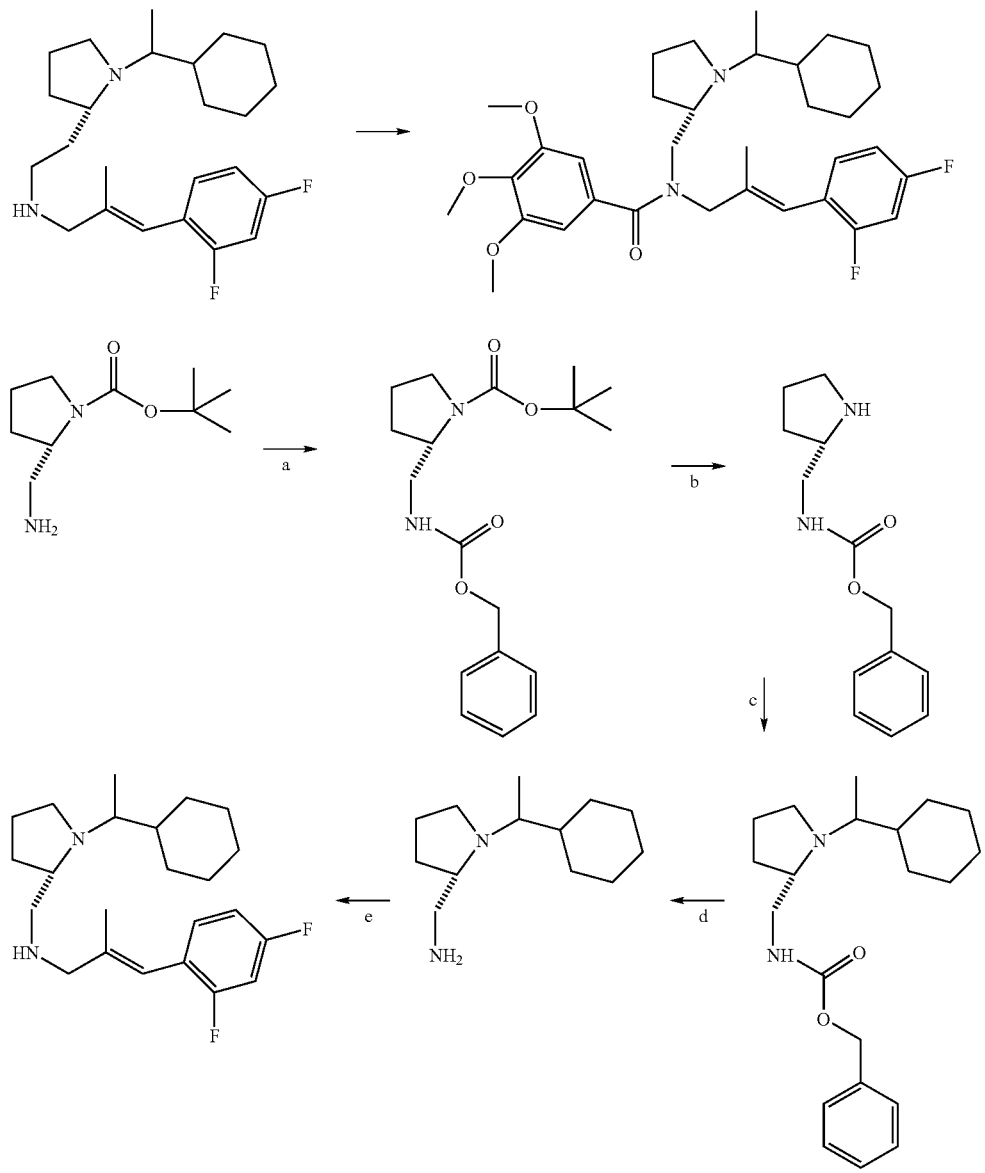

Scheme 16: Preparation of [1-(S)-(1-cyclohexyl-ethyl)-pyrrolidin-2-ylmethyl]-[3-(2,4-difluoro-phenyl)-2-methyl-allyl]-amine a: Benzylchloroformate, sodium carbonate, THF, 3 h, RT
b: 6N HCl, dioxane, 14 h, RT
c: Cyclohexylmethylketone, methanol, acetic acid, sodiumcyanoborohydride, 0° C. to RT
d: 10% Pd/ charcoal, methanol, $H_2$ 2.5 Kg for 5h
e: 1/ 3-(3,5-Dimethyl-phenyl)-propenal
   2/ Sodium borohydride, methanol, 15 min 0° C.

Experimental condition analogous Example 18 were used with [1-(S)-(1-cyclohexyl-ethyl)-pyrrolidin-2-ylmethyl]-[3-(2,4-difluoro-phenyl)-2-methyl-allyl]-amine (prepared according to scheme 16) 0.25 g (0.66 mmol), 3,4,5-tri- LC-MSD, m/z for $C_{33}H_{44}N_2O_4F_2$ [M+H]+: 571.5 $^1$H NMR (300 MHz, MeOD): δ 1.33 (s, 9H), 1.39-1.46 (m, 4H), 1.76-1.88 (m, 8H), 2.19 (s, 4H), 2.1-2.2 (m, 1H), 3.84-3.86 (m, 9H), 4.0-4.1 (m, 1H), 4.277 (m, 2H) 6.2 (s, 1H), 6.95 (s, 2H), 7.03 (m, 2H), 7.2-7.5 (m, 1H).

Example 57

N-[1-(S)-(1-Cyclohexyl-ethyl)-pyrrolidin-2-ylmethyl]-4-difluoromethoxy-N-[3-(2,4-difluoro-phenyl)-2-methyl-allyl]-3-methoxy-benzamide

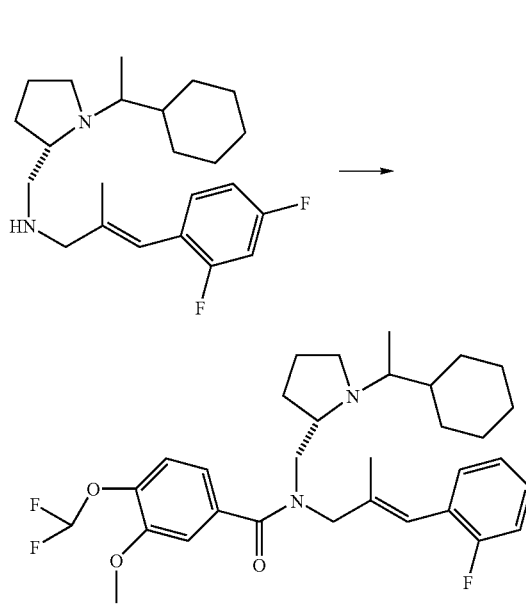

Experimental condition analogous to Example 3 were used with [1-(S)-(1-cyclohexyl-ethyl)-pyrrolidin-2-ylmethyl]-[3-(2,4-difluoro-phenyl)-2-methyl-allyl]-amine 0.13 g (0.37 mmol), 4-difluoromethoxy-3-methoxy-benzoic acid 0.10 g (0.40 mmol), triethylamine 0.07 ml and 1-propanephosphonic acid cyclic anhydride (50% in ethyl acetate) 0.49 ml. After purification, the reaction yielded the free amine, which was then converted to 21 mg of the HCl salt as a white solid. Yield: 10%.

Analytical $C^{18}$ HPLC using 20-95% acetonitrile gradient in 20 minute, elute at 18.00 minutes. LC-MSD, m/z for $C_{32}H_{40}N_2O_3F_4$ [M+H]+: 577.2, [M+2H]: 578.2, [M+3H]: 579.2 $^1$H NMR (400 MHz, MeOD): δ 0.8-0.9 (m, 1H), 1.0-1.4 (m, 8H), 1.5-2.4 (m, 11H), 3.2-3.4 (m, 4H), 3.6-4.0 (m, 5H), 4.0-4.4 (m, 3H), 6.4 (s, 1H), 6.6-7.4 (m, 7H)

Example 58

7-Methoxy-2,2-dimethyl-benzo[1,3]dioxole-5-carboxylic acid [1-(1-cyclohexyl-ethyl)-pyrrolidin-2-ylmethyl]-[3-2,4-difluoro-phenyl)-2-methyl-allyl]-amide

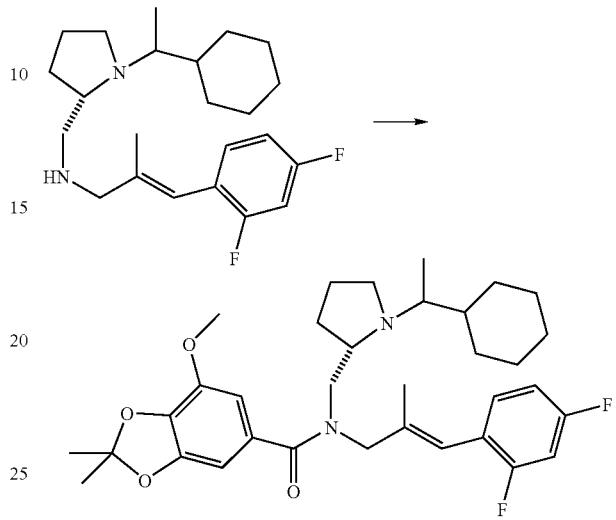

Experimental condition analogous to Example 3 were used with [1-(S)-(1-cyclohexyl-ethyl)-pyrrolidin-2-ylmethyl]-[3-(2,4-difluoro-phenyl)-2-methyl-allyl]-amine 0.13 g (0.37 mmol), 7-methoxy-2,2-dimethyl-benzo[1,3]dioxole-5-carboxylic acid 0.10 g (0.40 mmol), triethylamine 0.07 ml and 1-propanephosphonic acid cyclic anhydride (50% in ethyl acetate) 0.49 ml. After purification, the reaction yielded the free amine, which was then converted to 92 mg of the HCl salt as a white solid. Yield: 40%.

Analytical $C^{18}$ HPLC using 20-95% acetonitrile gradient in 20 minute, elute at 18.92 minutes. LC-MSD, m/z for $C_{34}H_{44}N_2O_4F_4$ [M+H]+: 583.2, [M+2H]: 584.2, [M+3H]: 585.2 $^1$H NMR (400 MHz, MeOD): δ 1.05-1.45 (m, 7H), 1.6-2.4 (m, 15H), 3.2-3.5 (m m, 8H), 3.6-4.0 (m, 4H), 4.2-4.4 (m, 2H), 6.4 (s, 1H), 6.7-7.4 (m, 7H), 6.8 (d, 2H), 6.9-7.2 (m, 2H), 7.3-7.4 (m, 1H).

Example 59

N-(S)-(1-Cyclohexylmethyl-pyrrolidin-2-ylmethyl)-N-[3-(2,4-difluoro-phenyl)-2-methyl-allyl]-3,4,5-trimethoxy-benzamide Scheme 17: Preparation of [1-(S)-(1-cyclohexylmethyl)-pyrrolidin-2-ylmethyl]-[3-(2,4-difluoro-phenyl)-2-methyl-allyl]-amine

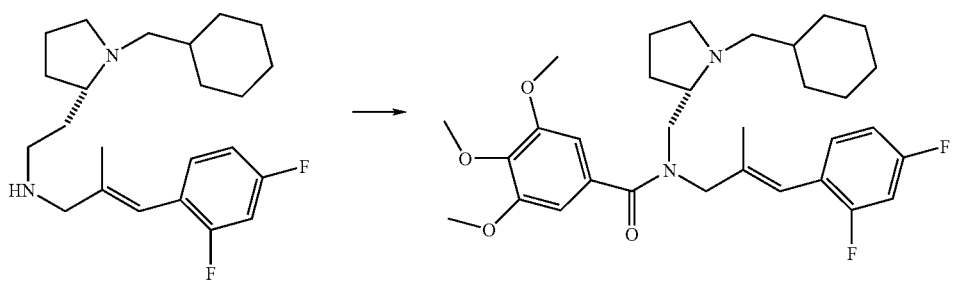

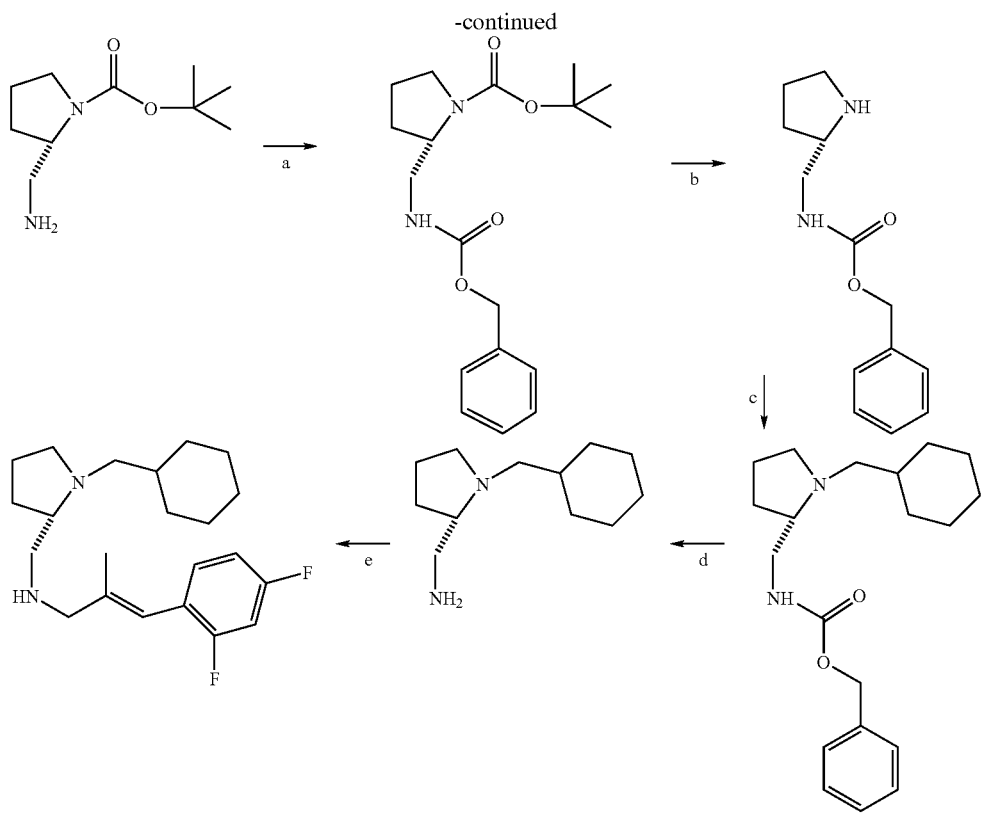

a: Benzylchloroformate, sodium carbonate, THF, 3 h, RT
b: 6N HCl, dioxane, 14 h, RT
c: Cyclohexone carboxaldehyde, methanol, acetic acid, sodiumcyanoborohydride, 0° C. to RT
d: 10% Pd/ charcoal, methanol, H₂ 2.5 Kg for 5h
e: 1/ 3-(3,5-Dimethyl-phenyl)-propenal
  2/ Sodium borohydride, methanol, 15 min 0° C.

Experimental condition analogous to Example 12 were used with [1-(S)-(1-cyclohexylmethyl)-pyrrolidin-2-ylmethyl]-[3-(2,4-difluoro-phenyl)-2-methyl-allyl]-amine (prepared according to scheme 17) 0.18 g (0.52 mmol), 3,4,5-trimethoxy benzoyl chloride 0.14 g (0.8 mmol), triethylamine 0.13 ml. After purification the reaction yielded the free amine, which was then converted to 110 mg of HCl salt as a white semi-solid. Yield: 36%.

LC-MSD, m/z for C32H42N2O4F2 [M+H]+: 557.2, [M+2H]: 558.2, [M+3H]: 559.2

Example 60

N-(S)-(1-Cyclohexylmethyl-pyrrolidin-2-ylmethyl)-N-[3-(2,4-difluoro-phenyl)-2-methyl-allyl]-3,4-dimethoxy-benzamide

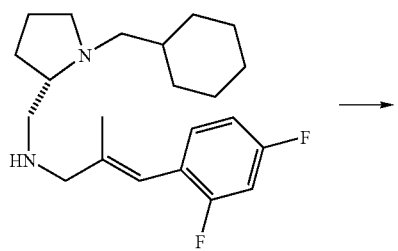

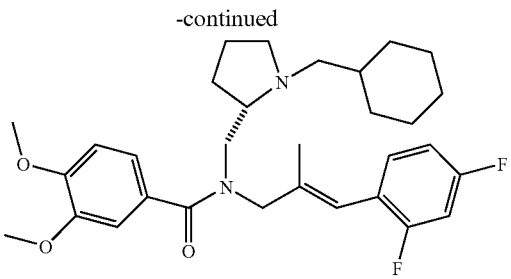

Experimental condition analogous to Example 2 were used with [1-(S)-(1-cyclohexylmethyl)-pyrrolidin-2-ylmethyl]-[3-(2,4-difluoro-phenyl)-2-methyl-allyl]-amine 0.05 g (0.14 mmol) and 3,4,5-trimethoxy benzoic acid 0.037 g (0.21 mmol), triethyl amine 0.03 ml, 1-dimethylaminopropyl-3-ethyl carbodiimide 0.039 g (0.21 mmol) and 1-hydroxybenzotriazole 0.02 g (0.16 mmol). The reaction gave 40 mg of a colorless oil, which was then converted to HCl salt, yielding 22.8 mg of white powder. Yield: 27%.

Analytical $C^{18}$ HPLC using 20-95% acetonitrile gradient in 20 min, the compound elute at 17.535 minutes. LC-MSD, m/z for $C_{32}H_{42}N_2O_4F_2$ [M+H]+: 527.2, [M+2H]: 528.2, [M+3H]: 529.2 ¹H NMR (400 MHz, CDCl₃): δ 0.5-2.1 (m, 20H), 2.4-2.6 (m, 1H), 2.7-3.7 (m, 4H), 3.8-4.5 (m, 4H), 6.2-6.5 (m, 1H), 6.4-6.9 (m, 2H), 7.0-7.5 (m, 4H).

Example 61

N-(S)-(1-Cyclohexylmethyl-pyrrolidin-2-ylmethyl)-3,4-bis-difluromethoxy-N-[3-(2,4-difluoro-phenyl)-2-methyl-allyl]-benzamide

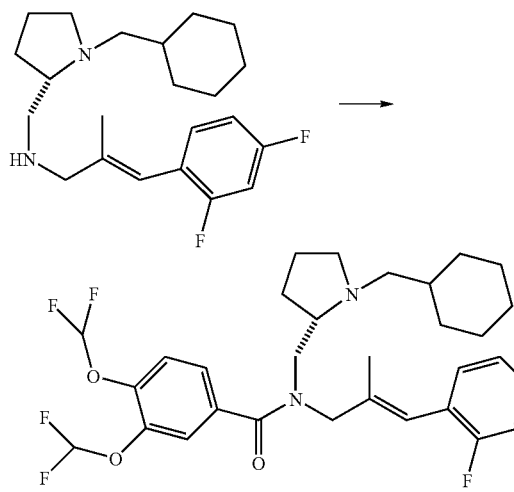

Experimental condition analogous to Example 2 were used with [1-(S)-(1-cyclohexylmethyl)-pyrrolidin-2-ylmethyl]-[3-(2,4-difluoro-phenyl)-2-methyl-allyl]-amine 0.05 g (0.14 mmol) and 3,4-bis-difluoromethoxy-benzoic acid 0.053 g (0.21 mmol), triethylamine 0.03 ml, 1-dimethylaminopropyl-3-ethyl carbodiimide 0.039 g (0.21 mmol) and 1-hydroxybenzotriazole 0.02 g (0.16 mmol). The reaction gave 8.3 mg of a colorless oil, which was then converted to the HCl salt, yielding 4.8 mg of white powder. Yield: 5%.

Analytical $C^{18}$ HPLC using 20-95% acetonitrile gradient in 20 min, the compound elute at 16.969 minutes. LC-MSD, m/z for $C_{31}H_{36}N_2O_3F_6$ [M+H]+: 599.2, [M+2H]: 600.2, [M+3H]: 601.2

Example 62

7-Methoxy-2,2-dimethyl-benzo[1,3]dioxole-5-carboxylic acid-(S)-(1-cyclohexylmethyl-pyrrolidin-2ylmethyl)-[3-(2,4-difluoro-phenyl)-2-methyl-allyl]-amide

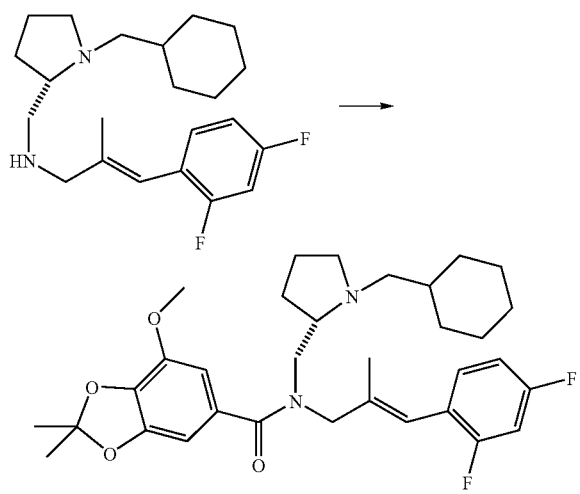

Experimental condition analogous to Example 2 were used with [1-(S)-(1-cyclohexylmethyl)-pyrrolidin-2-ylmethyl]-[3-(2,4-difluoro-phenyl)-2-methyl-allyl]-amine 0.05 g (0.14 mmol) and 7-methoxy-2,2-dimethyl-benzo[1,3]dioxole-5-carboxylic acid 0.049 g (0.21 mmol), triethyl amine 0.03 ml, 1-dimethylaminopropyl-3-ethyl carbodiimide 0.039 g (0.21 mmol) and 1-hydroxybenzotriazole 0.02 g (0.16 mmol). The product was converted to the HCl salt, yielding 27.4 mg white powder. Yield: 32%.

Analytical $C^{18}$ HPLC using 20-95% acetonitrile gradient in 20 min, the compound elute at 18.69 minutes. LC-MSD, m/z for C33H42N2O4F2 [M+H]+: 569.2, [M+2H]: 570.2, [M+3H]: 571.2

Example 63

N-(S)-(1-Cyclohexylmethyl-pyrrolidin-2-ylmethyl)-3-difluoromethoxy-N-[3-(2,4-difluoro-phenyl)-2-methyl-allyl]-4-methoxy-benzamide

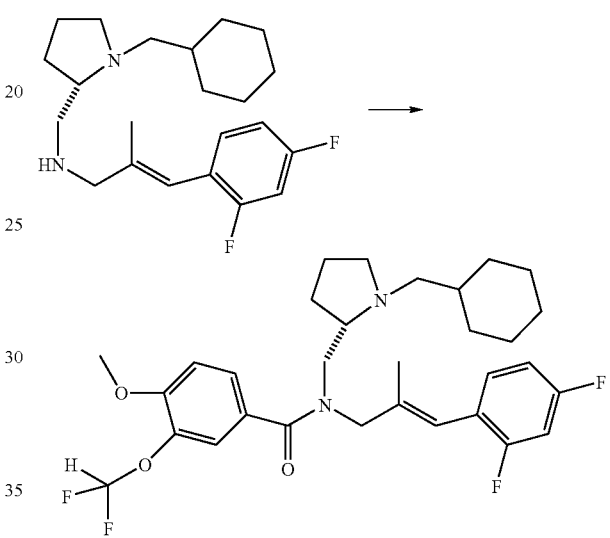

Experimental condition analogous to Example 2 were used with [1-(S)-(1-cyclohexylmethyl)-pyrrolidin-2-ylmethyl]-[3-(2,4-difluoro-phenyl)-2-methyl-allyl]-amine 0.055 g (0.15 mmol), 3-difluoromethoxy-4-methoxy-benzoic acid 0.05 g (0.22 mmol), triethylamine 0.03 ml, 1-dimethylaminopropyl-3-ethyl carbodiimide 0.044 g (0.22 mmol) and 1-hydroxybenzotriazole 0.02 g (0.16 mmol). The resulting free amine was converted to the HCl salt, yielding 21 mg of a very hydroscopic white powder. Yield: 41%.

Analytical $C^{18}$ HPLC using 20-95% acetonitrile gradient in 20 min, the compound elute at 17.99 minutes. LC-MSD, m/z for $C_{31}H_{38}N_2O_3F_4$ [M+H]+: 563.2, [M+2H]: 564.2, [M+3H]: 565.2

Example 64

N-(S)-(1-Cyclohexylmethyl-pyrrolidin-2-ylmethyl)-4-difluoromethoxy-N-[3-(2,4-difluoro-phenyl)-2-methyl-allyl]-4-methoxy-benzamide

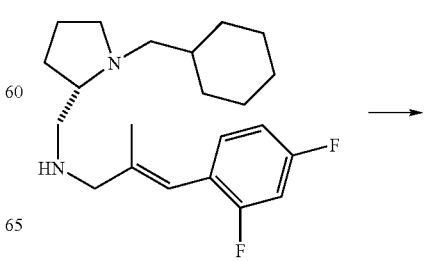

-continued

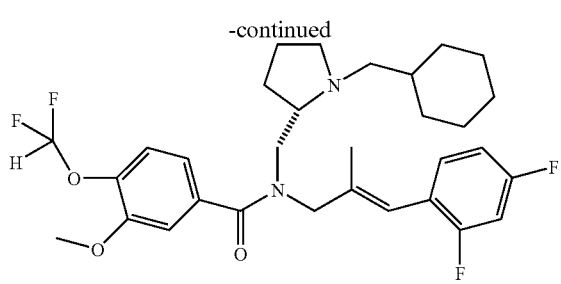

Experimental condition analogous to Example 2 were used with [1-(S)-(1-cyclohexylmethyl)-pyrrolidin-2-ylmethyl]-[3-(2,4-difluoro-phenyl)-2-methyl-allyl]-amine 0.055 g (0.15 mmol), 4-difluoromethoxy-3-methoxy-benzoic acid 0.05 g (0.22 mmol), triethylamine 0.03 ml, 1-dimethylaminopropyl-3-ethyl carbodiimide 0.044 g (0.22 mmol) and 1-hydroxybenzotriazole 0.02 g (0.16 mmol). The free amine was converted to the HCl salt, yielding 21 mg of a very hydroscopic white powder. Yield: 41%.

Analytical $C^{18}$ HPLC using 20-95% acetonitrile gradient in 20 min, the compound elute at 17.81 minutes. LC-MSD, m/z for $C_{31}H_{38}N_2O_3F_4$ [M+H]+: 563.2, [M+2H]: 564.2, [M+3H]: 565.2

Example 65

N-(S)-(1-Cyclohexylmethyl-pyrrolidin-2-ylmethyl)-N-(2-methyl-3-phenyl-allyl)-3,4-bis-(2,2,2-trifluoro-ethoxy)-benzamide Scheme 18: Preparation of (S)-(1-cyclohexyl-pyrrolidin-2-ylmethyl)-(2-methyl-3-phenyl-allyl)-amine

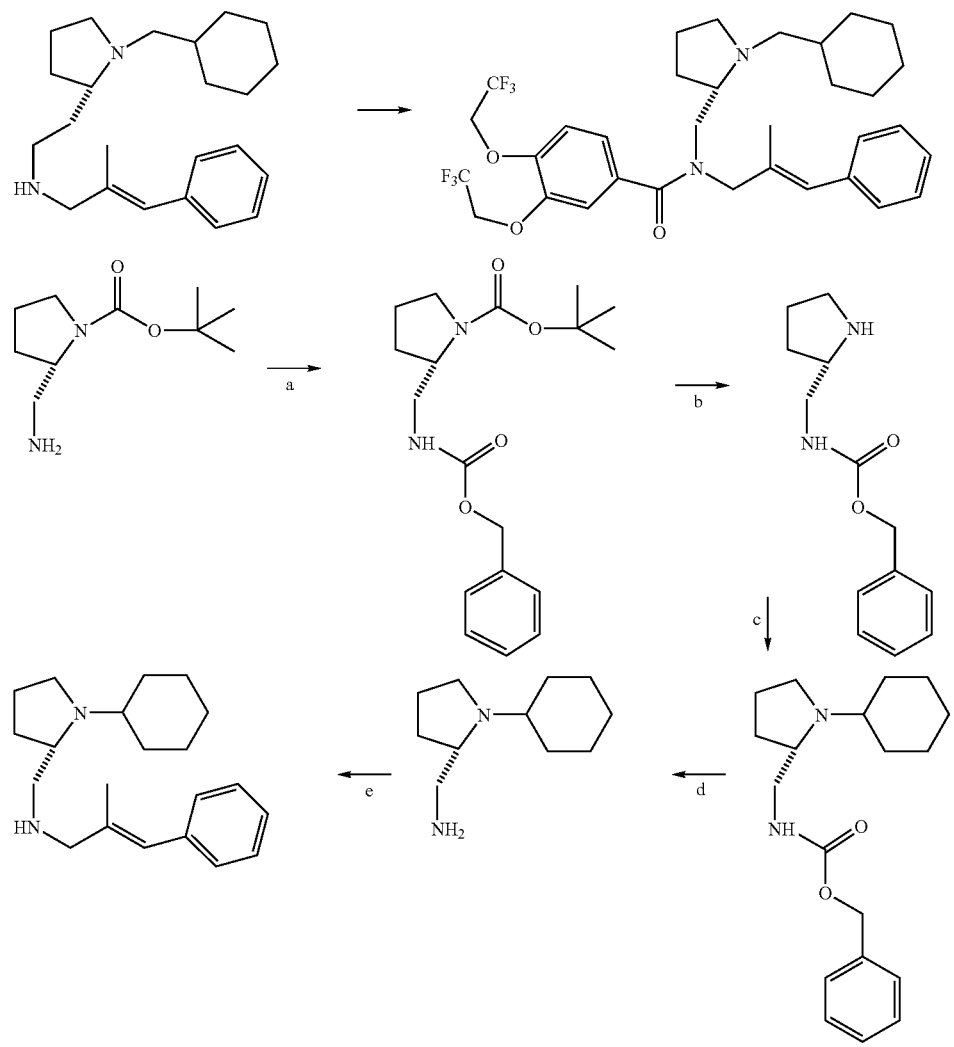

a: Benzylchloroformate, sodium carbonate, THF, 3 h, RT
b: 6N HCl, dioxane, 14 h, RT
c: Cyclohexane, methanol, acetic acid, sodiumcyanoborohydride, 0° C. to RT
d: 10% Pd/charcoal, methanol, $H_2$ 2.5 Kg for 5h
e: 1/ alpha-cinamaldehyde, DCM
   2/ Sodium borohydride, methanol, 15 min 0° C.

Experimental condition analogous to Example 2 were used with (S)-(1-cyclohexylmethyl)-pyrrolidin-2-ylmethyl)-(2-methyl-3-phenyl-allyl)-amine (prepared according to scheme 18) 0.050 g (0.15 mmol), 3,4-Bis-(2,2,2-trifluoroethoxy)-benzoic acid 0.073 g (0.22 mmol), triethyl amine 0.03 ml, 1-dimethylaminopropyl-3-ethyl carbodiimide 0.044 g (0.22 mmol) and 1-hydroxybenzotriazole 0.02 g (0.16 mmol). The reaction yielded 50 mg of a colorless free amine, which was converted to the HCl salt as a white powder. Yield: 50%.

Analytical $C^{18}$ HPLC using 20-95% acetonitrile gradient in 20 min, the compound elute at 18.06 minutes. LC-MSD, m/z for $C_{33}H_{40}N_2O_3F_6$ [M+H]+: 627.2, [M+2H]: 628.2, [M+3H]: 629.2 $^1$H NMR (400 MHz, CDCl$_3$): δ 0.8-2.0 (m, 16H), 2.0-2.4 (m, 4H), 2.6-3.0 (m, 2H), 3.2-3.4 (m, 1H), 3.8-4.5 (m, 8H), 6.4 (s, 1H), 6.9-7.4 (m, 8H)

Example 66

2,3-Dihydro-benzo[1,4]dioxane-6-carboxylic acid (S)-(1-cyclohexylmethyl-pyrrolidin-2-ylmethyl)-(2-methyl-3-phenyl-allyl)-amide

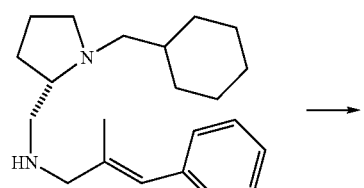

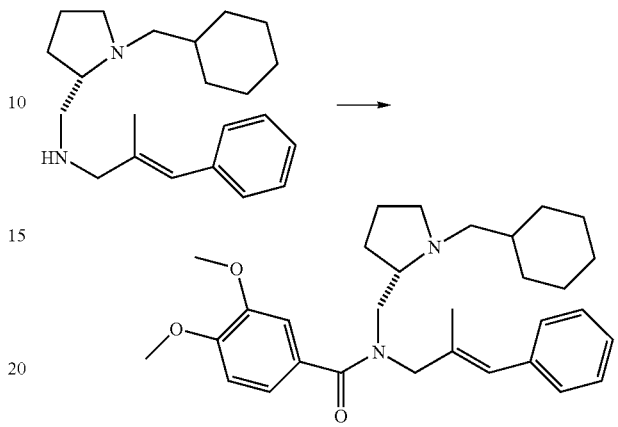

Experimental condition analogous to Example 2 were used with (S)-(1-cyclohexylmethyl)-pyrrolidin-2-ylmethyl)-(2-methyl-3-phenyl-allyl)-amine 0.050 g (0.15 mmol), 2,3-dihydro-benzo[1,4]dioxane-6-carboxylic acid 0.073 g (0.22 mmol), triethyl amine 0.03 ml, 1-dimethylaminopropyl-3-ethyl carbodiimide 0.044 g (0.22 mmol) and 1-hydroxybenzotriazole 0.02 g (0.16 mmol). The reaction yielded 45 mg of colorless free amine, which was converted to the HCl salt as a white powder. Yield: 60%.

Analytical $C^{18}$ HPLC using 20-95% acetonitrile gradient in 20 min, the compound elute at 16.71 minutes. LC-MSD, m/z for $C_{31}H_{40}N_2O_3$ [M+H]+: 489.2, [M+2H]: 490.2, [M+3H]: 491.2 $^1$H NMR (400 MHz, CDCl$_3$): δ 0.8-2.0 (m, 17H), 2.1-2.4 (m, 3H), 2.6-3.0 (m, 2H), 3.5 (s, 1H), 3.8-4.5 (m, 8H), 6.4 (s, 1H), 6.8-7.0 (m, 2H), 7.0-7.4 (m, 5H).

Example 67

N-(S)-(1-Cyclohexylmethyl-pyrrolidin-2-ylmethyl)-3,4-dimethoxy-N-(2-methyl-3-phenyl-allyl)-benzamide

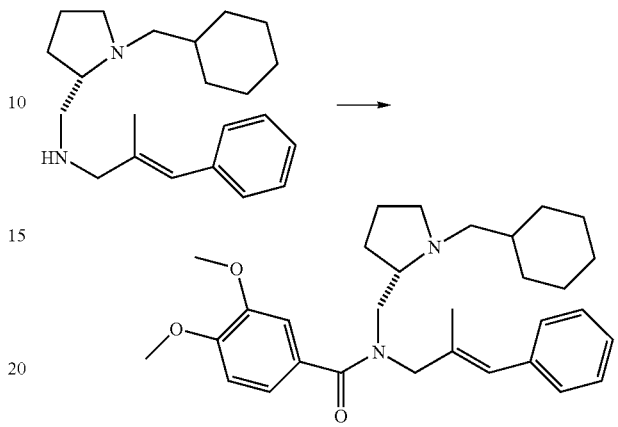

Experimental condition analogous to Example 2 were used with (S)-(1-cyclohexylmethyl)-pyrrolidin-2-ylmethyl)-(2-methyl-3-phenyl-allyl)-amine 0.050 g (0.15 mmol), 3,4-dimethoxybenzoic acid 0.042 g (0.22 mmol), triethylamine 0.03 ml, 1-dimethylaminopropyl-3-ethyl carbodiimide 0.044 g (0.22 mmol) and 1-hydroxybenzotriazole 0.02 g (0.16 mmol). The reaction yielded 34.7 mg of a colorless oil as a free amine, which was converted to the HCl salt as a white powder. Yield: 47%.

Analytical $C^{18}$ HPLC using 20-95% acetonitrile gradient in 20 min, the compound elute at 16.33 minute. LC-MSD, m/z for $C_{31}H_{42}N_2O_3$ [M+H]+: 491.2, [M+2H]: 492.2, [M+3H]: 493.2 $^1$H NMR (400 MHz, CDCl$_3$): δ 0.8-2.0 (m, 21H), 2.7-3.0 (m, 2H), 3.2-3.4 (m, 1H), 3.8 (s, 3H), 3.9 (s, 3H), 4.0-4.5 (m, 3H), 6.4 (s, 1H), 6.9-7.4 (m, 8H).

Example 68

N-(S)-(1-Cyclohexylmethyl-pyrrolidin-2-ylmethyl)-3,4-diethoxy-N-(2-methyl-3-phenyl-allyl)-benzamide

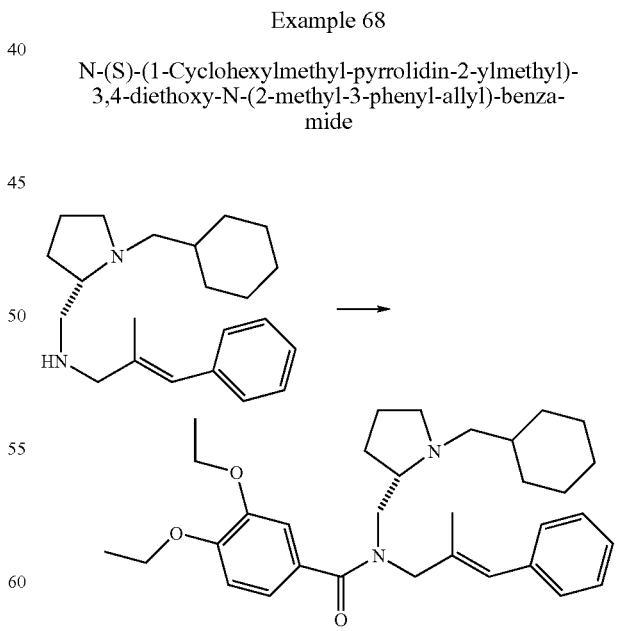

Experimental condition analogous to Example 2 were used with (S)-(1-cyclohexylmethyl)-pyrrolidin-2-ylmethyl)-(2-methyl-3-phenyl-allyl)-amine 0.050 g (0.15 mmol), 3,4-diethoxybenzoic acid 0.048 g (0.22 mmol), triethyl amine 0.03 ml, 1-dimethylaminopropyl-3-ethyl carbodiimide 0.044 g (0.22 mmol) and 1-hydroxybenzotriazole 0.02 g (0.16 mmol). The reaction yielded 40 mg of a colorless oil as a free amine, which was converted to the HCl salt as a white powder. Yield: 51%.

Analytical C[18] HPLC using 20-95% acetonitrile gradient in 20 min, the compound elute at 17.91 minutes. LC-MSD, m/z for $C_{33}H_{46}N_2O_3$ [M+H]+: 519.3, [M+2H]: 520.3, [M+3H]: 521.3 $^1$H NMR (400 MHz, CDCl$_3$): δ 0.8-2.0 (m, 22H), 2.0-2.4 (m, 4H), 2.7-3.0 (m, 2H), 3.3 (s, 1H), 3.8-4.3 (m, 7H), 4.2 (d, 1H), 6.4 (s, 1H), 6.8-7.4 (m, 8H).

Example 69

N-(S)-(1-Cyclohexylmethyl-pyrrolidin-2-ylmethyl)-3,4-diisopropoxy-N-(2-methyl-3-phenyl-allyl)-benzamide

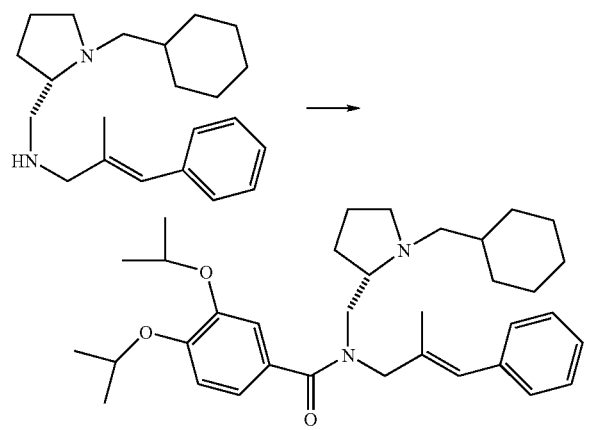

Experimental condition analogous to Example 2 were used with (S)-(1-cyclohexylmethyl)-pyrrolidin-2-ylmethyl)-(2-methyl-3-phenyl-allyl)-amine 0.050 g (0.15 mmol), 3,4-diisopropoxybenzoic acid 0.055 g (0.22 mmol), triethyl amine 0.03 ml, 1-dimethylaminopropyl-3-ethyl carbodiimide 0.044 g (0.22 mmol) and 1-hydroxybenzotriazole 0.02 g (0.16 mmol). The reaction yielded a colorless oil as a free amine, which was converted to HCl salt 22.3 mg as a white powder. Yield: 25%.

LC-MSD, m/z for $C_{35}H_{50}N_2O_3$ [M+H]+: 547.3, [M+2H]: 548.3, [M+3H]: 549.3 $^1$H NMR (400 MHz, CDCl$_3$): δ 1.0-1.4 (m, 12H), 1.4-2.4 (m, 19H), 2.7-3.4 (m, 4H), 3.9-4.6 (m, 6H), 3.8-4.3 (m, 7H), 6.4 (s, 1H), 6.8-7.1 (m, 2H), 7.2-7.4 (m, 6H).

Example 70

7-Methoxy-2,2-dimethyl-benzo[1,3]dioxole-5-carboxylic acid-(S)-(1-cyclohexylmethyl-pyrrolidin-2-ylmethyl)-(2-methyl-3-phenyl-allyl)-amide

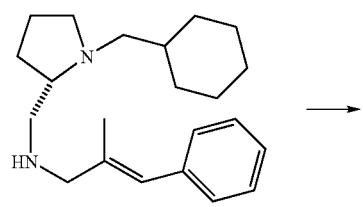

-continued

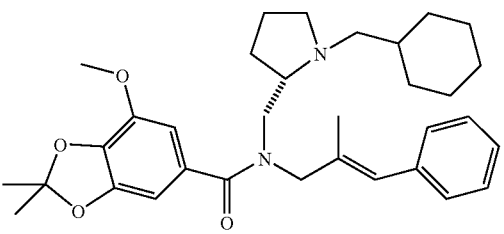

Experimental condition analogous to Example 2 were used with (S)-(1-cyclohexylmethyl)-pyrrolidin-2-ylmethyl)-(2-methyl-3-phenyl-allyl)-amine 0.050 g (0.15 mmol), 7-methoxy-2,2-dimethyl-benzo[1,3]dioxole-5-carboxylic acid 0.055 g (0.22 mmol), triethylamine 0.03 ml, 1-dimethylaminopropyl-3-ethyl carbodiimide 0.044 g (0.22 mmol) and 1-hydroxybenzotriazole 0.02 g (0.16 mmol). The reaction yielded 50 mg of a colorless oil as a free amine, which was converted to HCl salt as a white powder. Yield: 62%.

Analytical C[18] HPLC using 20-95% acetonitrile gradient in 20 min, the compound elute at 20.89 minutes. LC-MSD, m/z for $C_{33}H_{44}N_2O_3$ [M+H]+: 533.3, [M+2H]: 534.3, [M+3H]: 535.3 $^1$H NMR (400 MHz, CDCl$_3$): δ 0.9-1.4 (m, 6H), 1.4-1.9 (m, 15H), 2.0-2.2 (m, 4H), 2.6-3.0 (m, 2H), 3.1-3.2 (m, 1H), 3.8 (s, 3H), 3.9-4.1 (m, 2H), 4.15-4.24 (m, 2H), 4.4-4.5 (m, 1H), 6.4 (s, 1H), 6.5-6.7 (d, 2H), 7.1-7.4 (m, 5H).

Example 71

N-(S)-(1-Cyclohexylmethyl-pyrrolidin-2-ylmethyl)-3-difluoromethoxy-4-methoxy-N-(2-methyl-3-phenyl-allyl)-benzamide

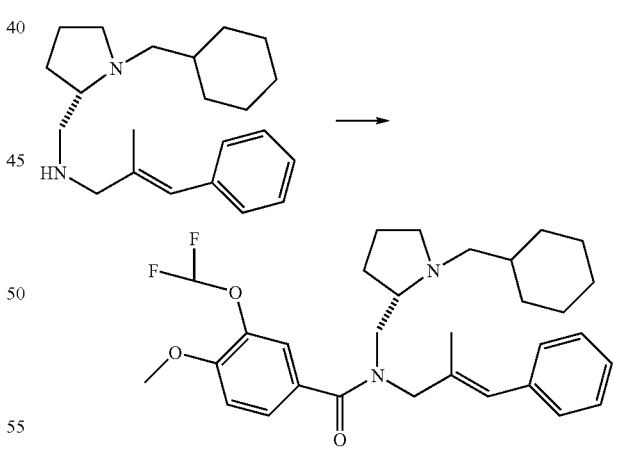

Experimental condition analogous to Example 2 were used with (S)-(1-cyclohexylmethyl)-pyrrolidin-2-ylmethyl)-(2-methyl-3-phenyl-allyl)-amine 0.05 g (0.15 mmol), 3-Difluoromethoxy-4-methoxy-benzoic acid 0.05 g (0.22 mmol), triethyl amine 0.03 ml, 1-dimethylaminopropyl-3-ethyl carbodiimide 0.044 g (0.22 mmol) and 1-hydroxybenzotriazole 0.02 g (0.16 mmol). The reaction yielded free amine, which was converted to the HCl salt 20.7 mg as a yellow powder. Yield: 25%.

Analytical C[18] HPLC using 20-95% acetonitrile gradient in 20 min, the compound elute at 17.62 minute. LC-MSD, m/z for $C_{33}H_{40}N_2O_3F_2$ [M+H]+: 527.2, [M+2H]: 528.2, [M+3H]: 529.2 $^1$H NMR (400 MHz, CDCl$_3$): δ 0.5-2.2 (m, 19H), 2.4-2.6 (m, 1H), 2.8-3.2 (m, 2H), 3.3-3.7 (m, 2H), 3.8 (s, 3H), 3.9 (s, 1H), 4.15-4.24 (m, 2H), 4.4-4.5 (m, 1H), 6.3 (s, 1H), 6.4-7.4 (m, 8H).

Example 72

N-(S)-(1-Cyclohexylmethyl-pyrrolidin-2-ylmethyl)-4-difluoromethoxy-methoxy-N-(2-methyl-3-phenyl-allyl)-benzamide

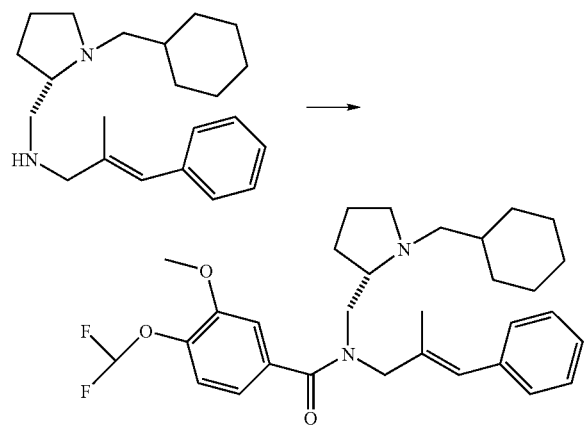

Experimental condition analogous to Example 2 were used with (S)-(1-cyclohexylmethyl)-pyrrolidin-2-ylmethyl)-(2-methyl-3-phenyl-allyl)-amine 0.05 g (0.15 mmol), 3-methoxy-4-difluoromethoxy-benzoic acid 0.05 g (0.22 mmol), triethylamine 0.03 ml, 1-dimethylaminopropyl-3-ethyl carbodiimide 0.044 g (0.22 mmol) and 1-hydroxybenzotriazole 0.02 g (0.16 mmol). The reaction yielded free amine, which was converted to the HCl salt 20.7 mg as a white solid. Yield: 25%.

Analytical C[18] HPLC using 20-95% acetonitrile gradient in 20 min, the compound elute at 17.42 minutes. LC-MSD, m/z for $C_{33}H_{40}N_2O_3F_2$ [M+H]+: 527.2, [M+2H]: 528.2, [M+3H]: 529.2

Example 73

7-Difluoromethoxy-2,2-dimethyl-benzo[1,3]dioxole-5-carboxylic acid (S)-(1-cyclohexylmethyl-pyrrolidin-2-ylmethyl)-(2-methyl-3-phenyl-allyl)-amide

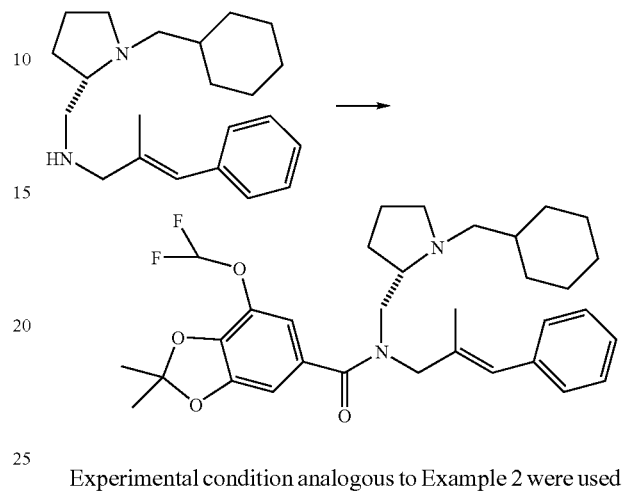

Experimental condition analogous to Example 2 were used with (S)-(1-cyclohexylmethyl)-pyrrolidin-2-ylmethyl)-(2-methyl-3-phenyl-allyl)-amine 0.05 g (0.15 mmol), 7-difluoromethoxy-2,2-dimethyl-benzo[1,3]dioxole-5-carboxylic acid 0.06 g (0.22 mmol), triethylamine 0.03 ml, 1-dimethylaminopropyl-3-ethyl carbodiimide 0.044 g (0.22 mmol) and 1-hydroxybenzotriazole 0.02 g (0.16 mmol). The reaction yielded free amine, which was converted to the HCl salt 25 mg as a white powder. Yield: 27%.

Analytical C[18] HPLC using 20-95% acetonitrile gradient in 20 min, the compound elute at 18.62 minutes. LC-MSD, m/z for $C_{33}H_{42}N_2O_4F_2$ [M+H]+: 569.2, [M+2H]: 570.2, [M+3H]: 571.2 $^1$H NMR (400 MHz, CDCl$_3$): δ 0.9-1.4 (m, 6H), 1.8 (s, 6H), 1.5-1.9 (m, 4H), 1.9-2.4 (m, 3H), 2.6-3.3 (m, 6H), 3.8-4.4 (m, 5H), 6.4 (s, 1H), 6.6-7.4 (m, 7H).

Example 74

2,2-Difluoro-benzo[1,3]dioxole-5-carboxylic acid (S)-(1-cyclohexyl-pyrrolidin-2-ylmethyl)-(2-methyl-3-phenyl-allyl)-amide Scheme 19: Preparation of (S)-(1-cyclohexyl-pyrrolidin-2-ylmethyl)-(2-methyl-3-phenyl-allyl)-amine

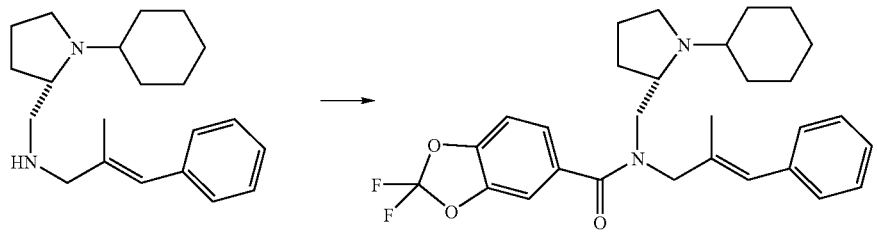

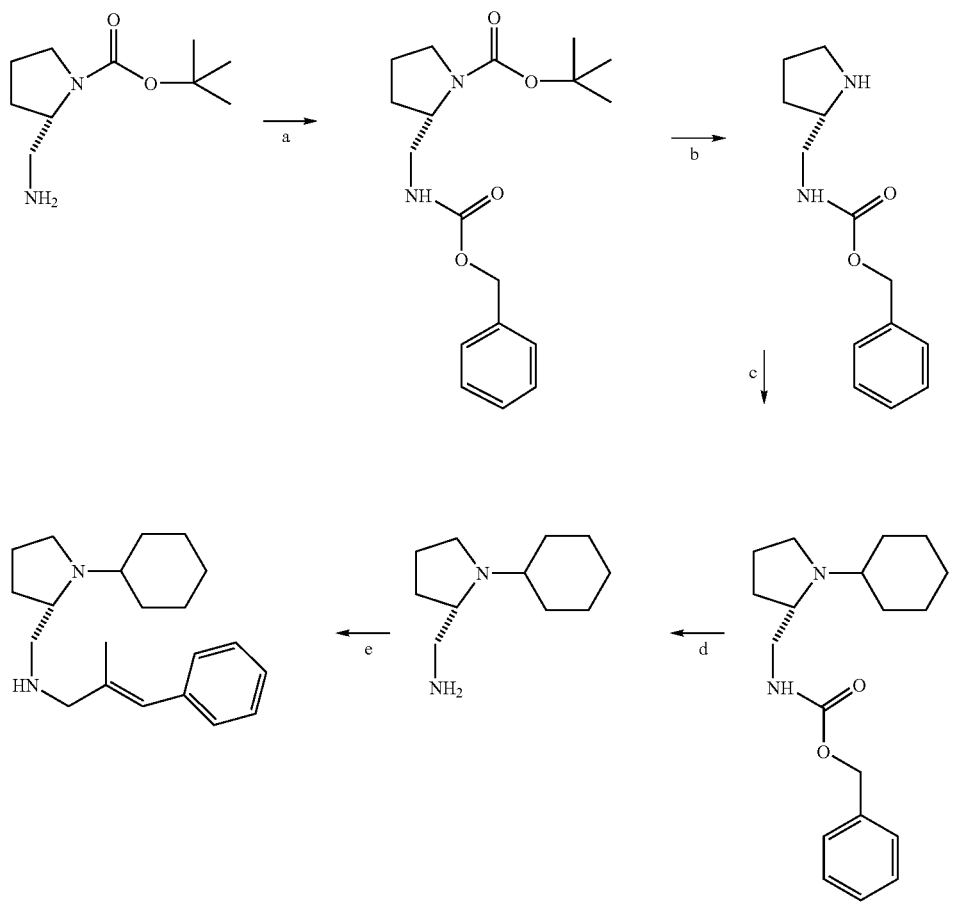

a: Benzylchloroformate, sodium carbonate, THF, 3 h, RT
b: 6 N HCl, dioxane, 14 h, RT
c: Cyclohexanone, methanol, acetic acid, sodiumcyanoborohydride, 0° C. to RT
d: 10% Pd/ charcoal, methanol, $H_2$ 2.5 Kg for 5h
e: 1/ alpha-cinamaldehyde, DCM
   2/ Sodium borohydride, methanol, 15 min 0° C.

Experimental condition analogous to Example 2 were used with (S)-(1-cyclohexyl-pyrrolidin-2-ylmethyl)-(2-methyl-3-phenyl-allyl)-amine (prepared according to scheme 19) 0.050 g (0.16 mmol), 2,2-Difluoro-benzo[1,3]dioxole-5-carboxylic acid 0.042 g (0.20 mmol), triethylamine 0.03 ml, 1-dimethylaminopropyl-3-ethyl carbodiimide 0.037 g (0.24 mmol) and 1-hydroxybenzotriazole 0.02 g (0.19 mmol) and 1 ml THF. The reaction yielded a colorless oil as a free amine, which was converted to the HCl salt 32 mg as yellow powder. Yield: 37%.

Analytical $C^{18}$ HPLC using 20-95% acetonitrile gradient in 20 min, the compound elute at 20.25 minutes. LC-MSD, m/z for $C_{29}H_{34}N_2O_3F_2$ [M+H]+: 497.2, [M+2H]: 498.2, [M+3H]: 499.2 $^1$H NMR (400 MHz, MeOD): δ 1.0-2.4 (m, 15H), 3.2-3.6 (m, 4H), 3.9 (s, 1H), 4.2 (m, 2H), 4.9 (s, 4H), 6.4 (s, 1H), 7.0-7.8 (m, 8H).

Example 75

N-(S)-(1-Cyclohexyl-pyrrolidin-2-ylmethyl)-3,4-dimethoxy-N-(2-methyl-3-phenyl-allyl)-benzamide

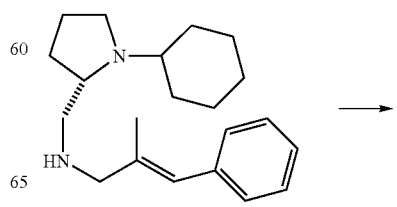

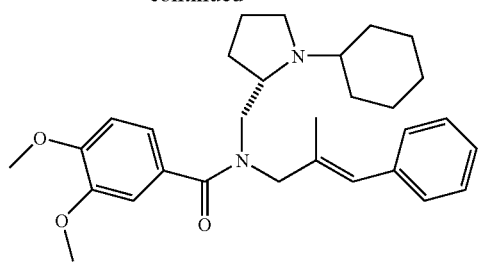

Experimental condition analogous to Example 2 were used with (S)-(1-cyclohexyl-pyrrolidin-2-ylmethyl)-(2-methyl-3-phenyl-allyl)-amine 0.050 g (0.16 mmol), 3,4-dichlorobenzoic acid 0.037 g (0.20 mmol), triethylamine 0.03 ml, 1-dimethylaminopropyl-3-ethyl carbodiimide 0.037 g (0.24 mmol) and 1-hydroxybenzotriazole 0.02 g (0.19 mmol). The reaction yielded a colorless oil as a free amine, which was converted to the HCl salt 20 mg as white powder. Yield: 38%.

Analytical $C^{18}$ HPLC using 20-95% acetonitrile gradient in 20 min, the compound elute at 17.76 minutes. LC-MSD, m/z for $C_{30}H_{40}N_2O_3$ [M+H]+: 477.2, [M+2H]: 478.2, [M+3H]: 479.2

Example 76

7-Methoxy-2,2-dimethyl-benzo[1,3]dioxole-5-carboxylic acid (S)-(1-cyclobutyl-pyrrolidin-2-ylmethyl)-(2-methyl-3-phenyl-allyl)-amide

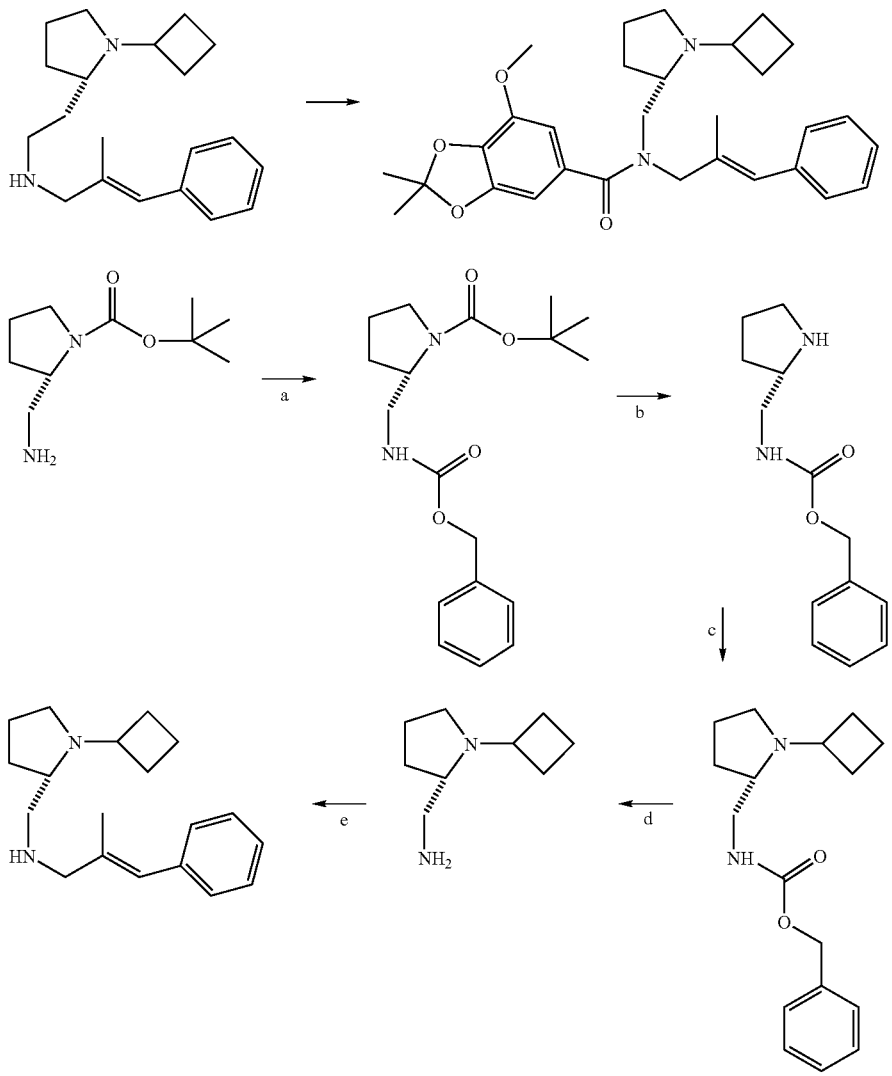

Scheme 20: Preparation of (S)-(1-cyclobutyl-pyrrolidin-2-ylmethyl)-(2-methyl-3-phenyl-allyl)-amine a: Benzylchloroformate, sodium carbonate, THF, 3 h, RT
b: 6 N HCl, dioxane, 14 h, RT
c: Cyclobutanone, methanol, acetic acid, sodiumcyanoborohydride, 0° C. to RT
d: 10% Pd/ charcoal, methanol, $H_2$ 2.5 Kg for 5h
e: 1/ alpha-cinamaldehyde, DCM
   2/ Sodium borohydride, methanol, 15 min 0° C.

Experimental condition analogous to Example 3 were used with 1-(S)-(1-cyclobutyl-pyrrolidin-2-ylmethyl)-(2-methyl-3-phenyl-allyl)-amine (prepared according to scheme 20) 0.1 g (0.37 mmol), 7-methoxy-2,2-dimethyl-benzo[1,3]dioxole-5-carboxylic acid 0.08 g (0.40 mmol), triethylamine 0.07 ml and 1-propanephosphonic acid cyclic anhydride (50% in ethyl acetate) 0.49 ml, gave after purification the free amine, this was then converted to 28.2 mg of HCl salt as a white solid. Yield: 15%

Analytical $C^{18}$ HPLC using 20-95% acetonitrile gradient in 20 minute, elute at 18.69 minutes. LC-MSD, m/z for $C_{30}H_{38}N_2O_4$ [M+H]+: 491.2, [M+2H]: 492.2, [M+3H]: 493.2 $^1$H NMR (400 MHz, CDCl$_3$): δ 1.4-2.2 (m, 15H), 2.2-2.5 (m, 1H), 2.6-3.5 (m m, 5H), 3.8 (s, 3H), 4.2-4.4 (m, 2H), 6.4 (s, 1H), 6.6 (d, 2H), 7.3-7.5 (m, 5H).

Example 77

N-(S)-(1-Cyclobutyl-pyrrolidin-2-ylmethyl)-4-difluoromethoxy-3-methoxy-N-(2-methyl-3-phenyl-allyl)-benzamide

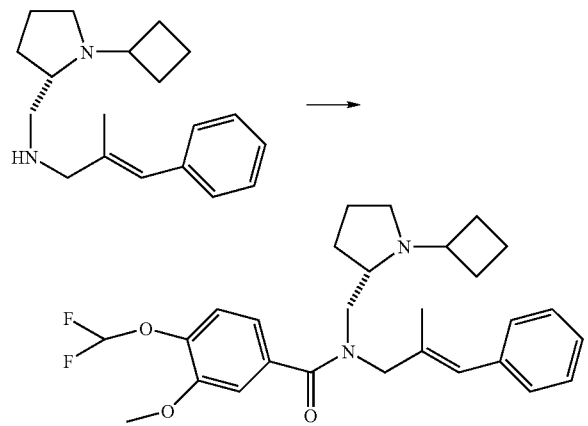

Experimental condition analogous to Example 3 were used with 1-(S)-(1-cyclobutyl-pyrrolidin-2-ylmethyl)-(2-methyl-3-phenyl-allyl)-amine 0.1 g (0.37 mmol), 4-difluoromethoxy-3-methoxy-benzoic acid 0.08 g (0.40 mmol), triethylamine 0.07 ml and 1-propanephosphonic acid cyclic anhydride (50% in ethyl acetate) 0.49 ml, gave after purification the free amine, this was then converted to 26.2 mg of HCl salt as a white solid. Yield: 13%

Analytical $C^{18}$ HPLC using 20-95% acetonitrile gradient in 20 minute, elute at 17.90 minutes. LC-MSD, m/z for $C_{28}H_{34}N_2O_3F_2$ [M+H]+: 485.2, [M+2H]: 486.2, [M+3H]: 487.2 $^1$H NMR (400 MHz, CDCl$_3$): δ 1.4-2.2 (m, 13H), 2.2-2.5 (m, 1H), 2.5-3.4 (m, 4H), 3.5 (s, 1H), 3.8 (m, 3H), 4.0-4.6 (m, 2H), 6.4 (s, 1H), 6.5-7.4 (m, 9H).

Example 78

N-(S)-(1-Cyclobutyl-pyrrolidin-2-ylmethyl)-3,4-dimethoxy-N-(2-methyl-3-phenyl-allyl)-benzamide

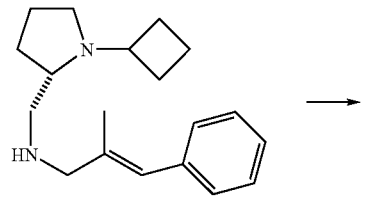

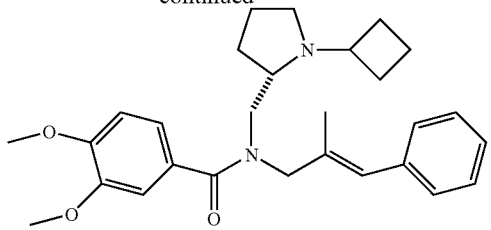

Experimental condition analogous to Example 12 were used with 1-(S)-(1-cyclobutyl-pyrrolidin-2-ylmethyl)-(2-methyl-3-phenyl-allyl)-amine 0.1 g (0.37 mmol), 3,4-dimethoxy benzoyl chloride 0.089 g (0.44 mmol), and triethylamine 0.07 ml, gave after purification the free amine, this was then converted to 51 mg of HCl salt as a white solid. Yield: 28%.

Analytical $C^{18}$ HPLC using 20-95% acetonitrile gradient in 20 minute, elute at 16.55 minutes. LC-MSD, m/z for $C_{28}H_{36}N_2O_3$ [M+H]+: 449.2, [M+2H]: 450.2, [M+3H]: 451.2 $^1$H NMR (400 MHz, CDCl$_3$): δ 1.4-2.4 (m, 13H), 2.3-2.5 (m, 1H), 2.7-3.6 (m, 5H), 3.8-4.0 (m, 6H), 4.2 (m, 2H), 6.4 (s, 1H), 6.8-7.4 (m, 8H).

Example 79

N-(S)-(1-Cyclobutyl-pyrrolidin-2-ylmethyl)-4-difluoromethoxy-N-[3-(2,4-difluoro-phenyl)-2-methyl-allyl]-3-methoxy-benzamide

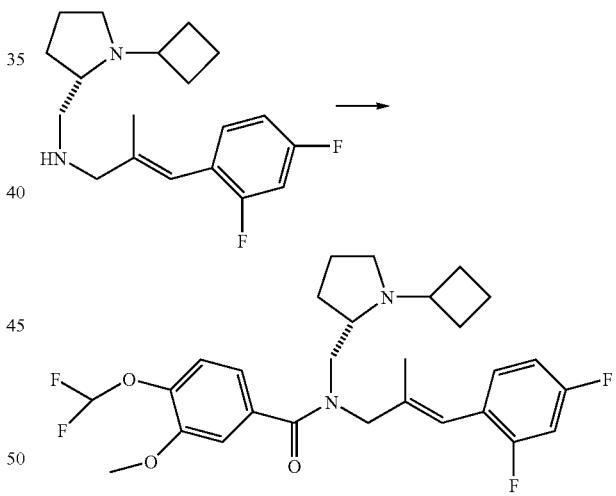

Experimental condition analogous to Example 3 were used with 1-(S)-(1-cyclobutyl-pyrrolidin-2-ylmethyl)-[3-(2,4-difluoro-phenyl)-2-methyl-allyl]-aminomethyl-3-phenyl-allyl)-amine 0.11 g (0.37 mmol), 4-difluoromethoxy-3-methoxy-benzoic acid 0.08 g (0.40 mmol), triethylamine 0.07 ml and 1-propanephosphonic acid cyclic anhydride (50% in ethyl acetate) 0.49 ml, in 5 ml Dichloromethane gave after purification the free amine, this was then converted to 44 mg of HCl salt as a white solid. Yield: 13%.

Analytical $C^{18}$ HPLC using 20-95% acetonitrile gradient in 20 minute, elute at 16.79 minutes. LC-MSD, m/z for $C_{28}H_{32}N_2O_3F_4$ [M+H]+: 527.2, [M+2H]: 528.2, [M+3H]: 529.2 $^1$H NMR (400 MHz, CDCl$_3$): δ 0.8-1.0 (m, 2H), 1.4-1.6 (m, 2H), 1.8-2.0 (m, 3H), 2.0-2.4 (m, 7H), 3.5-4.0 (m, 8H), 4.2 (s, 2H), 6.4 (s, 1H), 6.6-6.4 (m, 7H).

Example 80

N-(1-Ethyl-piperidin-3-yl)-3,4,5-trimethoxy-N-(2-methyl-3-phenyl-allyl)-benzamide Scheme 21: Preparation of (1-ethyl-piperidin-3-yl)-(2-methyl-3-phenyl-allyl)-amine

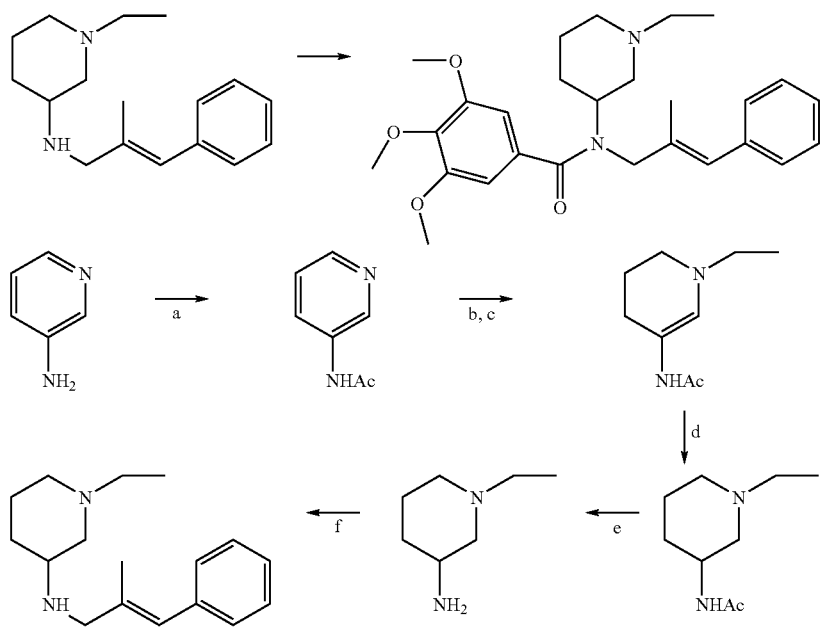

a: Acetic anhydride, RT, then 50° C., 4 h
b: Ethyl iodide, DMF, 65° C., 3 h
c: Sodium borohydride, THF, 0° C. to RT, 14 h
d: 10% Pd/C, methanol, $H_2$ 3Kg pressure, 14 h
e: HCl, 100° C., 14 h,
f: 1/ a-methyl cinnamaldehyde, dichloromethane
2/ Sodium borohydride, methanol Experimental condition analogous to Example 18 were used with (1-ethyl-piperidin-3-yl)-(2-methyl-3-phenyl-allyl)-amine 0.35 g (1.3 mmol), 3,4,5-trimethoxybenzoic acid 0.18 g (0.86 mmol), thionyl chloride 0.39 g, and triethylamine 0.19 ml, in 10 ml of dichlorometane. The reaction yielded 35 mg of free amine, which was converted to the HCl salt as an off-white solid. Yield: 9%.

LC-MSD, m/z for $C_{27}H_{36}N_2O_4$ [M+H]+: 453.3, $^1$H NMR (300 MHz, MeOD): δ 1.2-1.5 (m, 3H), 1.7-2.4 (m, 7H), 3.0 (t, 1H), 3.3-3.4 (m, 2H), 3.6 (d, 2H), 3.6-3.9 (m, 10H), 4.1-4.3 (m, 2H), 4.3-4.4 (m, 1H), 6.4 (s, 1H), 6.8 (s, 2H), 7.2-7.5 (m, 5H).

Example 81

3,4,5-Trimethoxy-N-(2-methyl-3-phenyl-allyl)-N-[3-(3-phenoxy-piperidin-1-yl)-propyl]-benzamide

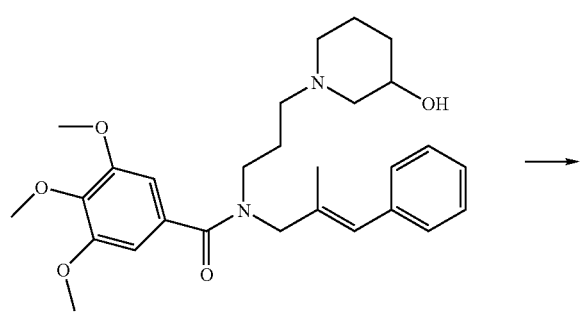

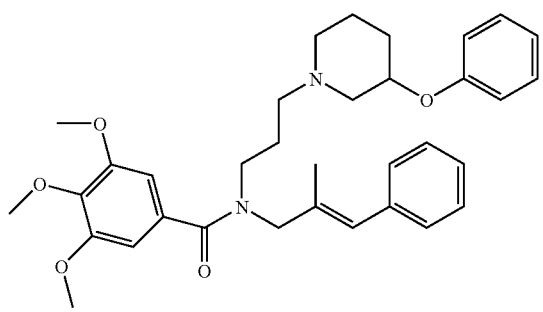

To a solution of N-[3-(3-Hydroxy-piperidin-1-yl)-propyl]-3,4,5-trimethoxy-N-(2-methyl-3-phenyl-allyl)-benzamide 0.2 g (0.41 mmol), and phenol 0.058 g (0.62 mmol) in 10 ml anhydrous dichloromethane, triphenylphosphine 0.16 g (0.6 mmol) was added followed by diethylazodicarboxylate 0.169 (0.6 mmol), at 0° C. The reaction mixture was stirred at room temperature for 18 hr, concentrated and purified by column chromatography over silica gel elution with chloroform and methanol to yield the free amine, which was then converted to the HCl salt, to give 39 mg of a brown semi-solid. Yield: 17%.

LC-MSD, m/z for $C_{34}H_{42}N_2O_5$ [M+H]+: 559.3 $^1$H NMR (300 MHz, MeOD): δ 1.8-1.9 (m, 3H), 2.0-2.5 (m, 6H), 3.4 (m, 2H), 3.5-4.0 (m, 13H), 4.0-4.2 (m, 3H), 4.3-4.5 (m, 2H), 6.4 (s, 1H), 6.8 (s, 2H), 7.0-7.2 (m, 3H), 7.2-7.5 (m, 7H).

Example 82

N-[3-(3-Benzylamino-piperidin-1-yl)-propyl]-3,4,5-trimethoxy-N-(2-methyl-3-phenyl-allyl)-benzamide

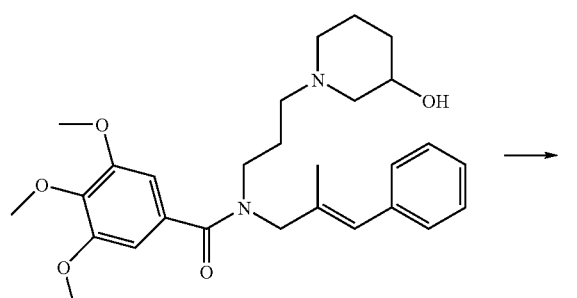

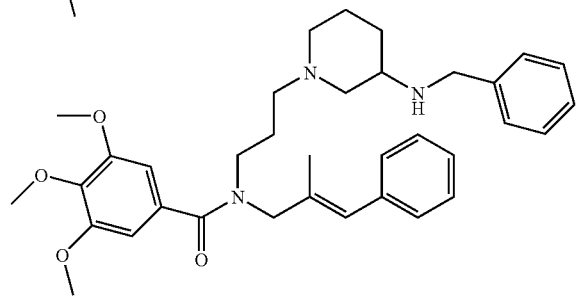

20 ml of anhydrous dichloromethane triethylamine 0.2 ml was added to a solution of N-[3-(3-hydroxy-piperidin-1-yl)-propyl]-3,4,5-trimethoxy-N-(2-methyl-3-phenyl-allyl)-benzamide 0.5 g (1.0 mmol). Thereafter, methane sulfonyl chloride 0.14 g (1.2 mmol) at 0° C. was added. The reaction mixture was stirred for 6 hr, diluted with dichloromethane, and washed with water and brine, yielding the intermediate chlorine 0.4 g (0.8 mmol) as a brown solid.

To this intermediate chlorine 0.15 g (0.29 mmol) in acetonitrile, potassium carbonate 0.12 g (0.8 mmol) was added and was stirred at room temperature for 40 minutes. To this mixture benzylamine 0.03 g (0.29 mmol) was added and the mixture refluxed at 80° C. for 14 hr. Potassium carbonate was filtered off and the filtrate was concentrated. Residue was diluted with chloroform and washed with 1.5 N HCl. Organic layer was dried over anhydrous sodium sulfate, filtrated and concentrated under vacuum. Purification over silica gel, elution with chloroform 9 and methanol 1, yielded the free amine, which was converted to the HCl salt 36 mg as a yellow solid. Yield: 5.9%.

LC-MSD, m/z for $C_{35}H_{45}N_3O_4$ [M+H]+: 572.4 $^1$H NMR (300 MHz, MeOD): δ 1.5-1.7 (m, 3H), 2.0-2.5 (m, 6H), 3.2-3.7 (m, 5H), 3.5-4.0 (m, 12H), 4.0-4.2 (m, 4H), 4.3-4.5 (m, 2H), 6.4 (s, 1H), 6.8 (s, 2H), 7.2-7.6 (m, 10H).

Example 83

N-[3-(3-Isopropylamino-piperidin-1-yl)-propyl]-3,4,5-trimethoxy-N-(2-methyl-3-phenyl-allyl)-benzamide

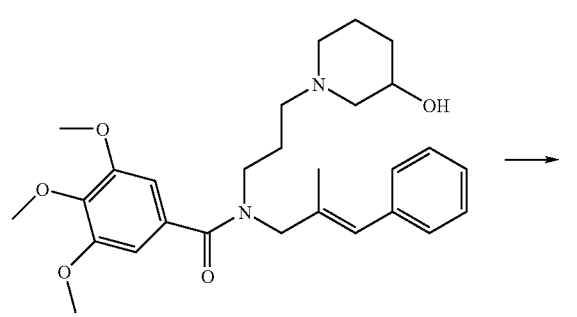

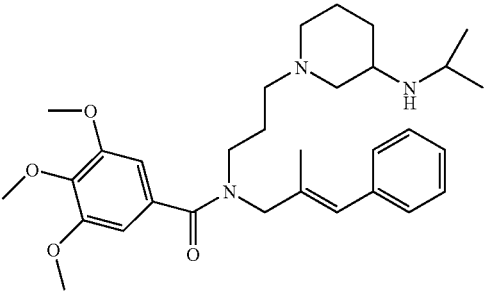

Experiment condition analogous to Example 82 were used with the chlorine intermediate 0.1 g (0.19 mmol), potassium carbonate 0.1 g (0.79 mmol), and isopropylamine 0.23 g (3.9 mmol), in anhydrous acetonitrile. The reaction yielded 45 mg of a brown solid as a HCl salt.

LC-MSD, m/z for $C_{31}H_{45}N_3O_4$ [M+H]+: 524.5 $^1$H NMR (300 MHz, MeOD): δ 1.3-1.5 (m, 7H), 1.7-2.0 (m, 4H), 2.0-2.5 (m, 6H), 2.5-2.7 (m, 1H), 3.4-3.6 (m, 3H), 3.7-4.0 (m, 12H), 4,0-4.3 (m, 4H), 6.4 (s, 1H), 6.8 (m, 2H), 7.2-7.6 (m, 5H).

Example 84

3,4,5-Trimethoxy-N-(2-methyl-3-phenyl-ally)-N-(2-piperidin-1-yl-ethyl)-benzamide

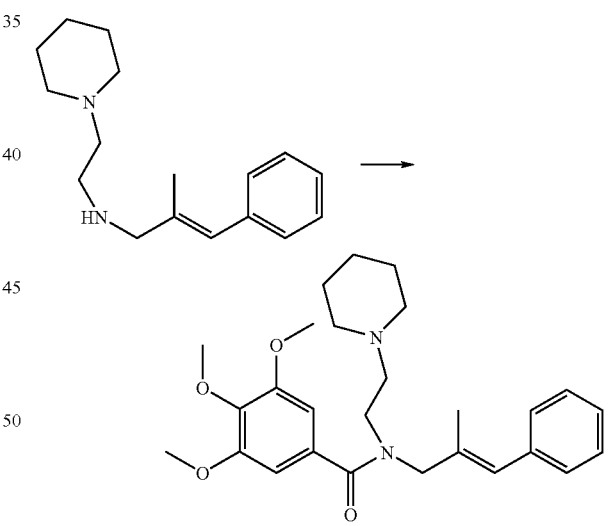

Experimental condition analogous to Example 13 were used with (2-Methyl-3-phenyl-allyl)-(2-piperidin-1-yl-ethyl)-amine, 0.5 g (1.9 mmol), 3,4,5-trimethoxy benzoic acid 0.49 g (2.3 mmol), 0.2 ml of triethylamine, O-(benzotriazol-1-yl)-N,N,N',N'-tetramethyluronium tetrafluoroborate 1.2 g (3.8 mmol). The reaction yielded 102 mg of an off-white solid as an HCl salt. Yield: 12%.

LC-MSD, m/z for $C_{27}H_{36}N_2O_4$ [M+H]+: 453.3. $^1$H NMR (300 MHz, MeOD): δ 1.5-1.6 (m, 3H), 1.7-2.0 (m, 6H), 3.0-3.2 (m, 2H), 3.3-3.5 (m, 3H), 3.6-3.9 (m, 9H), 3.9-4.0 (m, 3H), 4.2 (m, 2H), 6.5 (s, 1H), 6.8 (m, 2H), 7.3-7.5 (m, 5H).

Example 85

N-[3-(3-benzyl-piperidin-1-yl)-propyl]-3,4,5-tri-methoxy-N-(2-methyl-3-phenyl-allyl)-benzamide

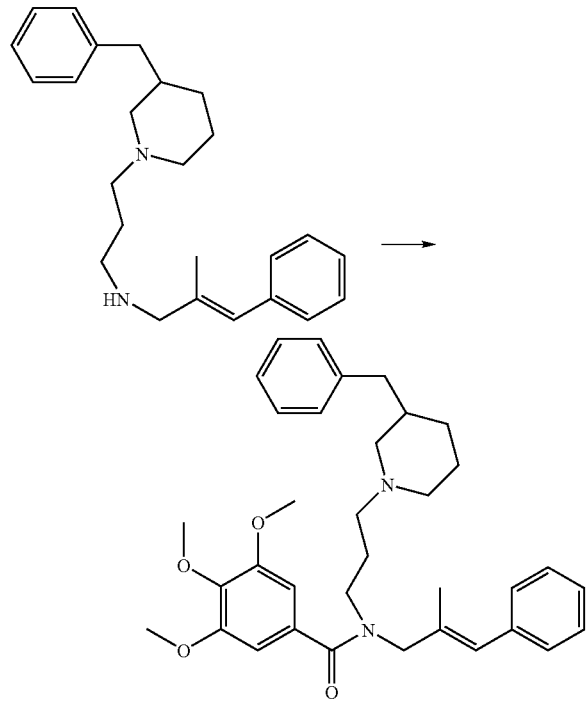

Experiment condition analogous to Example 18 were used with [3-(3-benzyl-piperidin-1-yl)-propyl]-(2-methyl-3-phenyl-allyl)-amine 0.4 g (1 mmol), 1 ml triethylamine, 3,4,5-trimethoxybenzoic acid 0.25 g (1.2 mmol)(transformed to acyl chloride with thionyl chloride 0.24 g (2.2 mmol)) in dichloromethane. The reaction yielded the free amine which was converted to the HCl salt to yield 0.3 g of a white powder. Yield: 50%.

LC-MSD, m/z for $C_{35}H_{44}N_2O_4$ [M+H]+: 557.7 $^1$H NMR (300 MHz, MeOD): δ 1.6-1.9 (m, 5H), 1.9-2.2 (m, 5H), 2.5-2.7 (m, 2H), 2.7-2.9 (m, 2H), 3.1-3.3 (m, 2H), 3.4-3.5 (m, 2H), 3.5-3.7 (m, 2H), 3.7-3.9 (m, 9H), 4.0-4.2 (m, 2H), 6.5 (s, 1H), 6.6-6.8 (m, 2H), 7.1-7.4 (m, 10H).

Example 86

N-(3-Dimethylamino-propyl)-3,4,5-trimethoxy-N-(2-methyl-3-phenyl-ally)-benzamide

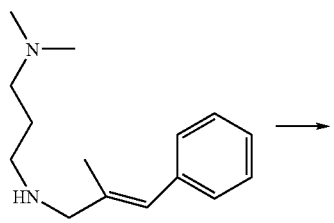

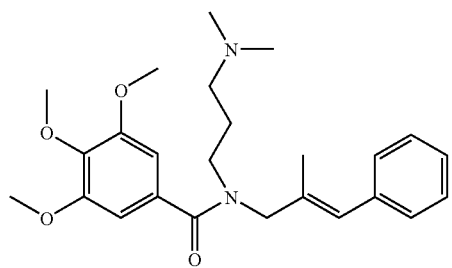

Experimental condition analogous to Example 13 were used with 3,4,5-trimethoxy benzoic acid, 0.65 g (3 mmol), and N,N-Dimethyl-N'-(2-methyl-3-phenyl-ally)-propane-1,3-diamine, 0.6 g (2.5 mmol) and O-(benzotriazole-1-yl)-N,N,N',N'-tetramethyluronium tetrafluoroborate 1.5 g (5 mmol) to give 130 mg of a white solid as a HCl salt. Yield: 13%.

LC-MSD, m/z for $C_{25}H_{34}N_2O_4$ [M+H]+: 427.2. $^1$H NMR (300 MHz, MeOD): δ 1.6 (s, 3H), 2.1-2.3 (m, 3H), 2.7 (m, 1H), 3.8 (s, 6H), 3.2-3.4 (m, 2H), 3.5-3.7 (m, 2H), 3.4-3.8 (m, 9H), 4.1 (s, 2H), 6.5 (s, 1H), 6.8 (m, 2H), 7.1-7.4 (m, 5H).

Example 87

3,4-5-Trimethoxy-N-(2-methyl-3-phenyl-allyl)-N-(3-pyrrolidin-1-yl-propyl)-benzamide

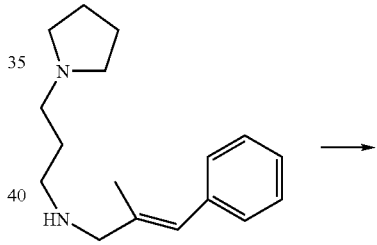

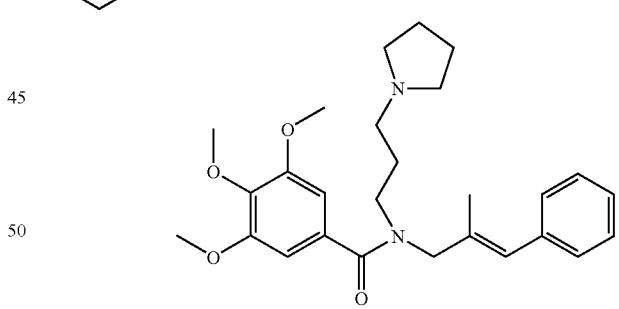

Experimental condition analogous to Example 2 were used with 3,4,5-trimethoxy benzoic acid, 0.4 g (1.9 mmol), (2-Methyl-3-phenyl-allyl)-(3-pyrrolidin-1-yl-propyl)-amine 0.25 g (1.9 mmol), 1-ethyl-3-(3-dimethylaminopropyl)carbodiimide hydrochloride 0.44 g (2.3 mmol), 1-hydroxybenzotriazole 0.26 g (0.19 mmol), and triethylamine 0.3 ml. The reaction yielded 187 mg of a white solid as an HCl salt. Yield: 20%.

LC-MSD, m/z for $C_{27}H_{36}N_2O_4$ [M+H]+: 452.27. $^1$H NMR (300 MHz, MeOD): δ 1.6-1.7 (s, 3H), 2.0-2.3 (m, 7H), 3.0-3.2 (m, 2H), 3.2-3.4 (m, 6H), 3.6-3.8 (m, 12H), 4.1-4.3 (m, 2H), 6.5 (s, 1H), 6.8 (m, 2H), 7.1-7.4 (m, 5H).

Example 88

3,4-5-Trimethoxy-N-(2-methyl-3-phenyl-allyl)-N-[3-(4-phenyl-piperidin-1-yl)-propyl]-benzamide

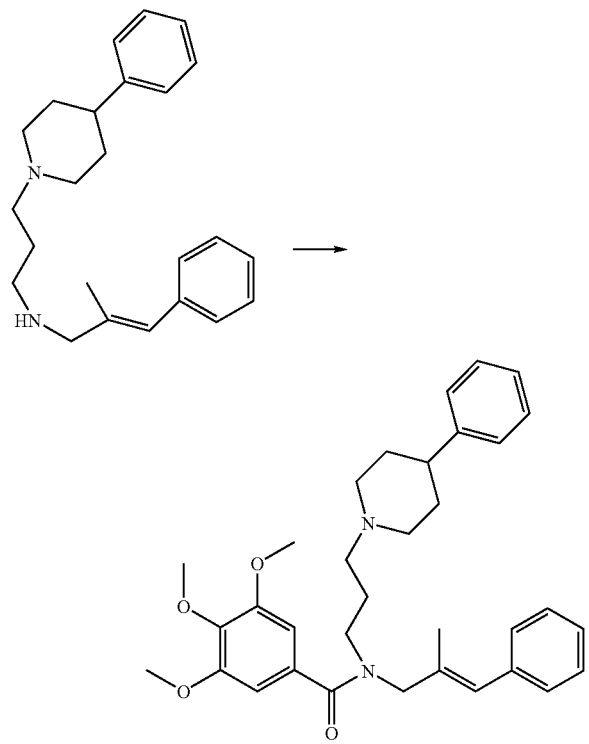

Experimental condition analogous to Example 18 were used with (2-methyl-3-phenyl-allyl-[3-(4-phenyl-piperidin-1-yl)-propyl-amine 0.47 g (1.5 mmol), 3,4,5-trimethoxy benzoic acid 0.31 g (1.48 mmol), thionyl chloride 0.32 g (2.7 mmol) and triethylamine. The reaction yielded the free amine, which was converted to HCl salt, to give 106 mg of an off-white solid. Yield: 12%.

LC-MSD, m/z for $C_{34}H_{42}N_2O_4$ [M+H]+: 542.31 $^1$H NMR (300 MHz, MeOD): δ 1.6-1.7 (s, 3H), 1.9-2.2 (m, 7H), 2.9-3.0 (m, 1H), 3.0-3.2 (m, 6H), 3.6-3.8 (m, 10H), 4.1-4.3 (s, 2H), 6.5 (s, 1H), 6.9 (s, 2H), 7.1-7.5 (m, 10H).

Example 89

3,4-5-Trimethoxy-N-(2-methyl-3-phenyl-allyl)-N-(3-piperidin-1-yl-propyl)-benzamide

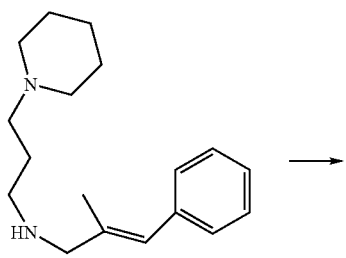

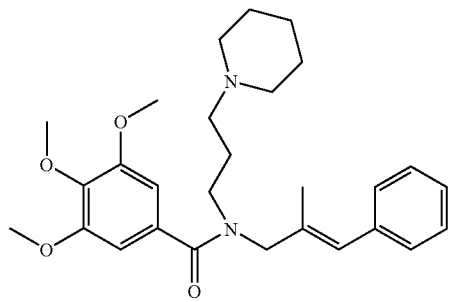

Experimental condition analogous to Example 18 were used with (2-methyl-3-phenyl-allyl-(3-piperidin-1-yl-propyl)-amine 0.65 g (2.3 mmol), 3,4,5-trimethoxy benzoic acid 0.6 g (2.87 mmol), thionyl chloride 0.5 g (4.7 mmol) and triethylamine 0.93 ml. The reaction yielded the free amine, which was converted to HCl salt to give 110 mg of a pale, yellow hydroscopic solid. Yield: 12%.

$^1$H NMR (300 MHz, MeOD): δ 1.4-1.5 (m, 2H), 1.7-2.0 (m, 5H), 2.1-2.3 (m, 2H), 2.9-3.0 (m, 2H), 3.1-3.3 (m, 2H), 3.5-3.7 (m, 5H), 3.7-3.9 (m, 10H), 4.0-4.1 (s, 2H), 6.5 (s, 1H), 6.8 (s, 2H), 7.1-7.4 (m, 5H).

Example 90

3,4-5-Trimethoxy-N-(2-methyl-3-phenyl-allyl)-N-(3-morpholin-4-yl-propyl)-benzamide

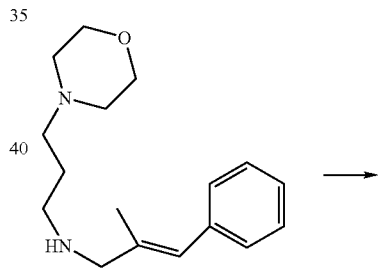

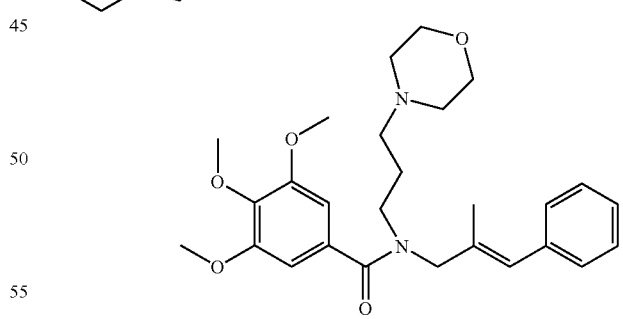

Experimental condition analogous to Example 18 were used with (2-methyl-3-phenyl-allyl-(3-morpholino-4-yl-propyl)-amine 0.72 g (2.6 mmol), 3,4,5-trimethoxy benzoic acid 0.6 g (2.87 mmol), thionyl chloride 0.6 g (5.2 mmol) and triethylamine 0.93 ml. The reaction yielded the free amine, which was converted to HCl salt to give 80 mg of a pale, brown hydroscopic solid. Yield: 6.5%.

LC-MSD, m/z for $C_{27}H_{36}N_2O_5$ [M+H]+: 469 $^1$H NMR (300 MHz, MeOD): δ 1.7 (s, 3H), 2.1-2.4 (m, 2H), 3.4-3.5 (m, 2H), 3.5-3.6 (m, 2H), 3.7-4.0 (m, 14H), 4.0-4.1 (m, 2H), 6.5 (s, 1H), 6.8 (s, 2H), 7.2-7.5 (m, 5H).

Example 91

N-(1-Butyl-piperidin-4-ylmethyl)-3,4,5-trimethoxy-N-(2-methyl-3-phenyl-allyl)-benzamide Butyl bromide 0.15 g (1.1 mmol) was added to a mixture of 3,4,5-trimethoxy-N-(2-methyl-3-phenyl-allyl)-N-piperidin-4-ylmethyl-benzamide (prepared according to the scheme 22) 0.25 g (0.5 mmol) and potassium carbonate 0.19 g (1.4 mmol) in 5 ml dimethylformamide at 0° C. The reaction was warmed to room temperature and stirred for 3 hours. The Scheme 22: N-(1-Butyl-piperidin-4-ylmethyl)-3,4,5-trimethoxy-N-(2-methyl-3-phenyl-allyl)-benzamide

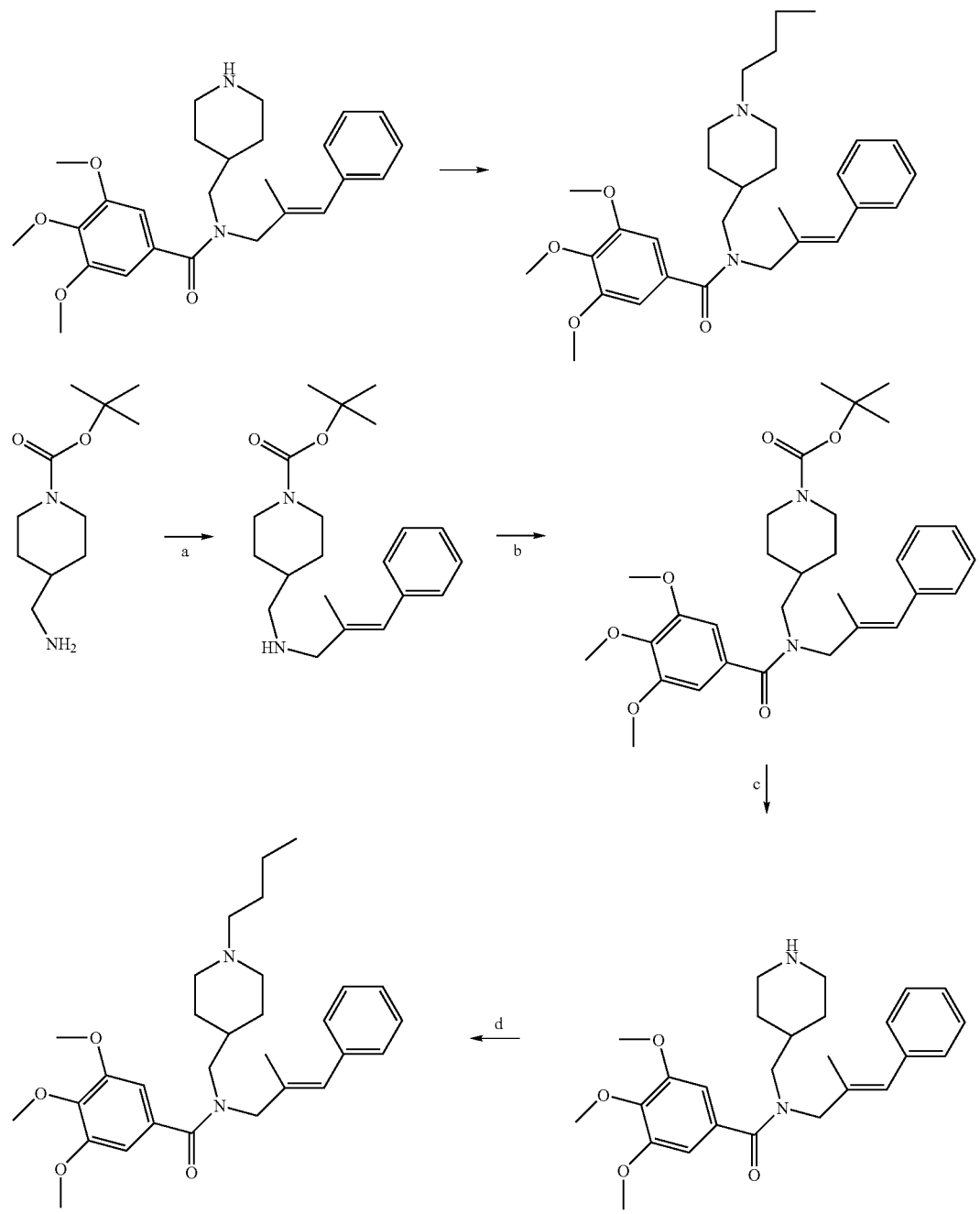

a: 1/α-methylcinamaldehyde, dichloromethane
   2/ Sodium borohydride, methanol
b: 3,4,5-trimethoxy benzoic acid, TBTU
c: HCl/dioxane
d: Butyl bromide, potassium carbonate, dimethylformamide reaction mixture was concentrated and purified by flash chromatography chloroform methanol 9:1, to yield free amine. This amine was converted to the HCl salt to give 72 mg of off-white solid. Yield: 13%.

LC-MSD, m/z for $C_{30}H_{42}N_2O_4$ [M+H]+: 495.4

Example 92

3,4-5-Trimethoxy-N-(2-methyl-3-phenyl-allyl)-N-(2-thiomorpholin-4-yl-ethyl)-benzamide

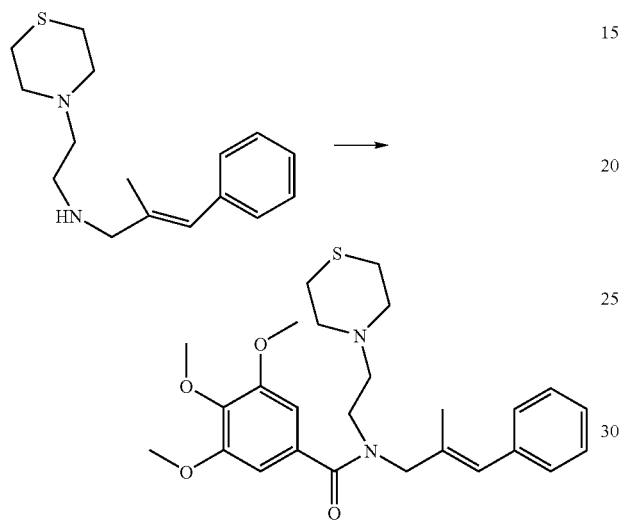

Experimental condition analogous to Example 13 were used with (2-methyl-3-phenyl-allyl-(2-thiomorpholin-4-yl-ethyl)-amine 0.5 g (1.8 mmol), 3,4,5-trimethoxy benzoic acid 0.42 g (1.7 mmol), O-(benzotriazole-1-yl)-N,N,N',N'-tetramethyluronium tetrafluoroborate 1.16 g (3.6 mmol) and triethylamine 0.2 ml. The reaction yielded the free amine, which was converted to the HCl salt, yielding 157 mg of a pink solid. Yield: 19%.

LC-MSD, m/z for $C_{26}H_{34}N_2O_5S$ [M+H]+: 471.2 $^1$H NMR (300 MHz, MeOD): δ 1.7 (m, 3H), 2.7-3.0 (m, 2H), 3.1-3.4 (m, 3H), 3.5-3.6 (m, 3H), 2.7-3.1 (m, 2H), 3.7-3.8 (m, 10H), 3.9-4.0 (m, 4H), 4.0-4.4 (m, 2H), 6.5 (s, 1H), 6.8-6.9 (m, 2H), 7.2-7.4 (m, 5H).

Example 93

N-[3-(2,4-Difluoro-phenyl)-2-methyl-allyl]-3,4,5-trimethoxy-N-piperidin-3-yl-benzamide

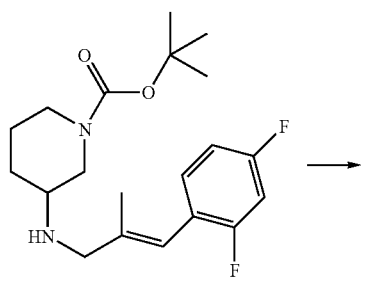

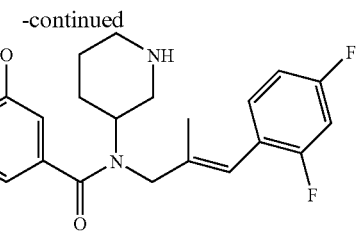

Experimental condition analogous to Example 18 were used with 3-[3-(2,4-difluoro-phenyl)-2-methyl-allylamino]-piperidine-1-carboxylic acid tert-butyl ester 0.35 g (0.94 mmol), 3,4,5-trimethoxy benzoic acid 0.24 g (1.13 mmol), thionyl chloride 0.15 g (0.94 mmol) and triethylamine 0.1 ml. The reaction yielded 380 mg BOC protected intermediate. This intermediate 0.36 g (0.64 mmol) was dissolved in 5 ml dioxane, 6 N HCl was added, and the mixture was stirred at room temperature for 14 hr. A basic work up led to 319 mg of free amine. This was converted to the HCl salt, yielding 100 mg of a yellow solid. Yield: 33%.

LC-MSD, m/z for $C_{25}H_{30}N_2O_4F_2$ [M+H]+: 461.4 $^1$H NMR (300 MHz, MeOD): δ 1.0-1.3 (m, 2H), 1.6-2.0 (m, 5H), 2.0-2.2 (m, 2H), 2.4-2.6 (m, 1H), 2.7-3.1 (m, 2H), 3.7-4.0 (m, 10H), 4.0-4.4 (m, 2H), 6.5 (s, 1H), 6.7 (s, 2H), 6.8-7.0 (m, 2H), 7.3-7.5 (m, 1H).

Example 94

N-(1-Cyclohexylmethyl-piperidin-3-yl)-N-[3-(2,4-difluoro-phenyl)-2-methyl-allyl]-3,4,5-trimethoxy-benzamide

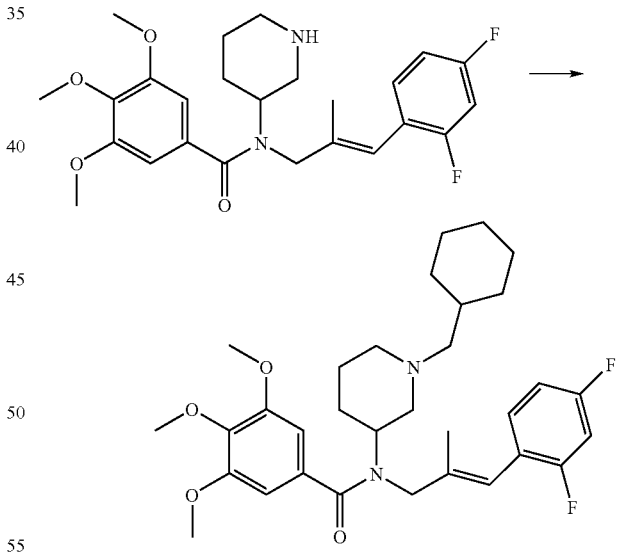

Experimental condition analogous to Example 14 were used with N-[3-(2,4-difluoro-phenyl)-2-methyl-allyl]-3,4,5-trimethoxy-N-piperidin-3-yl-benzamide 0.15 g (0.22 mmol), cyclohexyl carboxaldehyde 0.029 g (0.26 mmol), acetic acid 0.021 ml (0.35 mmol) and sodium cyanoborohydride 0.02 g (0.35 mmol). Transformation of the free base to HCl salt yielded 180 mg of white solid. Yield: 99%.

LC-MSD, m/z for $C_{32}H_{42}N_2O_4F_2$ [M+H]+: 557.4 $^1$H NMR (300 MHz, MeOD/$D_2$O): δ 1.0-1.4 (m, 5H), 1.5-1.9 (m, 10H), 2.0-2.3 (m, 3H), 2.9-3.0 (m, 3H), 3.4-3.6 (m, 2H), 3.7-4.0 (m, 10H), 4.0-4.2 (m, 2H), 4.9-4.6 (m, 1H), 6.5 (s, 1H), 6.7 (s, 2H), 6.8-7.0 (m, 2H), 7.2-7.5 (m, 1H).

Example 95

3,4,5-Trimethoxy-N-(2-methyl-3-phenyl-allyl)-N-pyrrolidin-3-ylmethyl-benzamide

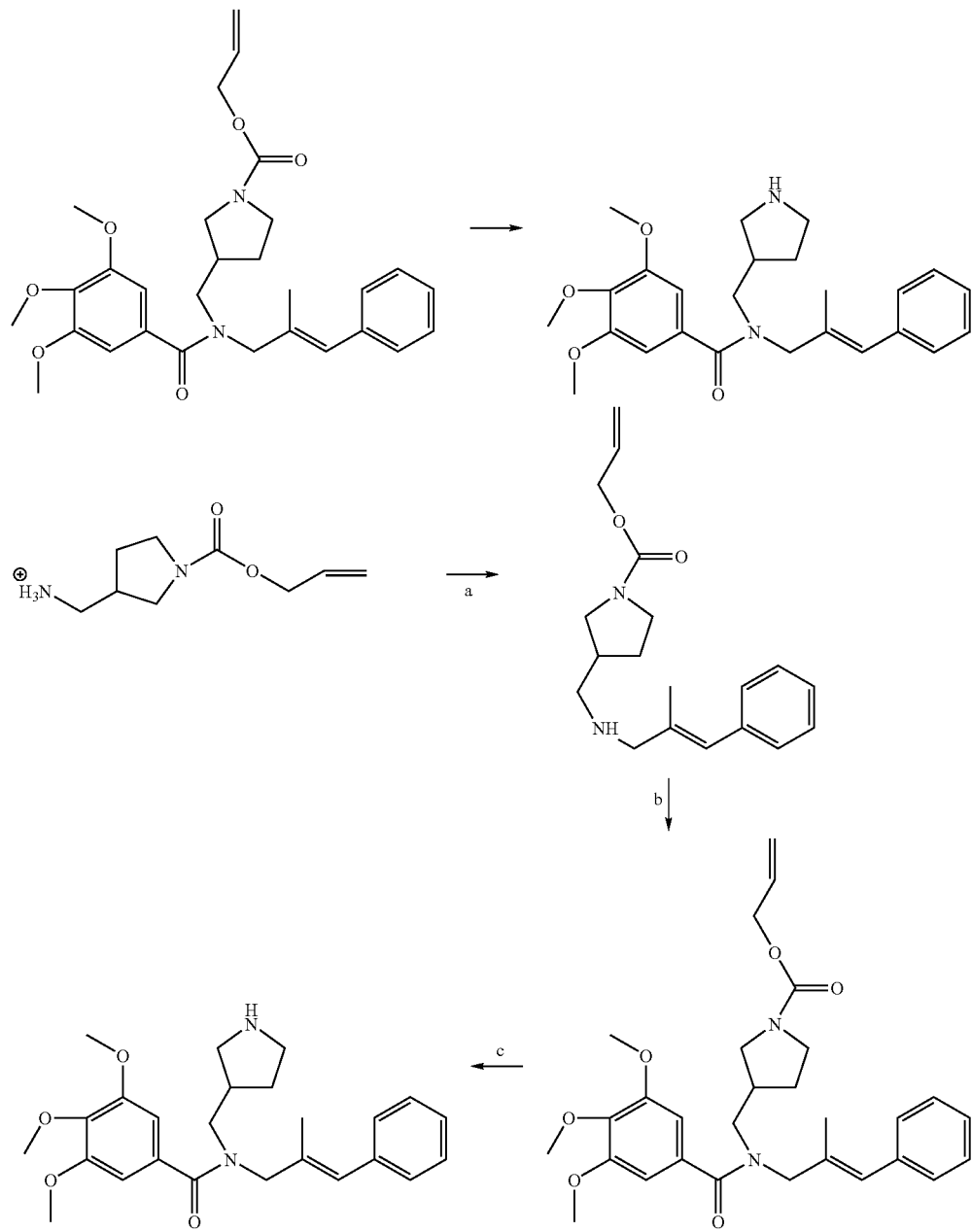

Scheme 23: Preparation of 3,4,5-trimethoxy-N-(2-methyl-3-phenyl-allyl)-N-pyrrolidin-3-ylmethyl-benzamide a: 1/ α-Methyl cinnamaldehyde, Et₃N, dichloromethane
2/ Sodium borohydride, methanol
b: 3,4,5-trimethoxy benzoic acid, Et₃N, EDC, HOBT
c: Dimethylmalonate, sodium hydride, (Ph₃)₄Pd A mixture of the 3-{[(2-methyl-3-phenyl-allyl)-(3,4,5-trimethoxy-benzoyl)-amino]-methyl}-pyrrolidine-1-carboxylic acid allyl ester (prepared according to the scheme 23) 0.12 g (0.24 mmol), dimethylmalonate 0.09 g (0.73 mmol), sodium hydride 5 mg, and tetrakis triphenylphosphine palladium 5 mg was stirred in 3 ml anhydrous THF at room temperature for one hour under nitrogen.

The reaction mixture was concentrated and was subjected to flash chromatography on silica gel, chloroform 9-methanol 1 as eluent, to yield the free amine. This free amine was converted to its HCl salt gave 34 mg pale yellow solid. Yield: 30%.

LC-MSD, m/z for $C_{25}H_{32}N_2O_4$ [M+H]+: 425.4 ¹H NMR (300 MHz, MeOD): δ 1.7-2.0 (m, 2H), 2.5-2.7 (m, 1H), 2.8-3.0 (m, 1H), 3.1-3.3 (m, 1H), 3.2-3.4 (m, 3H), 3.5-3.7 (m, 3H), 3.7-4.0 (m, 11H), 4.0-4.4 (s, 2H), 6.5 (s, 1H), 6.7 (s, 2H), 7.1-7.5 (m, 5H).

Example 96

7-Methoxy-2,2-dimethyl-benzo[1,3]dioxole-5-carboxylic acid [4-hydroxy-1-(tetrahydro-pyran-4-yl)-pyrrolidin-2-ylmethyl]-(2-methyl-3-phenyl-allyl)-amide

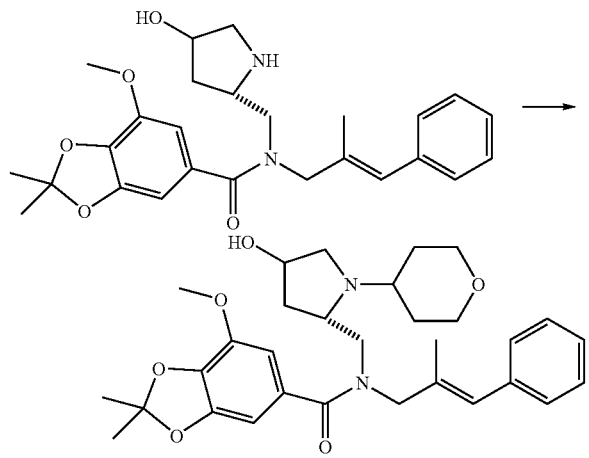

Experimental condition analogous to Example 14 were used with 7-methoxy-2,2-dimethyl-benzo[1,3]dioxole-5-carboxylic acid (4-hydroxy-pyrrolidin-2-ylmethyl)-(2-methyl-3-phenyl-allyl)-amide 0.16 g (0.35 mmol), tetrahydro-4H-pyrane-4-one 0.042 g (0.42 mmol), acetic acid 0.03 ml (0.53 mmol) and sodium cyanoborohydride 0.026 g (0. 42 mmol). After transforming the free base to HCl salt, 130 mg of white solid was obtained. Yield: 65%.

LC-MSD, m/z for $C_{31}H_{40}N_2O_6$ [M+H]+: 537.2, [M+2H]+: 538.2 $^1$H NMR (300 MHz, MeOD): δ 1.5-2.0 (m, 12H), 2.0-2.4 (m, 4H), 2.4-2.5 (m, 1H), 3.2-3.5 (m, 3H), 3.5-3.9 (m, 4H), 3.9-4.1 (m, 4H), 4.2 (s, 2H), 4.4-4.5 (s, 1H), 4.6 (s, 1H) 6.5 (s, 1H), 6.7 (s, 1H), 6.9 (s, 1H), 7.2-7.5 (m, 5H).

Example 97

N-(1-Cyclohex-3-enylmethyl-pyrrolidin-2-ylmethyl)-3,4,5-trimethoxy-N-(2-methyl-3-phenyl-allyl)-benzamide

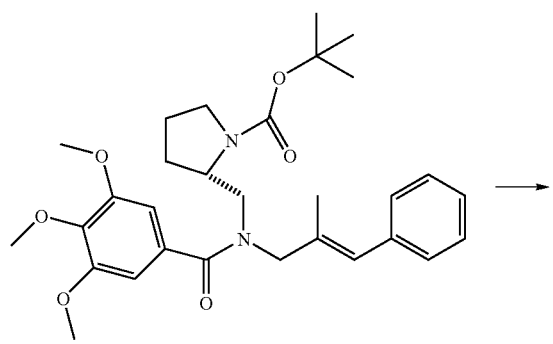

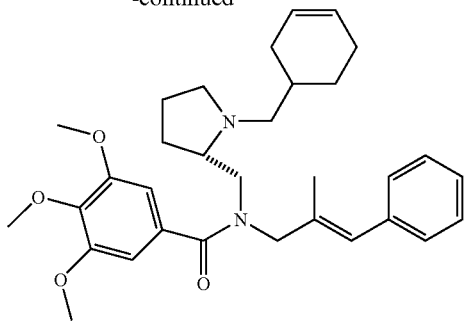

To a solution mixture of dichloromethane 70 ml and 30 ml trifluoroacetic acid, at room temperature was added 2-{[(2-methyl-3-phenyl-allyl)-(3,4,5-trimethoxy-benzoyl)-amino]-methyl}-pyrrolidine-1-carboxylic acid tert-butyl ester 1.2 g (2.45 mmol) was added, and the mixture was stirred 1 hr. To this mixture was added saturated solution of sodium bicarbonate until basic PH, and extracted 3 times with dichloromethane. Organic layer was then dried over magnesium sulfate filtrated, and concentrated under vacuum. The intermediate free amine was dissolved in 20 ml dichloromethane with a spatula of molecular sieve. To this mixture was added 1,2,3,6 tetrahydro-benzaldehyde 0.29 g (2.7 mmol), and sodium triacethoxyborohydride 0.77 g (3.67 mmol). The molecular sieve was filtrated and saturated solution of sodium bicarbonate was added, the aqueous layer was extracted with dichloromethane 3 times. The combined organic layer was dried over magnesium sulfate, filtrated and concentrated under vacuum, we obtain of free amine, which was converted to the HCl salt. Lead to 500 mg of slightly pink powder. Yield: 36%.

Analytical $C^{18}$ HPLC using 20-80% acetonitrile gradient in 20 minute, elute at 18.11 minutes.

LC-MSD, m/z for $C_{32}H_{42}N_2O_4$ [M+H]+: 519.2, [M+2H]: 520.2, [M+3H]: 521.2

Example 98

N-[3-(2,4-Difluoro-phenyl)-2-methyl-allyl]-3,4-dimethoxy-N-pyrrolidin-3-yl-benzamide

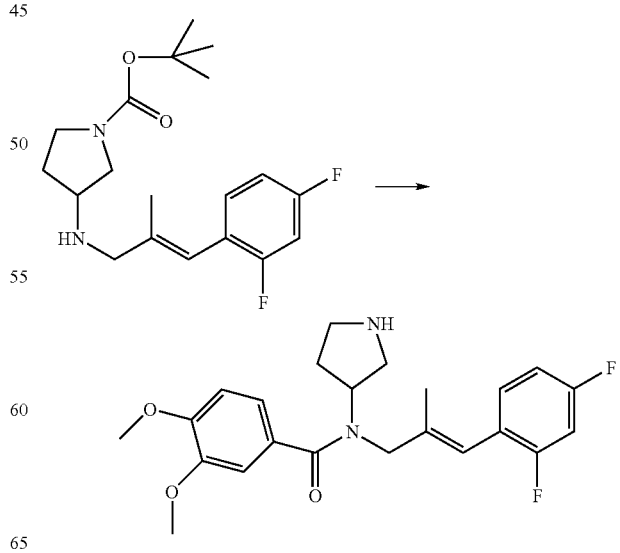

Experimental condition analogous to Example 18 were used with 3,4-dimethoxybenzoic acid 0.12 g (0.68 mmol), thionyl chloride 2 ml (1.68 mmol). The obtained acyl chloride was reacted with 3-[3-(2,4-difluoro-phenyl)-2-methyl-allylamino]-pyrrolidine-1-carboxylic acid tert-butyl ester 0.2 g (0.56 mmol), triethylamine 0.2 ml. The reaction yielded the free amine, which was converted to the HCl salt 90 mg as an off-white solid: Yield: 35%.

LC-MSD, m/z for $C_{23}H_{26}N_2O_3F_2$ [M+H]+:417.6 $^1$H NMR (300 MHz, MeOD): δ 1.7 (s, 3H), 2.4-2.6 (m, 2H), 3.2-3.6 (m, 3H), 3.6-4.0 (m, 8H), 4.1 (s, 2H), 4.4-4.5 (s, 1H), 6.5 (s, 1H), 6.9-7.5 (m, 6H)

Example 99

N-[2-Bromo-3-(4-fluoro-phenyl)-allyl]-N-(1-cyclohexylmethyl-pyrrolidin-2-ylmethyl)-3,4,5-trimethoxybenzamide

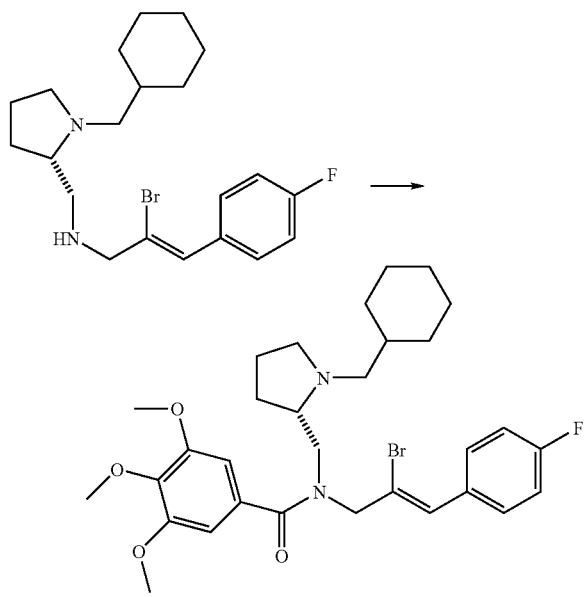

Experimental condition analogous to Example 12 were used with [2-bromo-3-(4-fluoro-phenyl)-allyl]-(1-cyclohexylmethyl-pyrrolidin-2-ylmethyl)-amine 0.15 g (0.36 mmol), 3,4,5-trimethoxy-benzoylchloride 0.1 g (0.47 mmol), and triethylamine 0.08 ml. Reverse phase high pressure liquid chromatography with a gradient of 20-80% acetonitrile phase lead to 120 mg of white powder as a TFA salt.

LC-MSD, m/z for $C_{31}H_{40}N_2O_4$ FBr [M+2H]+:605.1 $^1$H NMR (400 MHz, CDCl$_3$): δ 1.0-2.2 (m, 14H), 2.4-2.6 (m, 2H), 2.8-3.1 (m, 2H), 3.4-3.6 (m, 2H), 3.6-4.0 (3 s, 9H), 4.3-4.5 (m, 6.5 (s, 2H), 6.9-7.1 (m, 2H), 7.2 (s, 1H), 7.4-7.6 (m, 2H)

Example 100

3,4,5-Trimethoxy-N-(2-methyl-3-phenyl-allyl)-N-(2-piperidin-1-yl-ethyl)-benzamide

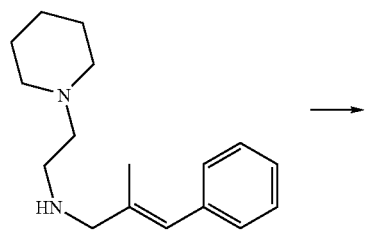

(2-Methyl-3-phenyl-allyl)-(2-piperidin-1-yl-ethyl)-amine, 0.5 g (1.9 mmol), was dissolved in 10 ml of anhydrous methanol under nitrogen. The solution was cooled to 0° C. To this mixture was added 3,4,5-trimethoxybenzoic acid 0.49 g (2.3 mmol), 0.2 ml of triethylamine, and TBTU 1.2 g (3.8 mmol). The reaction was stirred for 18 hours at room temperature. The reaction mixture was then diluted with chloroform, extracted with 2×10 ml of water, 2×10 ml sodium bicarbonate, and washed 2×10 ml of brine. The organic layer was dried over sodium sulfate and was concentrated. The compound was then purified on silica gel using 1.2% methanol in chloroform to give 102 mg of product as an off white HCl salt. Yield: 12%.

LC-MSD, m/z for $C_{27}H_{36}N_2O_4$ [M+H]+: 453.3.

Testing

To demonstrate that the compounds described above are useful modulators for SDF-1 and I-TAC chemokines, the compounds were screened in vitro to determine their ability to displace SDF-1 and/or I-TAC from the CCXCKR2 receptor at multiple concentrations. The compounds were combined with mammary gland cells expressing the CCXCKR2 receptor in the presence of the $^{125}$I-labeled chemokine as detailed in Determination of IC$_{50}$ values, Reagents and Cells (see below). The ability of the compounds to displace the labeled chemokine from the CCXCKR2 receptor cites at multiple concentrations was then determined with the screening process.

TABLE 1

Compounds that were deemed effective modulators were able to displace at least 50% of either of the chemokines SDF-1 or I-TAC from the CCXCKR2 receptor at concentrations at or below 1.1 micromolar (μM) and more preferably at concentrations at or below 300 nanomolar (nM). At present, especially preferred compounds can displace at least 50% of the SDF-1 or I-TAC from the CCXCKR2 receptor at concentrations at or below 200 nM. Exemplary compounds that met these criteria are reproduced in Table 2 below.

TABLE 2

| No. | Compound |
| --- | --- |
| 1 | |

TABLE 2-continued

| No. | Compound |
|---|---|
| 2 | (structure) |
| 3 | (structure) |
| 4 | (structure) |
| 5 | (structure) |
| 6 | (structure) |
| 7 | (structure) |
| 8 | (structure) |
| 9 | (structure) |
| 10 | (structure) |
| 11 | (structure) |

TABLE 2-continued
| No. | Compound |
|---|---|
| 12 | 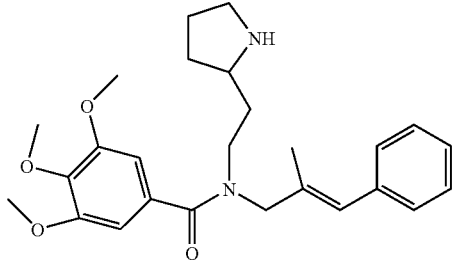 |
| 13 | 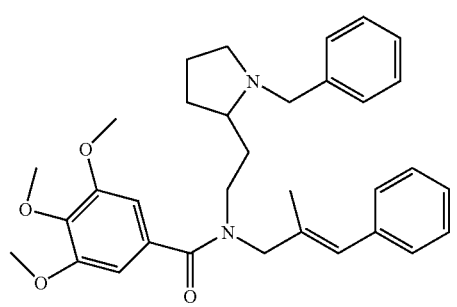 |
| 14 | 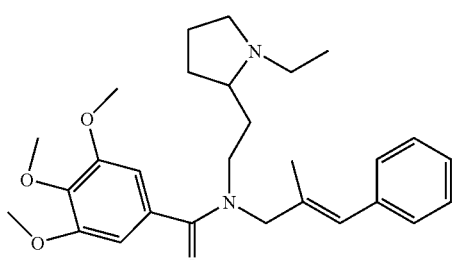 |
| 15 | 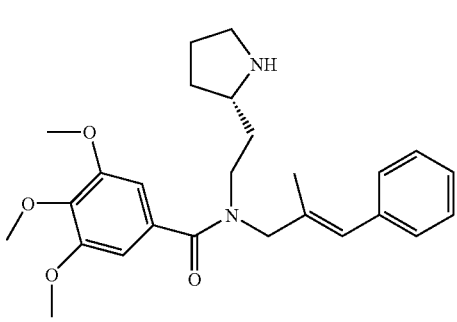 |
| 16 | 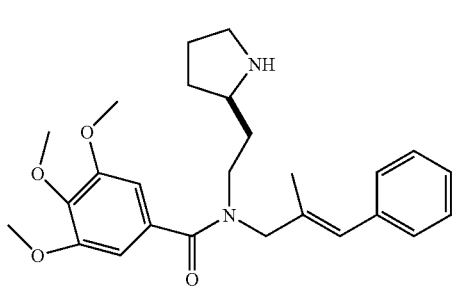 |
| 17 | 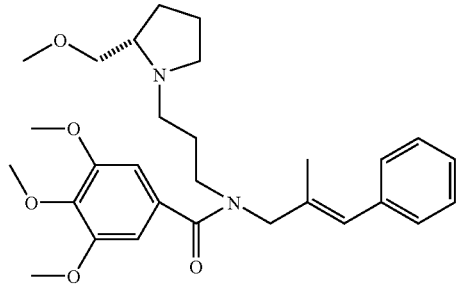 |
| 18 | 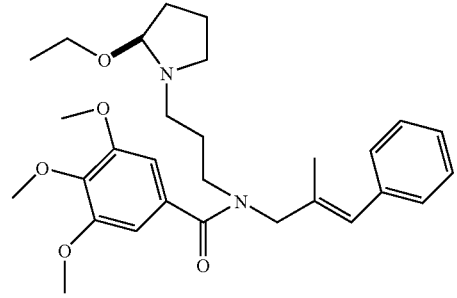 |
| 19 | 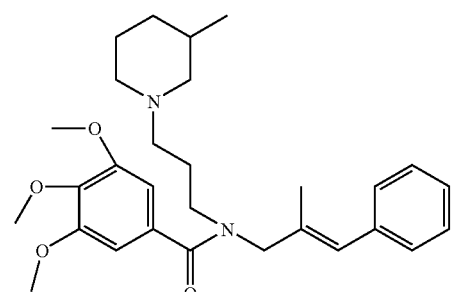 |
| 20 | 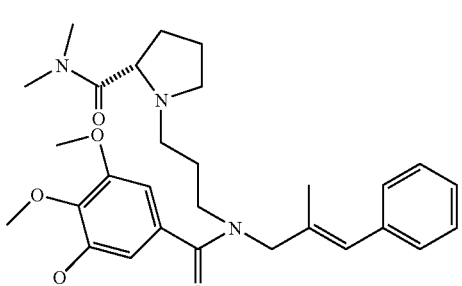 |
| 21 | 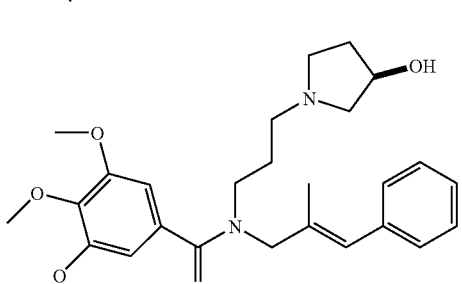 |

TABLE 2-continued

| No. | Compound |
|---|---|
| 22 | (structure) |
| 23 | (structure) |
| 23 | (structure) |
| 24 | (structure) |
| 25 | (structure) |
| 26 | (structure) |
| 27 | (structure) |
| 28 | (structure) |
| 29 | (structure) |
| 30 | (structure) |

TABLE 2-continued

| No. | Compound |
|---|---|
| 31 | |
| 32 | |
| 33 | |
| 34 | |
| 35 | |
| 36 | |
| 37 | |
| 38 | |
| 39 | |
| 40 | |

TABLE 2-continued

| No. | Compound |
|---|---|
| 41 | |
| 42 | |
| 43 | |
| 44 | |
| 45 | |
| 46 | |
| 47 | |
| 48 | |
| 49 | |

TABLE 2-continued
| No. | Compound |
|---|---|
| 50 | 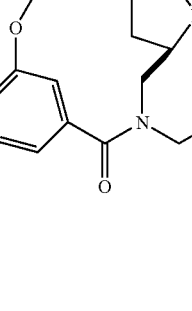 |
| 51 | |
| 52 | |
| 53 | |
| 54 | |
TABLE 2-continued
| No. | Compound |
|---|---|
| 55 | 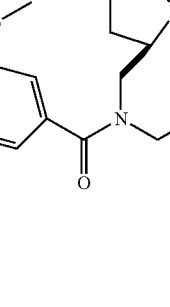 |
| 56 | |
| 57 | |
| 58 | |
| 59 | |
| 60 | |

TABLE 2-continued

| No. | Compound |
|---|---|
| 61 | (structure) |
| 62 | (structure) |
| 63 | (structure) |
| 64 | (structure) |
| 65 | (structure) |
| 66 | (structure) |
| 67 | (structure) |
| 68 | (structure) |
| 69 | (structure) |
| 70 | (structure) |
| 71 | (structure) |
| 72 | (structure) |

TABLE 2-continued
| No. | Compound |
|---|---|
| 73 | 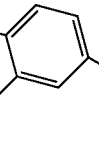 |
| 74 | 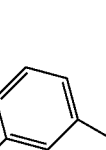 |
| 75 |  |
| 76 | 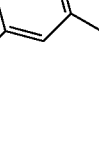 |
| 77 | 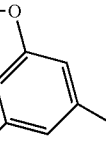 |
| 78 |  |
| 79 | 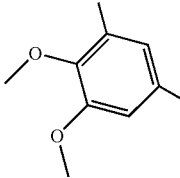 |
| 80 | 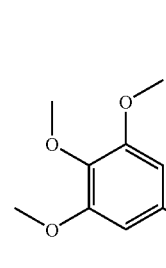 |
| 81 | 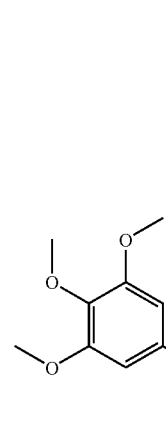 |
| 82 | 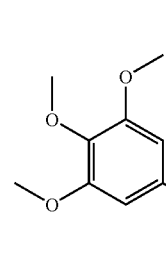 |
| 83 | 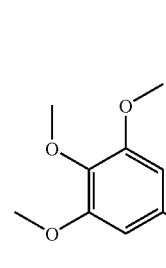 |

TABLE 2-continued

| No. | Compound |
|-----|----------|
| 84 | (structure) |
| 85 | (structure) |
| 86 | (structure) |
| 87 | (structure) |
| 88 | (structure) |
| 89 | (structure) |
| 90 | (structure) |
| 91 | (structure) |
| 92 | (structure) |
| 93 | (structure) |

TABLE 2-continued
| No. | Compound |
|---|---|
| 94 | 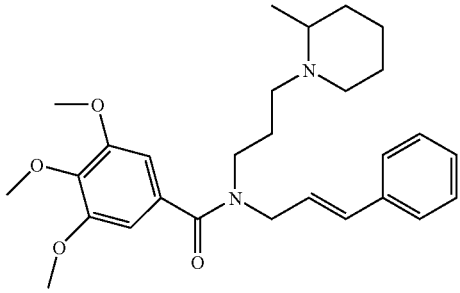 |
| 95 | 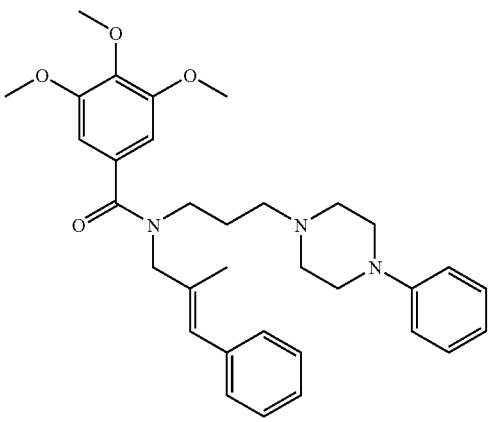 |
| 96 | 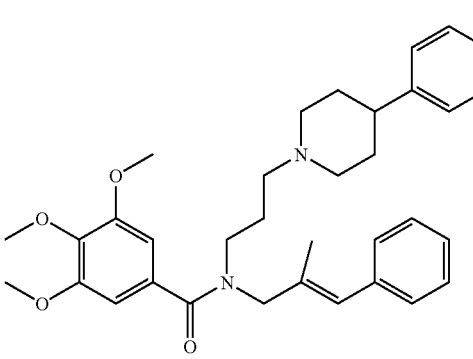 |
| 97 | 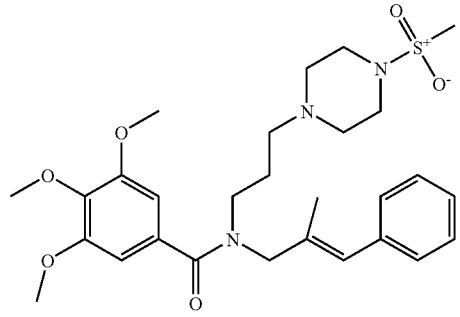 |
| 98 | 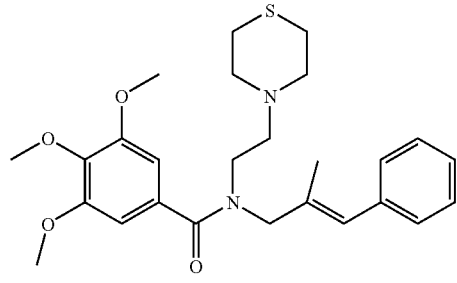 |
| 99 | 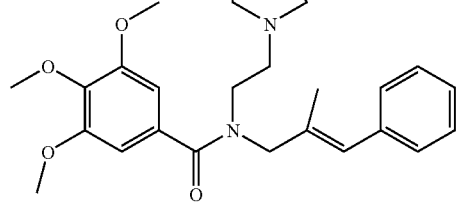 |
| 100 | 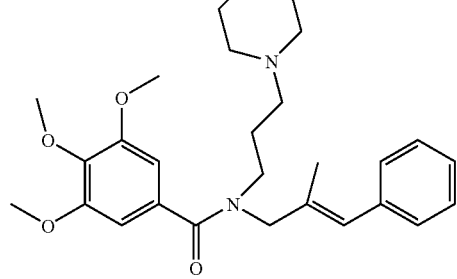 |
| 101 | 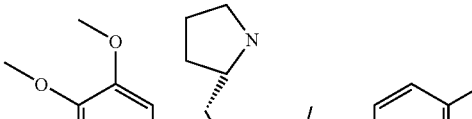 |
| 102 |  |

TABLE 2-continued

| No. | Compound |
|---|---|
| 103 | (structure) |
| 104 | (structure) |
| 105 | (structure) |
| 106 | (structure) |

Determination of $IC_{50}$ Values

Reagents and Cells. $^{125}$I-labeled SDF-1 was purchased from Perkin-Elmer Life Sciences, Inc. (Boston, Mass.). A MCF-7 (adenocarcinoma; mammary gland) cell line was obtained from the American Type Culture Collection (Manassas, Va.) and was cultured in DMEM (Mediatech, Herndon, Va.) supplemented with 10% fetal bovine serum (FBS) (Hy-Clone Logan, Utah) and bovine insulin (0.01 mg/mL) (Sigma, St. Louis, Mo.) at 37° C. in a humidified incubator at a 5% $CO_2$/air mixture.

Binding Analysis. Target compounds were tested to determine their ability to bind with CCXCKR2 sites on MCF-7 cells. Efficiency-maximized radioligand binding using filtration protocols as described in Dairaghi D J, et al., *HHV8-encoded vMIP-I selectively engages chemokine receptor CCR5. Agonist and antagonist profiles of viral chemokines.*, J. Biol. Chem. Jul. 30, 1999; 274(31): 21569-74 and Gosling J, et al., *Cutting edge: identification of a novel chemokine receptor that binds dendritic cell-and T cell-active chemokines including ELC, SLC, and TECK.*, J. Immunol. 2000 Mar 15; 164(6): 2851-6 was used.

In these assays, MCF-7 cells were interrogated with the target compounds and the ability of these compounds to displace $^{125}$I radiolabeled SDF-1 was assessed using the protocol described in Dairaghi and Gosling. The target compounds were added to the plate to the indicated concentration and were then incubated with cells followed by the addition of radiolabeled chemokine ($^{125}$I SDF-1) for 3 hr at 4° C. in the following binding medium (25 mM HEPES, 140 mM NaCl, 1 mM $CaCl_2$, 5 mM $MgCl_2$ and 0.2% bovine serum albumin, adjusted to pH 7.1). All assays were then incubated for 3 hrs at 4° C. with gentle agitation. Following incubation in all binding assays, reactions were aspirated onto PEI-treated GF/B glass filters (Packard) using a cell harvester (Packard) and washed twice (25 mM HEPES, 500 mM NaCl, 1 mM $CaCl_2$, 5 mM $MgCl_2$, adjusted to pH 7.1). Scintillant (MicroScint 10, Packard) was added to the wells, and the filters were counted in a Packard Topcount scintillation counter. Data were analyzed and plotted using Prism (GraphPad Prism version 3.0a for Macintosh, GraphPad Software, www.graphpad.com).

Inhibition of Cell Proliferation in vitro.

Antagonism of CCXCKR2 expressed on a mammary carcinoma by small molecular weight compounds inhibited cell proliferation in vitro. Cells treated in vitro exhibited reduced cell growth over time as compared to untreated controls.

Inhibition of Cell Adhesion in vitro.

In vitro static adhesion assays are used to model the events of leukocyte migration, including the adhesion of cells and subsequent emigration into a given tissue. Monolayers of vascular endothelial cells were grown on a surface, and cells expressing CCXCKR2 were labeled with a fluorescent dye to enable visualization. Experiments showed that the presence of CCXCKR2 expressing cells adhered to an endothelial layer encouraged adhesion of additional CCXCKR2 expressing cells as compared to control groups in which CCXCKR2 was not expressed. Additionally, the addition of a CCXCKR2 modulator inhibited adhesion as compared to a vehicle-treated control group.

Inhibition of Tumor Formation in vivo.

Immunodeficient mice were injected with human B cell lymphoma cells expressing CCXCKR2. Treatment of those mice with CCXCKR2 modulators inhibited the ability of vascularized tumors to form. In one study, only one of 17 mice treated with a CCXCKR2 antagonist developed an encapsulated, vascularized tumor, while 11 of 17 mice in a vehicle control group developed encapsulated, vascularized tumor.

Reduction of Tumor Volume in vivo.

Immunodeficient mice were injected with a human mammary carcinoma. Tumor measurements were made three times a week and tumor volume was determined. Mice treated with a CCXCKR2 modulator exhibited reduced tumor volumes as compared to mice in the vehicle control group.

Any person of ordinary skill in the art of organic chemistry will recognize from the provided description, figures, and examples, that modifications and changes can be made to the preferred embodiments of the invention without departing from the scope of the invention defined by the following claims and their equivalents.

What is claimed is:

1. A compound of the structure (I), or a salt thereof:

(I)

where m is an integer from 1 to 5;
each Y is independently selected from the group consisting of hydrogen, halogen, —CN, —NO$_2$, —OH, —OR', —C(O)R', —CO$_2$R', —O(CO)R', —C(O)NR'R", —OC(O)NR'R", —SR', —SOR', —SO$_2$R', —SO$_2$NR'R", —NR'R", —NR'C(O)R", —NR'C(O)$_2$R", —NR'SO$_2$R", —NR'(CO)NR"R"', unsubstituted or substituted C$_{1-8}$ alkyl, unsubstituted or substituted C$_{2-8}$ alkenyl, unsubstituted or substituted C$_{2-8}$ alkynyl, unsubstituted or substituted C$_{3-8}$ cycloalkyl, and unsubstituted or substituted C$_{6-10}$ aryl;
where each R', R" and R"' are each independently from the group consisting of:
hydrogen, halogen, unsubstituted or substituted C$_{1-8}$ alkyl, and unsubstituted or substituted C$_{6-10}$ aryl;
n is 0, 1, 2 or 3;
Z is a substituted or unsubstituted group of the formulae:

where R$^7$ is selected from the group consisting of hydrogen, —C(O)R', —CO$_2$R', —C(O)NR'R", —SO$_2$R', unsubstituted or substituted C$_{1-10}$ alkyl, unsubstituted or substituted C$_{1-8}$ alkoxyl, unsubstituted or substituted C$_{2-10}$ alkenyl, unsubstituted or substituted C$_{2-10}$ alkynyl, unsubstituted or substituted C$_{3-10}$ cycloalkyl, unsubstituted or substituted C$_{6-10}$ aryl, and C$_{6-10}$ aryloxy, where each R', R" and R"' are each independently from the group consisting of: hydrogen, halogen, unsubstituted or substituted C$_{1-8}$ alkyl, and unsubstituted or substituted C$_{6-10}$ aryl;
R$^6$ is alkyl, hydrogen, or halogen; and
R$^3$, R$^4$, and R$^5$ are each independently selected from the group consisting of hydrogen, halogen, —CN, —NO$_2$, —OH, —OR', —C(O)R', —CO$_2$R', —O(CO)R', —C(O)NR'R", —OC(O)NR'R", —SR', —SOR', —SO$_2$R', —SO$_2$NR'R", —NR'R", —NR'C(O)R", —NR'C(O)$_2$R", —NR'SO$_2$R", —NR'(CO)NR"R"', unsubstituted or substituted C$_{1-8}$ alkyl, unsubstituted or substituted C$_{2-8}$ alkenyl, unsubstituted or substituted C$_{2-8}$ alkynyl, unsubstituted or substituted C$_{3-8}$ cycloalkyl, and unsubstituted or substituted C$_{6-10}$ aryl.

2. The compound of claim 1, where R$^6$ is hydrogen.
3. The compound of claim 1, where R$^6$ is substituted or unsubstituted C$_{1-8}$ alkyl.
4. The compound of claim 1, where R$^6$ is halogen.
5. The compound of claim 1, where R$^3$, R$^4$, and R$^5$ are each independently selected from the group consisting of hydrogen, —OR', and substituted or unsubstituted C$_{1-8}$ alkyl.

6. The compound of claim 1, where R$^3$, R$^4$, and R$^5$ are each independently selected from the group consisting of —OR' and hydrogen.
7. The compound of claim 1, where R$^3$, R$^4$, and R$^5$ are each —OR', where R' is substituted C$_{1-8}$ alkyl.
8. The compound of claim 1, where Z is a substituted or unsubstituted group of the formula:

9. The compound of claim 1, where Z is a substituted or unsubstituted group of the formula:

10. The compound of claim 1, where Z is a substituted or unsubstituted group of the formula:

where R$^7$ is selected from the group consisting of hydrogen, —C(O)R', —CO$_2$R', —C(O)NR'R", —SO$_2$R, unsubstituted or substituted C$_{1-10}$ alkyl, unsubstituted or substituted C$_{1-8}$ alkoxyl, unsubstituted or substituted C$_{2-10}$ alkenyl, unsubstituted or substituted C$_{2-10}$ alkynyl, unsubstituted or substituted C$_{3-10}$ cycloalkyl, unsubstituted or substituted C$_{6-10}$ aryl, and C$_{6-10}$ aryloxy.
11. The compound of claim 1, where R$^7$ is substituted or unsubstituted C$_{1-10}$ alkyl, substituted or unsubstituted C$_{1-10}$ alkoxy, substituted or unsubstituted aryloxy, or substituted or unsubstituted C$_{3-10}$ cycloalkyl.
12. The compound of claim 1, where n is 1, 2, or 3.
13. The compound of claim 1, where m is 1 or 2, and each Y is a halogen.
14. The compound of claim 1, where m is 0.
15. The compound of claim 1, where substituted alkyl, substituted alkenyl, substituted alkynyl and substituted cycloalkyl can each independently be substituted 1 to 3 times with halogen, —OR', —NR'R", —SR', —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —S(O)R', —S(O)$_2$R', —S(O)$_2$NR"R", —NR'S(O)$_2$R", —CN, oxo (=O or —O—) or —NO$_2$, where R', R" and R"' each are independently selected from the group consisting of hydrogen, halogen, unsubstituted or substituted C$_{1-8}$ alkyl, unsubstituted C$_{3-6}$ cycloalkyl, unsubstituted C$_{2-8}$ alkenyl, unsubstituted or C$_{2-8}$ alkynyl, and unsubstituted aryl.
16. The compound of claim 1, where substituted aryl can each independently be substituted 1 to 3 times with halogen, unsubstituted or substituted alkyl, unsubstituted or substituted alkenyl, unsubstituted or substituted alkynyl, unsubstituted or substituted cycloalkyl, —OR', oxo (=O or —O), —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R"', —NH—C(NH$_2$)=NH, —NR'C(NH$_2$)=NH, —NH—C(NH$_2$)=NR', —S(O)R', —S(O)$_2$R', —S(O)$_2$NR'R", —NR'S (O)$_2$R" and —N$_3$, where R', R" and R'" are independently selected from the group consisting of hydrogen, halogen, unsubstituted C$_{1-8}$ alkyl, unsubstituted C$_{3-6}$ cycloalkyl, unsubstituted C$_{2-8}$ alkenyl, unsubstituted C$_{2-8}$ alkynyl, and unsubstituted or substituted aryl.

17. The compound of claim 1, where substituted heterocyclyl can be substituted 1 to 3 times with halogen, unsubstituted or substituted alkyl, unsubstituted or substituted alkenyl, unsubstituted or substituted alkynyl, unsubstituted or substituted cycloalkyl, —OR', oxo (=O or —O), —OC(O)R', —NR'R", —SR', —R', —CN, —NO$_2$, —OC(O)NR'R", —NR"C(O)R', —NR"C(O)$_2$R', —NR'—C(O)NR"R'", —NH—C(NH$_2$)=NH, —NR'C(NH$_2$)=NH, —NH—C(NH$_2$)=NR', —S(O)R', —S(O)$_2$NR'R", —NR'S(O)$_2$R" and —N$_3$, where R', R"and R'" are independently selected from the group consisting of hydrogen, halogen, unsubstituted C$_{1-8}$ alkyl, unsubstituted or C$_{3-6}$ cycloalkyl, unsubstituted C$_{2-8}$ alkenyl, unsubstituted C$_{2-8}$ alkynyl, and unsubstituted aryl.

18. A compound having the structure (II):

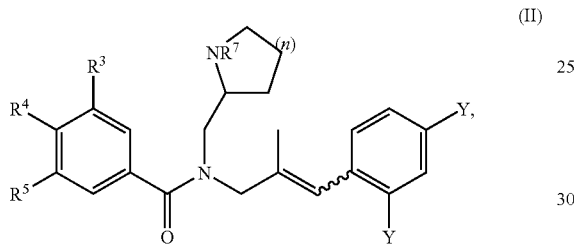

(II)

where n=1;

where each Y is independently hydrogen or halogen;

R$^3$, R$^4$, and R$^5$ are each independently selected from the group consisting of hydrogen, halogen, and —OR'; and R$^7$ is selected from the group consisting of hydrogen, —C(O)R', —CO$_2$R', —C(O)NR'R", —SO$_2$R', unsubstituted or substituted C$_{1-8}$ alkyl (optionally C$_{1-8}$ alkoxyalkyloxy, CH$_2$CH$_2$OCH$_2$CH$_2$OMe)alkyl, unsubstituted or substituted C$_{2-8}$ alkenyl, unsubstituted or substituted C$_{2-8}$ alkynyl, unsubstituted or substituted C$_{3-8}$ cycloalkyl, and unsubstituted or substituted C$_{6-10}$ aryl where each R', R" and R'" are each independently from the group consisting of: hydrogen, halogen, unsubstituted or substituted C$_{1-8}$ alkyl, and unsubstituted or substituted C$_{6-10}$ aryl.

19. The compound of claim 18, where R$^7$ is C$_{1-8}$ alkoxyalkyloxy.

20. A compound comprising one of the following formulae:

1

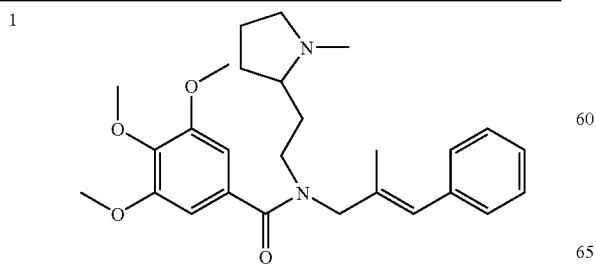

2

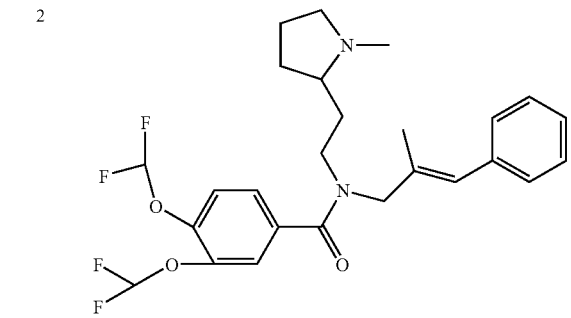

3

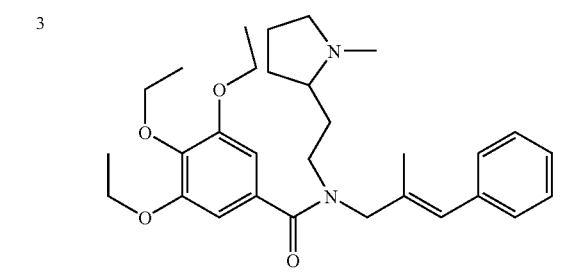

4

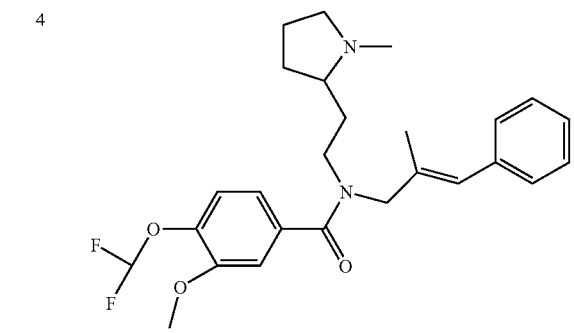

5

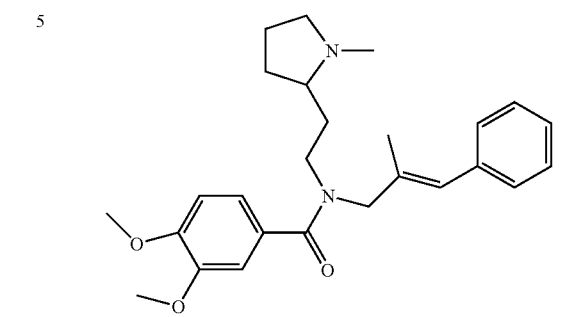

6

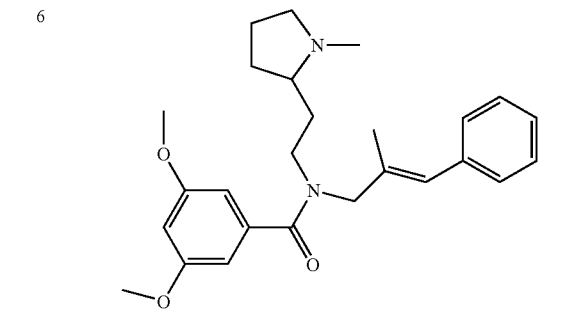

US 7,649,011 B2
| 137 | 138 |
|---|---|
| -continued | -continued |
| 8 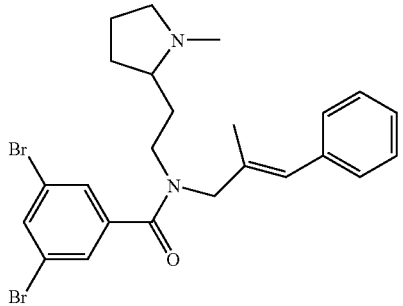 | 14 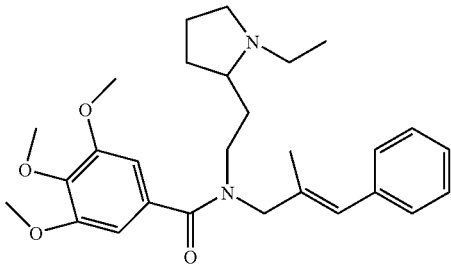 |
| 9 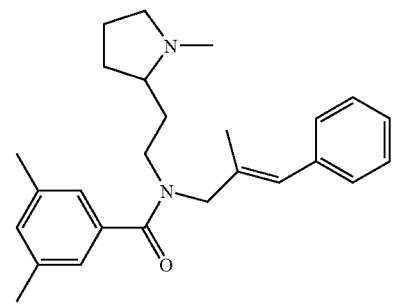 | 15 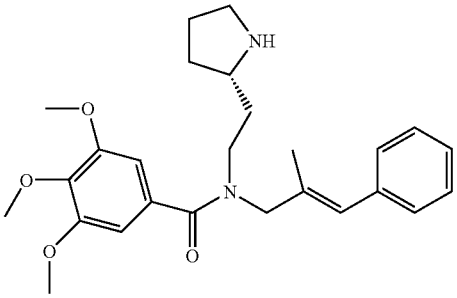 |
| 10 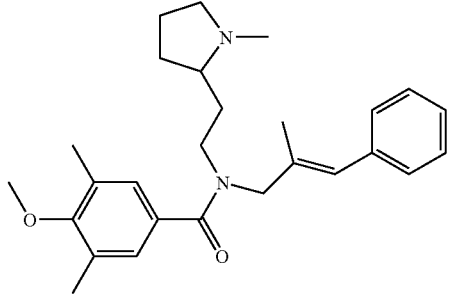 | 16 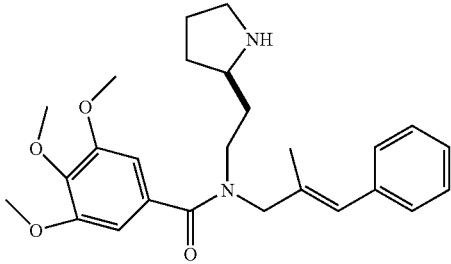 |
| 12 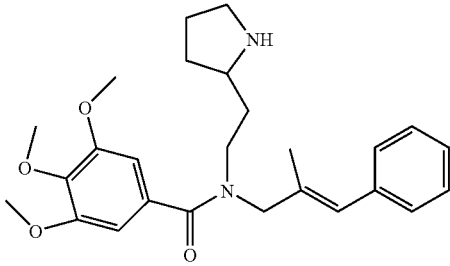 | 17 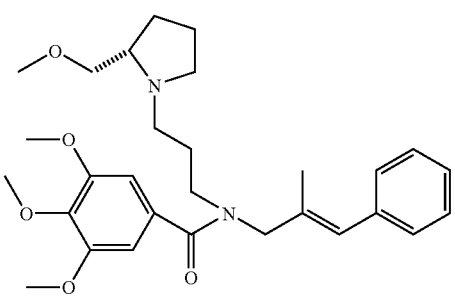 |
| 13 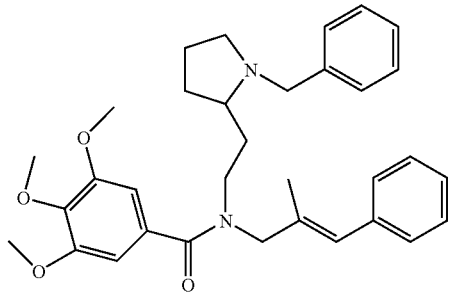 | 18 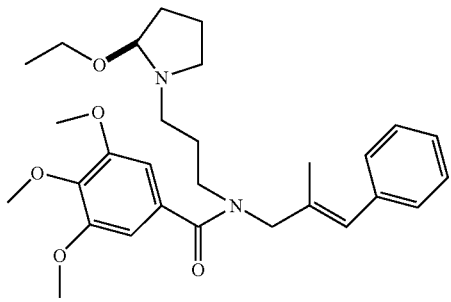 |

20 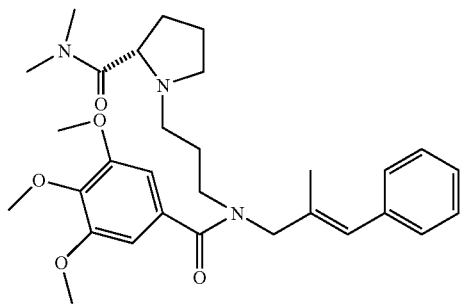
21 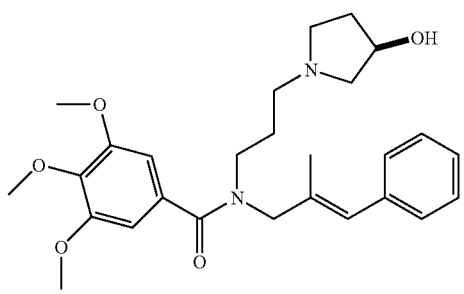
23 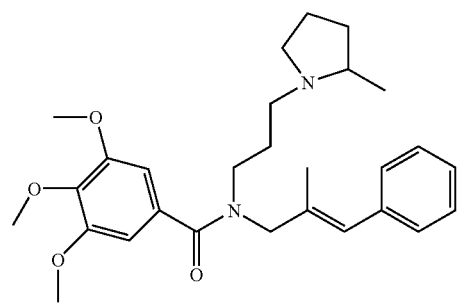
27 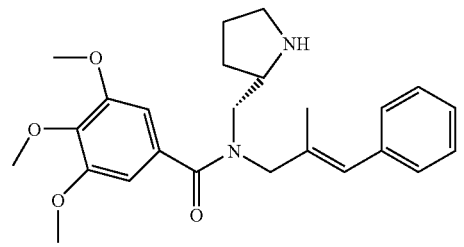
28 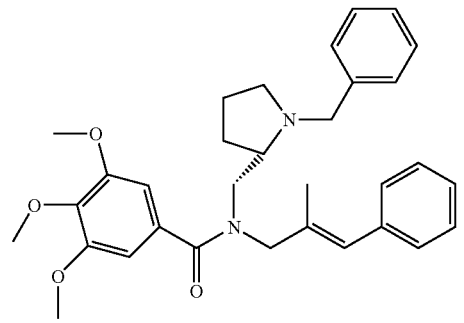
29 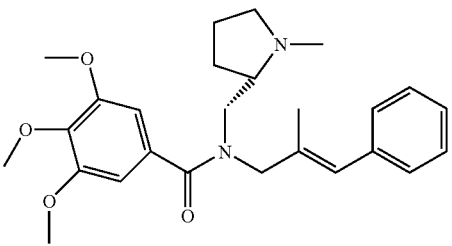
30 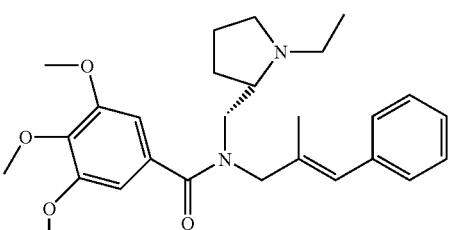
31 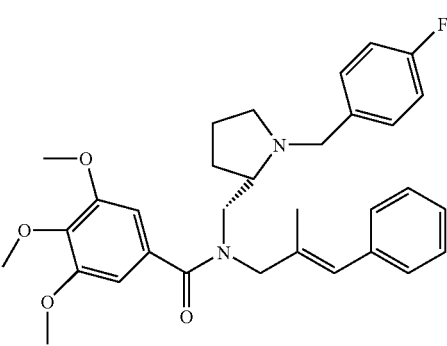
32 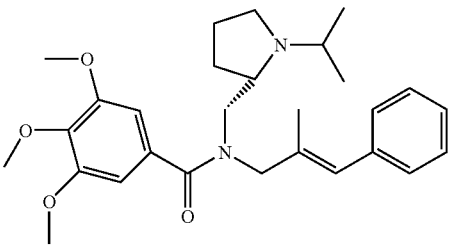
33 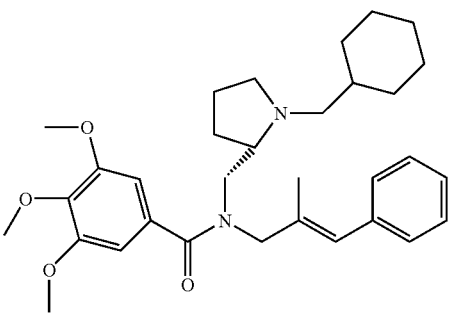

-continued
| | |
|---|---|
| 34 | 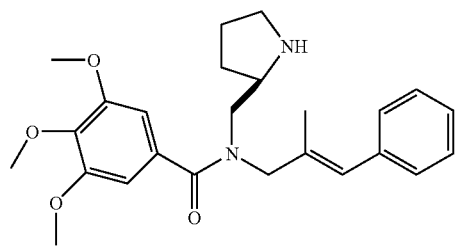 |
| 35 | 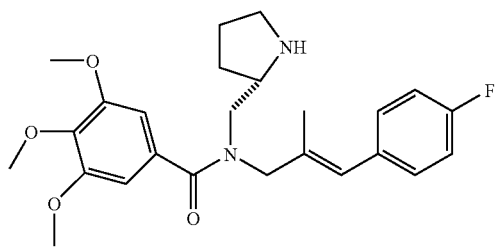 |
| 36 | 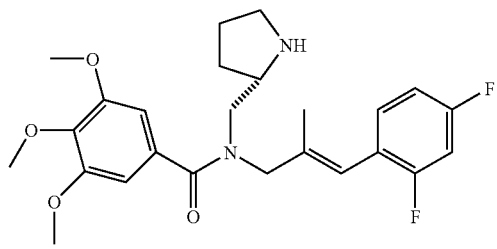 |
| 37 | 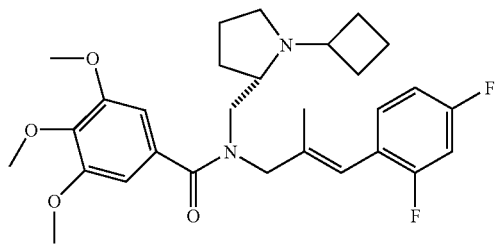 |
| 38 | 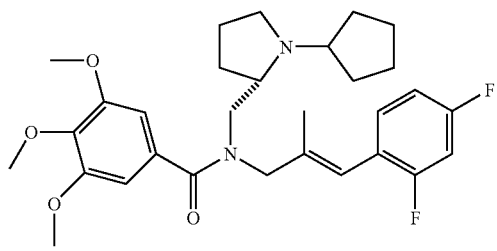 |
| 42 | 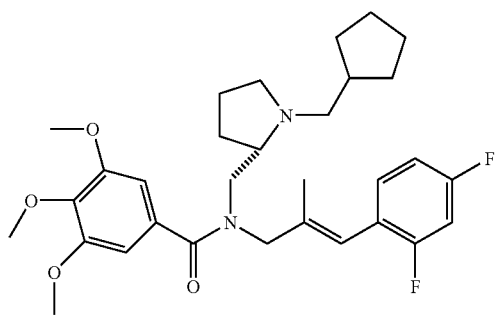 |
-continued
| | |
|---|---|
| 45 | 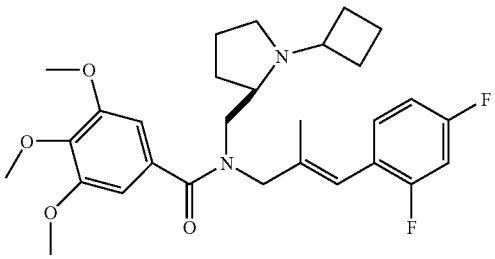 |
| 46 | 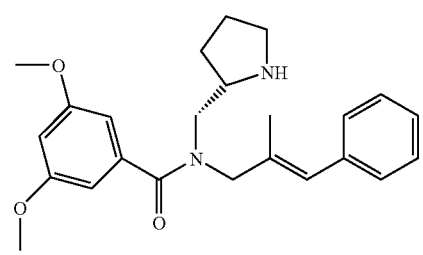 |
| 47 | 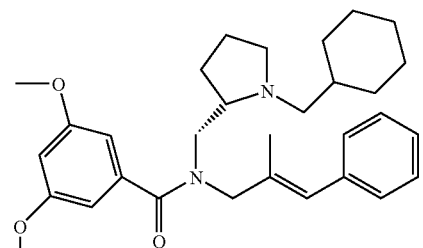 |
| 48 | 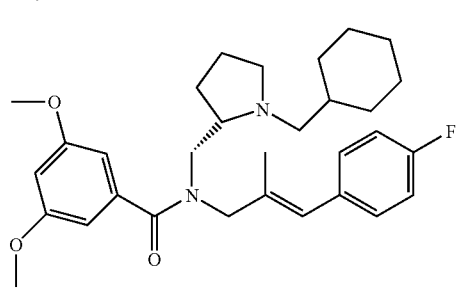 |
| 49 | 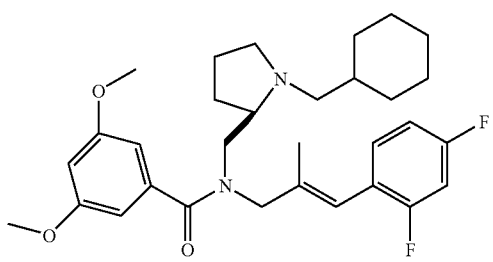 |
| 50 | 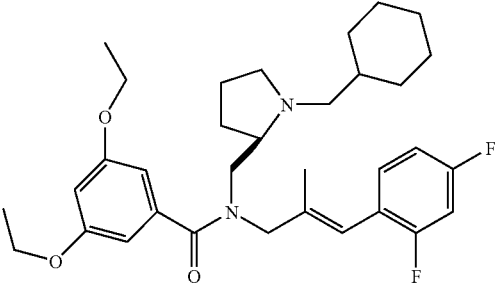 |

| | |
|---|---|
| 51 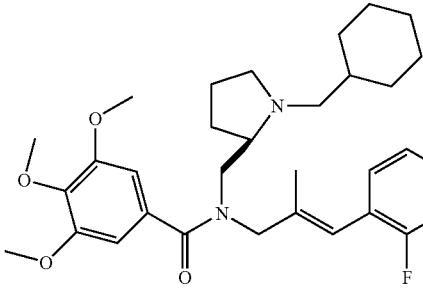 | 57 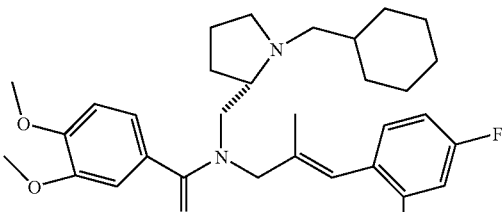 |
| 52 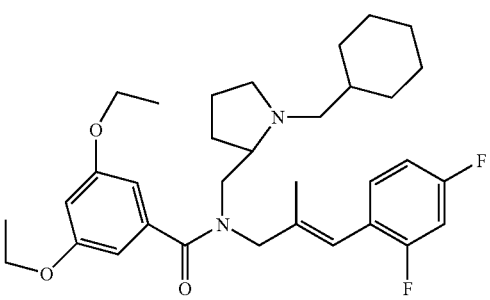 | 58 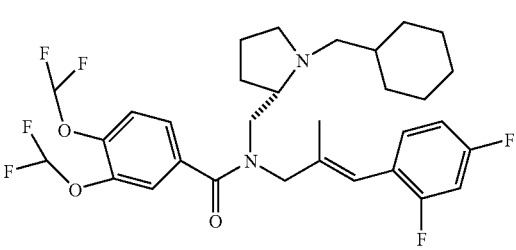 |
| 53 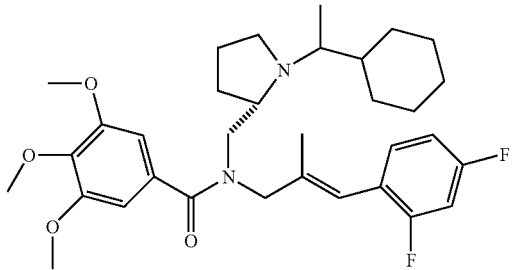 | 60 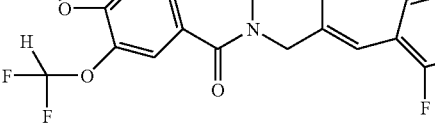 |
| 54 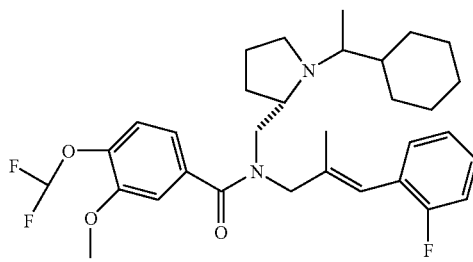 | 61 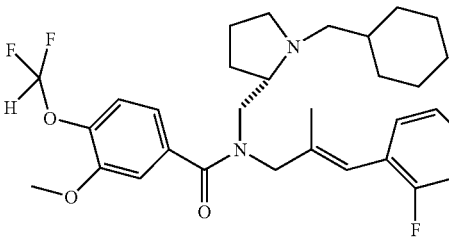 |
| | 62 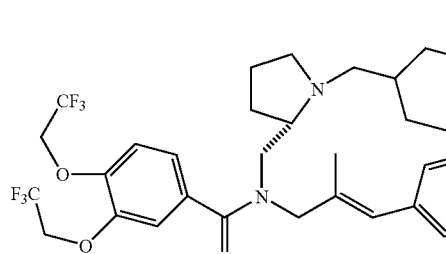 |
| 56 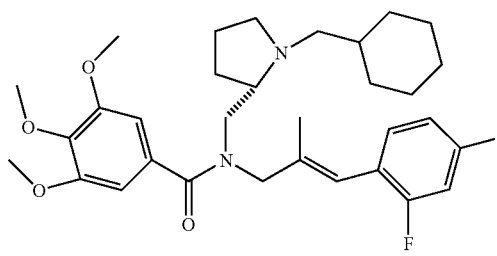 | 64 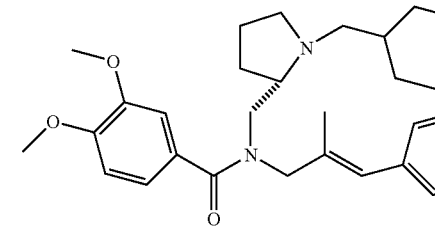 |

| | |
|---|---|
| 65 | 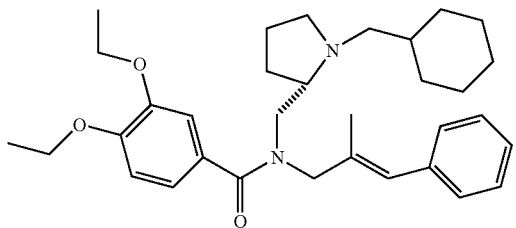 |
| 67 | 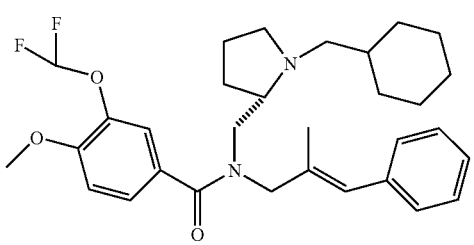 |
| 68 | 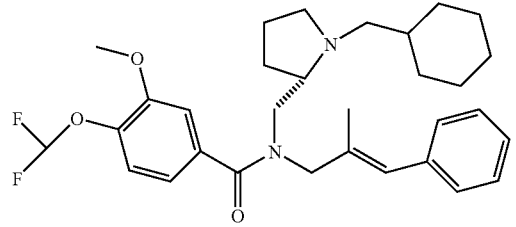 |
| 69 | 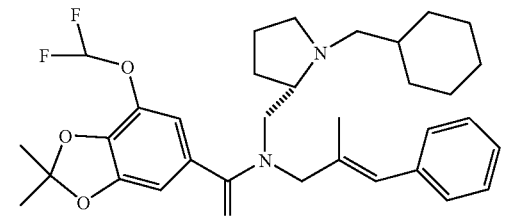 |
| 71 | 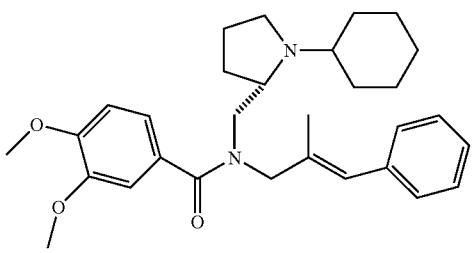 |
| | |
|---|---|
| 73 | 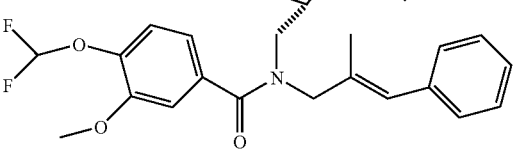 |
| 74 | 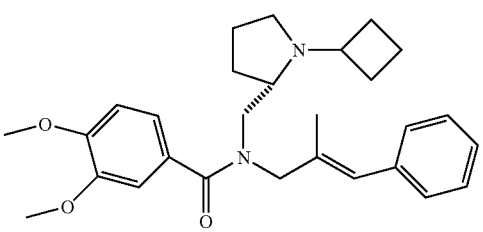 |
| 75 | 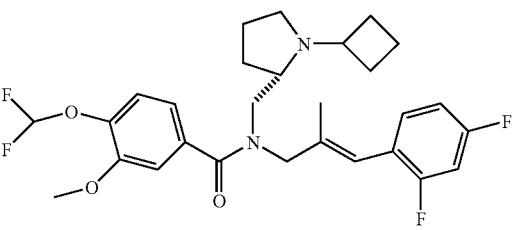 |
| 83 | 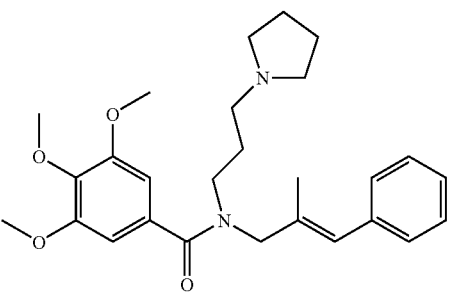 |
| 89 | 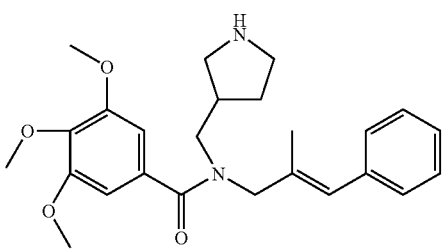 |

91
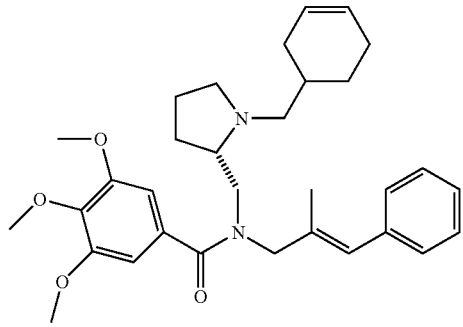
92
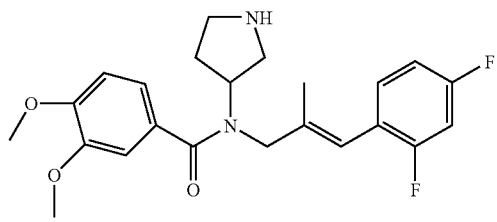
93
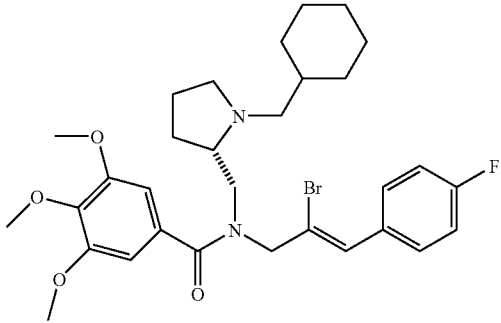
99
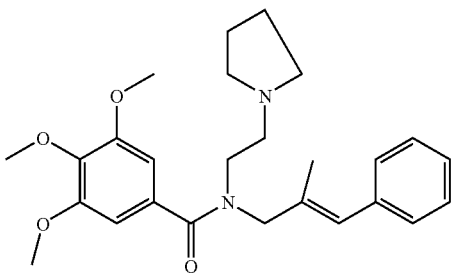
101
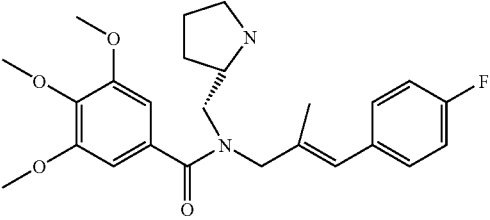
105
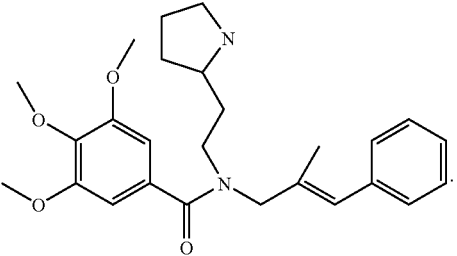
21. A pharmaceutical composition comprising the compound of claim 1 and a pharmaceutically acceptable carrier.
22. A pharmaceutical composition comprising the compound of claim 18 and a pharmaceutically acceptable carrier.
23. A pharmaceutical composition comprising the compound of claim 20 and a pharmaceutically acceptable carrier.
* * * * *

UNITED STATES PATENT AND TRADEMARK OFFICE
CERTIFICATE OF CORRECTION

PATENT NO. : 7,649,011 B2  Page 1 of 1
APPLICATION NO. : 10/743281
DATED : January 19, 2010
INVENTOR(S) : Melikian et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1274 days.

Signed and Sealed this

Twenty-eighth Day of December, 2010

David J. Kappos
*Director of the United States Patent and Trademark Office*

UNITED STATES PATENT AND TRADEMARK OFFICE
CERTIFICATE OF CORRECTION

PATENT NO. : 7,649,011 B2
APPLICATION NO. : 10/743281
DATED : January 19, 2010
INVENTOR(S) : Anita Melikian et al.

It is certified that error appears in the above-identified patent and that said Letters Patent is hereby corrected as shown below:

In the Claims

In column 134, claim 10, line 34, replace "-$SO_2R$," with -- -$SO_2R'$,--.

In column 135, claim 18, line 46, before "the group consisting" replace "independently from" with --independently selected from--.

In column 145, lines 43-52, delete drawing 69 in its entirety.

Signed and Sealed this
Eleventh Day of September, 2012

David J. Kappos
*Director of the United States Patent and Trademark Office*